United States Patent
Liedberg et al.

(10) Patent No.: US 12,359,240 B2
(45) Date of Patent: Jul. 15, 2025

(54) MEMBRANE PROTEASE-BASED METHODS FOR DETECTION OF BACTERIA

(71) Applicants: Nanyang Technological University, Singapore (SG); Northwestern University, Evanston, IL (US)

(72) Inventors: Bo Liedberg, Singapore (SG); Palaniappan Alagappan, Singapore (SG); Sushanth Gudlur, Singapore (SG); Gaurav Sinsinbar, Singapore (SG); Gopal Ammanath, Singapore (SG); Milan Mrksich, Evanston, IL (US); Sarah Elizabeth Wood, Evanston, IL (US)

(73) Assignees: Nanyang Technological University, Singapore (SG); Northwestern University

( * ) Notice: Subject to any disclaimer, the term of this patent is extended or adjusted under 35 U.S.C. 154(b) by 748 days.

(21) Appl. No.: 17/606,167

(22) PCT Filed: Apr. 27, 2020

(86) PCT No.: PCT/SG2020/050256
§ 371 (c)(1),
(2) Date: Oct. 25, 2021

(87) PCT Pub. No.: WO2020/218976
PCT Pub. Date: Oct. 29, 2020

(65) Prior Publication Data
US 2022/0205015 A1  Jun. 30, 2022

Related U.S. Application Data

(60) Provisional application No. 62/838,516, filed on Apr. 25, 2019.

(51) Int. Cl.
*C12Q 1/37* (2006.01)
*C07K 5/103* (2006.01)
*C07K 5/107* (2006.01)

(52) U.S. Cl.
CPC ............ *C12Q 1/37* (2013.01); *C07K 5/1008* (2013.01); *C07K 5/1016* (2013.01); *G01N 2333/245* (2013.01); *G01N 2333/255* (2013.01)

(58) Field of Classification Search
None
See application file for complete search history.

(56) References Cited

U.S. PATENT DOCUMENTS

| | | | | |
|---|---|---|---|---|
| 6,660,484 B2 * | 12/2003 | Charych | ............ | G01N 33/586 435/7.1 |
| 2001/0026915 A1 * | 10/2001 | Charych | ............ | G01N 33/532 435/7.1 |
| 2012/0045474 A1 | 2/2012 | Motin et al. | | |

FOREIGN PATENT DOCUMENTS

| | | | | |
|---|---|---|---|---|
| WO | 2002/081735 A2 | | 10/2002 | |
| WO | WO-02081735 A2 * | | 10/2002 | ........... C07D 333/32 |
| WO | 2004/087942 A2 | | 10/2004 | |

OTHER PUBLICATIONS

Woods, et al. Angew Chem Int Ed Engl. 2017. vol. 56, No. 52, pp. 16531-1635 (Year: 2017).*
International Search Report and Written Opinion issued in corresponding application, PCT/SG2020/050256 on Dec. 10, 2020 (15 pages).
Nilsson K. P. R. et al., Self-assembly of synthetic peptides control conformation and optical properties of a zwitterionic polythiophene derivative. Proc Natl Acad Sci, Jul. 25, 2003, vol. 100, No. 18, pp. 10170-10174.
Wood S. E. et al., A Bottom-Up Proteomic Approach to Identify Substrate Specificity of Outer-Membrane Protease OmpT. Angew Chem Int Ed Engl., Oct. 10, 2017, vol. 56, No. 52, pp. 16531-16535.

* cited by examiner

*Primary Examiner* — Blaine Lankford
(74) *Attorney, Agent, or Firm* — Conley Rose, P.C.

(57) ABSTRACT

The invention provides a method for detecting bacteria. The method utilises a peptide that forms a complex with a conjugated reporter polymer and is susceptible to cleavage by one or more proteases on the surface of a bacteria. Presence or absence of the bacteria can be determined by assessing the optical absorption and/or colour and/or photoluminescence (e.g. fluorescence) of the conjugated reporter polymer, which may undergo a conformational change after binding with the to the cleaved peptide substrate. Specifically, the peptide substrate may comprise a cleavage site for digestion by the protease, and the protease may be an omptin protease. The conjugated reporter polymer may be selected from a polythiophene, a poly(1,4-phenylene vinylene) (PPV), a poly(1,4-phenylene) (PPP), a polyfluorenes (PFO), a nitrogen-containing polymer such as polyquinoline, poly(2,5-pyridinevinylene) (PPyV), 1,3,4-oxadiazole, and poly(9-vinylcarbazole) (PVK), and a polypyrrole. The method may be used to detect contamination in food or water, or as a clinical and/or diagnostic test.

13 Claims, 12 Drawing Sheets
Specification includes a Sequence Listing.

MEMBRANE PROTEASE-BASED METHODS FOR DETECTION OF BACTERIA

CROSS-REFERENCES TO RELATED APPLICATIONS

This application is a U.S. National Phase Application of PCT International Application No. PCT/SG2020/050256, filed Apr. 27, 2020, which is an International Application of and claims the benefit of priority to U.S. Provisional Patent Application No. 62/838,516, filed on Apr. 25, 2019 the entire contents of which are herein incorporated by reference.

FIELD OF INVENTION

This invention relates to methods for detecting pathogenic and non-pathogenic bacteria expressing at least one outer membrane protease by using an unlabelled peptide substrate and a conjugated reporter polymer. The invention also provides a biosensor and a kit. More particularly, the invention may be used to detect bacteria such as *Escherichia coli* (*E. coli*), *Salmonella* and other Enterobacteriaceae in water, food, clinical samples and biological fluids.

BACKGROUND

The listing or discussion of a prior-published document in this specification should not necessarily be taken as an acknowledgement that the document is part of the state of the art or is common general knowledge.

A 2015 World Health Organization report found that food and water borne illnesses affect 1 in 10 individuals around the world, contributing to mortality and impeding socio-economic development. This largely unreported, undiagnosed, and untreated class of diseases takes a substantial toll on societies. Examples of pathogenic bacteria frequently identified as causing such illnesses are *E. coli* and *Salmonella*, which together are responsible for approximately 120,000 deaths per year globally. These pathogens spread via contaminated water and uncooked food, causing infections characterized by diarrhoea, fever, abdominal pain, and nausea, leading in extreme cases to severe dehydration.

Detection of non-pathogenic bacteria is also important in, for example, municipal water supply quality control, where the total level of *E. coli* (whether a pathogenic or non-pathogenic strain), must not exceed a certain level.

Current gold standard tests (i.e. biochemical tests and 16S rRNA sequencing) for detecting bacteria (e.g. pathogenic bacteria) require pre-processing (i.e. homogenisation, enrichment and separation of pathogens) of water and food samples, followed by culturing in a growth medium. This culturing typically takes from 12 hours to 7 days, substantially delaying the final biochemical assay required to identify and quantify the level of bacterial contamination [Wang, Y. & Salazar, J. K. *Compr. Rev. Food Sci. Food Saf.* 15, 183-205 (2016), and Lazcka, O., Campo, F. J. Del & Munoz, F. X. *Biosens. Bioelectron.* 22, 1205-1217 (2007)]. The overall testing and detection process can take up to a week and requires trained personnel. While this approach can be acceptable in certain circumstances, it is not appropriate for home testing or in the food industry, where it is not feasible to wait for days to confirm if the food or water for consumption or for packaging and shipment is contaminated. Although various rapid detection methods based on nucleic acid and immunoassays have been developed to reduce the assay time to about 24 h, they are laboratory-based and require specialized instruments and trained personnel [Wang, Y. & Salazar, J. K. *Compr. Rev. Food Sci. Food Saf.* 15, 183-205 (2016), and Law, J. W.-F. et al., *Front. Microbiol.* 5, 770 (2014)].

Polymer-based fluorescence biosensors have been reported previously but they are either based on nonspecific electrostatic interactions between polymer chains and bacterial surface, or peptides which bind differentially to the components of bacterial surfaces. These sensing approaches are therefore nonspecific with higher limits of detection [Kramer, R. A. et al., *Eur. J. Biochem.* 267, 885-893 (2000); Dekker, N. et al., *Biochemistry* 40, 1694-1701 (2001)]. Chromogenic media-based assays for bacterial detection, such as those from Bio-Rad, also possess an overall assay time of up to 48 h. Although some bacterial detection kits for household usage are commercially available, they are time-consuming and non-specific. For instance, AqualVial™, a water testing kit sold by AquaBSafe (Ontario, Canada) for *E. coli* detection is time-consuming and requires an incubation time of around 24 h before the results can be reported.

Given the above, there is a need to develop an improved bacterial detection method that is rapid, sensitive, and does not require sophisticated equipment.

SUMMARY OF INVENTION

Omptin is a family of proteases that are present on the outer membrane of some gram-negative enterobacteria, such as *E. coli, Salmonella*, and others [Mangel, B. W. F., Toledo, D. L. & Brown, *Methods Enzymol.* 244, 384-399 (1994); and Dekker, N. *Handbook of Proteolytic Enzymes* 1, 284-289 (Elsevier, 2013)]. Omptin proteases degrade antimicrobial peptides produced by the human immune system and are also involved in the virulence of the bacterial pathogens.

The inventors have surprisingly determined that by providing a peptide substrate for one or more proteases on the outer membrane or surface of a bacteria and a conjugated reporter polymer that interacts with said peptide, it is possible to provide a highly sensitive, easy to use detection method that does not require sophisticated equipment or highly trained users. In particular, the methods of the invention can provide a rapid colour change visible to the naked eye.

According to a first aspect of the invention, there is provided a method for detecting in a test sample the presence or absence of bacteria expressing at least one outer membrane protease, the method comprising the steps:
(i) contacting the test sample with a peptide substrate that is cleaved by said protease;
(ii) simultaneously or sequentially contacting the test sample with a conjugated reporter polymer for a predetermined period of time, wherein intact peptide substrate forms a complex with the conjugated reporter polymer and induces a change in conformation, whereas the cleaved peptide fragments are unable to induce a change in conformation, and
(iii) comparing the optical absorption and/or colour and/or photoluminescence (e.g. fluorescence) of the test sample with a control.

In some embodiments the method comprises the steps:
(i) contacting the test sample with the peptide substrate simultaneously with the conjugated reporter polymer for a predetermined period of time, wherein intact peptide substrate forms a complex with the conjugated reporter polymer and induces a change in conformation, whereas the cleaved peptide fragments are unable to induce a change in conformation; and (ii) comparing the optical absorption and/or colour and/or photoluminescence (e.g. fluorescence) of the test sample with a control.

In some embodiments the method comprises the steps:
(i) contacting the test sample with the peptide substrate for a predetermined period of time, wherein intact peptide substrate forms a complex with the conjugated reporter polymer and induces a change in conformation, whereas the cleaved peptide fragments are unable to induce a change in conformation;
(ii) contacting the test sample from step (i) with a conjugated reporter polymer; and
(iii) comparing the optical absorption and/or colour and/or photoluminescence (e.g. fluorescence) of the test sample with a control.

In some embodiments the bacteria is a pathogenic bacteria. In some embodiments the bacteria is a gram-negative bacteria. In some embodiments the bacteria is selected from the group comprising or consisting of *Escherichia coli, Salmonella enterica, Yersinia pestis* and *Shigella flexneri*.

In some embodiments the conjugated reporter polymer is selected from the group consisting of a polythiophene; a poly(1,4-phenylene vinylene) (PPV); a poly(1,4-phenylene) (PPP); a polyfluorenes (PFO); a nitrogen-containing polymer such as polyquinoline, poly(2,5-pyridinevinylene), 1,3, 4-oxadiazole, and poly(9-vinylcarbazole) (PVK); and a polypyrrole.

In some embodiments the conjugated reporter polymer is a polythiophene reporter polymer. In some embodiments the conjugated polythiophene reporter polymer is polythiophene acetic acid (PTAA), Poly[3(potassium-6-hexanoate)thiophene-2,5-diyl] (PT6), Poly[3-(Potassium-4-butanoate)thiophene-2,5-diyl] (PT4), or any combination thereof. Preferably, the conjugated reporter polymer is Poly[3(potassium-6-hexanoate)thiophene-2,5-diyl] (PT6).

In some embodiments the at least one outer membrane protease is an omptin protease. In some embodiments the omptin protease is selected from the group comprising or consisting of OmpT, OmpP, PgtE, PgtE2, Pla, PlaA SopA, SopA2, SopA3, IscP, Q8ZGQ6, Staphylococcal peptidase I, and Protease 7. In some embodiments the omptin protease is OmpT and the bacteria is *Escherichia coli*.

In some embodiments the peptide substrate is a peptide comprising two adjacent basic amino acid residues, wherein each of the basic amino acid residue is independently selected from the group comprising or consisting of Lysine, Arginine or Histidine. In some embodiments the peptide substrate comprises a cleavage site comprising an amino acid sequence set forth in the group comprising or consisting of FRRV (SEQ ID NO: 1), FRRY (SEQ ID NO: 2), FRRA (SEQ ID NO: 3), YRRA (SEQ ID NO: 4) and ARRA (SEQ ID NO: 5). In some embodiments the peptide substrate has an N-terminal cysteine residue, which was found to improve the fluorescence intensity of complexed substrate and reporter polymer.

In some embodiments the peptide substrate has at least 30%, at least 40%, at least 50%, at least 60%, at least 70%, at least 80%, at least 90%, or 100% sequence similarity with a peptide selected from the group comprising or consisting of cathelicidin LL37 (SEQ ID NO: 6) or a functional fragment thereof, LL37$_{FRRV}$ C L L G D F F R R V K E K I G (SEQ ID NO: 7), LL37$_{FRRY}$ C L L G D F F R R Y K E K I G (SEQ ID NO: 8), LL37$_{FRRA}$ C L L G D F F R R A K E K I G (SEQ ID NO: 9), LL37$_{YRRA}$ C L L G D F Y R R A K E K I G (SEQ ID NO: 10), LL37$_{ARRA}$ C L L G D F A R R A K E K I G (SEQ ID NO: 11), LL37$_{ARKA}$ C L L G D F A R K A K E K I G (SEQ ID NO: 12), SEQ ID NO: 13 to SEQ ID NO: 54, or a functional fragment thereof. Preferably, the peptide substrate comprises an amino acid sequence that, when optimally aligned using an alignment tool such as EMBOSS-Needle (worldwidewebdotebidotac-dotuk/Tools/psa/emboss_needle/), will generate a similarity of at least 60(%) with a peptide selected from the group comprising or consisting of cathelicidin LL37 (SEQ ID NO: 6) or a functional fragment thereof, LL37$_{FRRV}$ C L L G D F F R R V K E K I G (SEQ ID NO: 7), LL37$_{FRRY}$ C L L G D F F R R Y K E K I G (SEQ ID NO: 8), LL37$_{FRRA}$ C L L G D F F R R A K E K I G (SEQ ID NO: 9), LL37$_{YRRA}$ C L L G D F Y R R A K E K I G (SEQ ID NO: 10), LL37$_{ARRA}$ C L L G D F A R R A K E K I G (SEQ ID NO: 11), LL37$_{ARKA}$ C L L G D F A R K A K E K I G (SEQ ID NO: 12), SEQ ID NO: 13 to SEQ ID NO: 54, or a functional fragment thereof, wherein the peptide complexes with the conjugated reporter polymer and induces a change in conformation, and wherein the cleaved peptide is unable to induce a change in conformation of said conjugated reporter polymer."

Preferably, a peptide substrate is a peptide comprising an amino acid sequence set forth in the group comprising or consisting of SEQ ID NO: 6 to SEQ ID NO: 54, or a functional fragment thereof. It would be understood that any fragments or sequence variants of a peptide must comprise two adjacent basic amino acid residues, wherein each of the basic amino acid residue is independently selected from the group comprising or consisting of Lysine, Arginine or Histidine to function as a peptide substrate. In some embodiments the peptide substrate defined by any one of SEQ ID NO: 7 to SEQ ID NO: 12 does not have an N-terminal cysteine residue and comprises or consists of the peptide sequences set forth in sequences L L G D F F R R V K E K I G (SEQ ID NO: 13), L L G D F F R R Y K E K I G (SEQ ID NO: 14), L L G D F F R R A K E K I G (SEQ ID NO: 15), L L G D F Y R R A K E K I G (SEQ ID NO: 16) and L L G D F A R R A K E K I G (SEQ ID NO: 17), SEQ ID NO: 49, SEQ ID NO: 50, SEQ ID NO: 51, SEQ ID NO: 52, SEQ ID NO: 53 and SEQ ID NO: 54.

It would be understood that peptides herein described, such as cathelicidin LL37 (SEQ ID NO: 6) and Myticalin C6 (SEQ ID NO: 45), may be shortened and act as a suitable peptide substrate provided they comprise two adjacent basic amino acid residues that are cleaved by a target protease.

In some embodiments the peptide substrates, for example defined by SEQ ID NOs: 1 to 17 and 49 to 54 may have additional amino acids at the amino-terminal and/or carboxy-terminal ends and remain functional in terms of acting as a protease substrate and being capable of complexing with a reporter polymer according to the invention. Preferably, the peptide substrates defined by SEQ ID NOs: 1 to 17 and 49 to 54 have no more than 10 additional amino acids at the amino-terminal and/or carboxy-terminal ends. For example, each peptide substrate of the invention could be represented by, for example, the formula X1-A-X2, where X1 and X2 are, independently, a sequence of 0-10 amino acid residues and A is a peptide that has at least 40%, at least 50%, at least 60%, at least 70%, at least 80%, at least 90%, or 100% sequence similarity with a peptide set forth in any one of SEQ ID NO: 1 to 17 and SEQ ID NO: 49 to 54.

In some embodiments the peptide substrate comprises or consists of an amino acid sequence selected from the group comprising or consisting of SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 49, SEQ ID NO: 50, SEQ ID NO: 51, SEQ ID NO: 52, SEQ ID NO: 53 and SEQ ID NO: 54. In some embodiments the peptide substrate consists of an amino acid sequence selected from the group consisting of SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 49, SEQ ID NO: 50, SEQ ID NO: 51, SEQ ID NO: 52, SEQ ID NO: 53 and SEQ ID NO: 54.

In some embodiments the bacteria are selected from the group comprising or consisting of *Escherichia coli, Salmonella enterica, Yersinia pestis* and *Shigella flexneri;* the conjugated reporter polymer is polythiophene acetic acid (PTAA), Poly[3(potassium-6-hexanoate)thiophene-2,5-diyl] (PT6), Poly[3-(Potassium-4-butanoate) thiophene-2,5-diyl] (PT4), or any combination thereof; and
- the peptide substrate has at least 40% sequence similarity with a peptide comprising an amino acid sequence set forth in the group comprising or consisting of SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 49, SEQ ID NO: 50, SEQ ID NO: 51, SEQ ID NO: 52, SEQ ID NO: 53 and SEQ ID NO: 54, or a functional fragment thereof.

In some embodiments the method according to any aspect of the invention further comprises a pre-culturing step or pre-concentration step before performing step (i) of the method, wherein the pre-culturing step involves incubating the test sample under culturing conditions; and wherein the pre-concentration step involves removing excess aqueous solution from the test sample while retaining the bacteria. In some embodiments the pre-culturing step comprises culturing the test sample in a growth medium for not more than 12 hours, preferably not more than 7 hours. In some embodiments the pre-concentration step comprises pelleting the test sample followed by re-suspending the test sample.

In some embodiments the test sample is derived from a source selected from the group comprising or consisting of a water source, a food source, a clinical sample and a biological fluid. In some embodiments the test sample is a sample isolated from a patient. In some embodiments the test sample is a urine sample.

In some embodiments the method comprises a test to detect contamination in water and/or food sources. In some embodiments the method comprises a clinical and/or diagnostic test.

In some embodiments said predetermined period of time for contacting the test sample with a conjugated reporter polymer is in the range of 1 minute to 2 hours.

In some embodiments the peptide substrate comprises a cleavage site comprising an amino acid sequence set forth in the group comprising or consisting of FRRV (SEQ ID NO: 1), FRRY (SEQ ID NO: 2), FRRA (SEQ ID NO: 3), YRRA (SEQ ID NO: 4) and ARRA (SEQ ID NO: 5). In some embodiments the peptide substrate is specific for omptin protease on bacteria. In some embodiments the peptide substrate has at least 30%, at least 40%, at least 50%, at least 60%, 70%, at least 80%, at least 90%, or 100% sequence similarity with a peptide selected from the group comprising or consisting of SEQ ID NO: 6 to SEQ ID NO: 54, providing any fragments or sequence variants of a peptide must comprise two adjacent basic amino acid residues, wherein each of the basic amino acid residue is independently selected from the group comprising or consisting of Lysine, Arginine or Histidine to function as a peptide substrate. In some embodiments the peptide substrate amino acid sequence is selected from the group consisting of SEQ ID NO: 6 to SEQ ID NO: 54.

A second aspect of the invention provides an isolated peptide substrate, wherein the peptide substrate comprises a cleavage site selected from the group comprising or consisting of FRRV (SEQ ID NO: 1), FRRY (SEQ ID NO: 2), FRRA (SEQ ID NO: 3), YRRA (SEQ ID NO: 4) and ARRA (SEQ ID NO: 5). In some embodiments the peptide substrate is specific for omptin protease on bacteria. In some embodiments the peptide substrate has at least 30%, at least 40%, at least 50%, at least 60%, at least 70%, at least 80%, at least 90%, or 100% sequence similarity with a peptide comprising an amino acid sequence set forth in the group comprising or consisting of cathelicidin LL37 (SEQ ID NO: 6), $LL37_{FRRV}$ C L L G D F F R R V K E K I G (SEQ ID NO: 7), $LL37_{FRRY}$ C L L G D F F R R Y K E K I G (SEQ ID NO: 8), $LL37_{FRRA}$ C L L G D F F R R A K E K I G (SEQ ID NO: 9), $LL37_{YRRA}$ C L L G D F Y R R A K E K I G (SEQ ID NO: 10), $LL37_{ARRA}$ C L L G D F A R R A K E K I G (SEQ ID NO: 11) and $LL37_{ARKA}$ C L L G D F A R K A K E K I G (SEQ ID NO: 12), SEQ ID NO: 13, SEQ ID NO: 14, SEQ ID NO: 15, SEQ ID NO: 16 and SEQ ID NO: 17, provided that the isolated peptide substrate is not cathelicidin LL37 (SEQ ID NO: 6). In some embodiments the peptide substrate amino acid sequence has at least 40% sequence similarity, preferably at least 60% sequence similarity, with the above-mentioned peptides. In some embodiments the peptide substrate consists of an amino acid sequence set forth in the group consisting of SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16 and SEQ ID NO: 17, SEQ ID NO: 49, SEQ ID NO: 50, SEQ ID NO: 51, SEQ ID NO: 52, SEQ ID NO: 53 and SEQ ID NO: 54.

In some embodiments the peptide substrates, for example defined by SEQ ID NOs: 1 to 17 and 49 to 54 may have additional amino acids at the amino-terminal and/or carboxy-terminal ends and remain functional in terms of acting as a protease substrate and being capable of complexing with a reporter polymer according to the invention. Preferably, the peptide substrates defined by SEQ ID NOs: 1 to 17 and 49 to 54 have no more than 10 additional amino acids at the amino-terminal and/or carboxy-terminal ends. For example, each peptide substrate of the invention could be represented by, for example, the formula X1-A-X2, where X1 and X2 are, independently, a sequence of 0-10 amino acid residues and A is a peptide that has at least 40%, at least 50%, at least 60%, at least 70%, at least 80%, at least 90%, or 100% sequence similarity with a peptide set forth in any one of SEQ ID NO: 1 to 17 and SEQ ID NO: 49 to 54.

A third aspect of the invention provides use of a peptide substrate with a conjugated reporter polymer for the detection in a test sample of the presence or absence of bacteria expressing at least one outer membrane protease, wherein the peptide substrate is cleaved by said outer membrane protease and can no longer form a complex with and change the conformation of the conjugated reporter polymer.

A fourth aspect of the invention provides a biosensor to detect in a test sample the presence or absence of bacteria, said biosensor comprising a solid support and a conjugated reporter polymer that changes the conformation in the presence of intact peptide substrate specific for an outer membrane protease expressed by said bacteria, said conjugated reporter polymer attached to said solid support. In some embodiments the conjugated reporter polymer is a polythiophene.

In some embodiments the peptide substrate comprises a cleavage site selected from the group comprising or consisting of FRRV (SEQ ID NO: 1), FRRY (SEQ ID NO: 2), FRRA (SEQ ID NO: 3), YRRA (SEQ ID NO: 4) and ARRA (SEQ ID NO: 5). In some embodiments the peptide substrate for use with the biosensor is specific for omptin protease on bacteria. In some embodiments the peptide substrate has at least 30%, at least 40%, at least 50%, at least 60%, at least 70%, at least 80%, at least 90%, or 100% sequence similarity with a peptide selected from the group comprising or consisting of cathelicidin LL37 (SEQ ID NO: 6), $LL37_{FRRV}$ C L L G D F F R R V K E K I G (SEQ ID NO: 7), $LL37_{FRRY}$ C L L G D F F R R Y K E K I G (SEQ ID NO: 8), $LL37_{FRRA}$ C L L G D F F R R A K E K I G (SEQIDNO: 9), $LL37_{YRRA}$ C L L G D F Y R R A K E K I G (SEQ ID NO: 10), $LL37_{ARRA}$ C L L G D F A R R A K E K I G (SEQ ID NO: 11), $LL37_{ARKA}$ C L L G D F A R K A K E K I G (SEQ ID NO: 12), L L G D F F R R V K E K I G (SEQ ID NO: 13), L L G D F F R R Y K E K I G (SEQ ID NO: 14), L L G D F F R R A K E K I G (SEQ ID NO: 15), L L G D F Y R R A K E K I G (SEQ ID NO: 16) and L L G D F A R R A K E K I G (SEQ ID NO: 17) and any one of SEQ ID NO: 49 to SEQ ID NO: 54, or a functional fragment thereof. Preferably, the peptide substrate has at least 70% sequence similarity with a peptide selected from the group comprising or consisting of SEQ ID NO: 6 to SEQ ID NO: 46. In some embodiments the peptide substrate amino acid sequence is selected from the group consisting of SEQ ID NO: 6, SEQ ID NO: 7, SEQ ID NO: 8, SEQ ID NO: 9, SEQ ID NO: 10, SEQ ID NO: 11 and SEQ ID NO: 12.

A fifth aspect of the invention provides a kit for screening a test sample for the presence of at least one outer membrane protease indicative of bacteria, comprising a peptide substrate and a conjugated reporter polymer, wherein intact peptide substrate forms a complex with and alters the conformation of a conjugated reporter polymer. In some embodiments the bacteria is as defined in the first aspect. In some embodiments the at least one outer membrane protease is as defined in the first aspect. In some embodiments the conjugated reporter is a conjugated polythiophene reporter polymer. In some embodiments the conjugated polythiophene reporter polymer is as defined in the first aspect. In some embodiments the peptide substrate is as defined in the first aspect.

BRIEF DESCRIPTION OF DRAWINGS

FIG. 14A shows a comparison of changes in PT6 fluorescence when mixed with different peptide substrates incubated with E. coli K12 (solid line) and BL21 cells (dashed line) for increasing time periods. FIG. 14B shows colorimetric data of PT6 when mixed with various peptide substrates exposed to E. coli. The samples of FIG. 14A were imaged under normal visible light (top) and UV light (bottom).

DETAILED DESCRIPTION OF PREFERRED EMBODIMENTS

Figure 1:
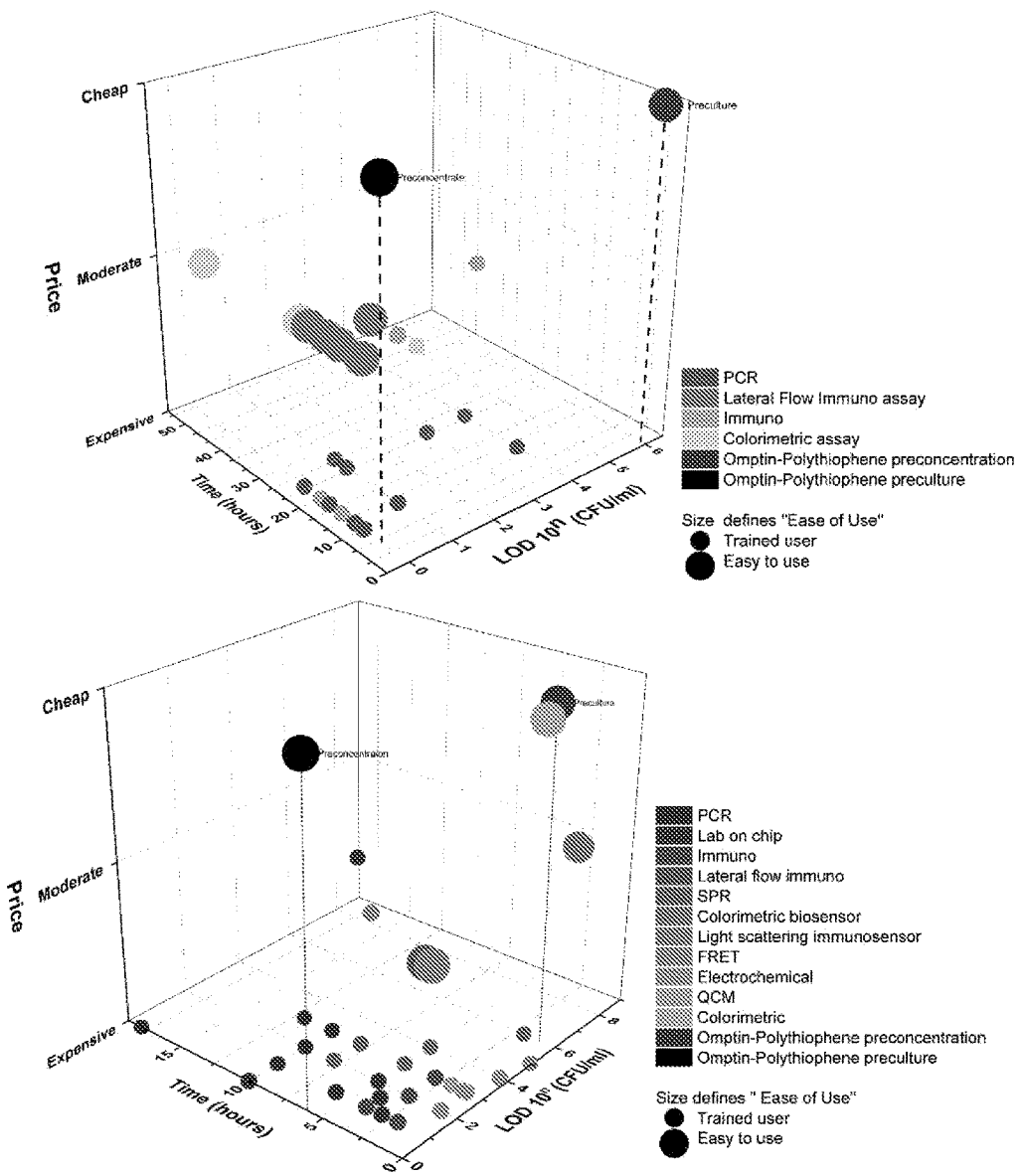
FIG. 1 compares the membrane protease-based detection methods of the invention with A) commercially available pathogen testing kits; and B) laboratory-based approaches for detecting bacterial pathogen. The graphs compare detection time, limit of detection (LOD), cost and ease of use.

In embodiments herein, the word "comprising" may be interpreted as requiring the features mentioned, but not limiting the presence of other features. Alternatively, the word "comprising" may also relate to the situation where only the components/features listed are intended to be present (e.g. the word "comprising" may be replaced by the phrases "consists of" or "consists essentially of"). It is explicitly contemplated that both the broader and narrower interpretations can be applied to all aspects and embodiments of the present invention. In other words, the word "comprising" and synonyms thereof may be replaced by the phrase "consisting of" or the phrase "consists essentially of" or synonyms thereof and vice versa.

The invention is described below with reference to various features and embodiments. It is herein explicitly contemplated that any feature or embodiment described below may be combined with any other feature or embodiment in any technically sensible way. For example, a peptide substrate defined in relation to one embodiment may be combined with any other embodiment.

The invention provides methods for detecting bacteria in a test sample, wherein the bacteria expresses one or more proteases on its outer membrane. In some embodiments of the invention, the bacteria are pathogenic bacteria. In other embodiments of the invention, the bacteria are non-pathogenic bacteria. In some embodiments of the invention, the one or more proteases may be one or more omptin proteases. In particular, the bacteria may be a gram-negative enterobacteria, for example a gram-negative enterobacteria that expresses at least one omptin protease on its outer membrane. In embodiments of the invention that may be mentioned herein, the bacteria may be selected from the group consisting of Escherichia coli, Salmonella enterica, Yersinia pestis and Shigella flexneri. In embodiments of the invention that may be mentioned herein, the omptin protease may be selected from the group comprising OmpT, OmpP, PgtE, PgtE2, Pla, PlaA SopA, SopA2, SopA3, IscP, Q8ZGQ6, Staphylococcal peptidase I, and Protease 7. In particular embodiments of the invention that may be mentioned herein, the bacteria may be Escherichia coli, and/or the omptin protease may be OmpT. The bacteria that produces the specific membrane proteases listed above are provided in Table 1.

TABLE 1

| List of omptin proteases | |
|---|---|
| Protease | Organism |
| OmpT | Escherichia coli |
| OmpP | Escherichia coli |
| SopA/IcsP | Shigella flexneri enteroinvasive E. coli |
| SopA2/SopA3 | Shigella dysenteriae |
| PgtE/PgtE2 | Salmonella enterica |
| Pla | Yersinia pestis |
| PlaA | Erwinia pyrifoliae |
| Q8ZGQ6 | Yersinia pestis |
| Staphylococcal peptidase I | Staphylococcus aureus |
| Protease 7 | Citrobacter rodentium |

The test sample can be any sample that is suspected of being contaminated with bacteria. Examples of such samples include food such as meat, vegetable (row crops and seeded vegetables), fruits, dairy products, grains-beans, oils and sugar; water such as municipal water, tap water and water in a swimming pool; a clinical sample; including biological fluid samples such as urine. As such, the methods of the invention may be used to detect contamination in food/water sources, and in the clinical/diagnostic setting.

Where the test sample is an aqueous solution, it may be used directly in the methods of the invention. However, if the expected level of contamination is low, it may be desired to increase the sensitivity of the method by performing a step to increase the amount or concentration of bacteria in the test sample, for example a pre-concentration or pre-culturing step or a combination of both. Where the test sample is a solid, it may be added to aqueous solution for testing without further processing, or it may be broken up or otherwise processed in order to be suspended in, or added to, aqueous solution. Alternatively, or in addition, the solid may be washed with water and the washings used in place of, or as well as, the solid test sample. It may be desirable to perform a pre-concentration or pre-culturing step on any such washings, since the level of bacterial contamination in the washings may be low. When the test sample is coloured or exhibits intrinsic fluorescence, it may be desirable to process the test sample in order to reduce or remove the colour and intrinsic fluorescence emission, while retaining any potential bacterial contamination. This may be particularly desirable if the detection method is intended to rely on a visible colour or fluorescence emission change that may be obscured if a strongly coloured or fluorescently active test sample is used. For example, the test sample could be filtered, centrifuged or treated with one or more sorbents to remove pigments, examples of which are shown in Table 2, followed by a resuspension step, in order to remove or reduce the level of colour.

then re-suspending the isolated bacteria in a lower volume of liquid (i.e. water), to produce a sample having an increased concentration. For example, the bacteria may be isolated (e.g. pelleted) by filtering and/or centrifuging, and the isolated bacteria may then be re-suspended by vortexing. A pre-concentration step can be performed in as little as 5 minutes, and enables detection of bacteria in a test sample that has as few as $10^5$ CFU/mL in as little as 1 hour, down to as little as 10 minutes.

A pre-culturing step refers to a step that increases the amount of bacteria in a test sample (when present), for example by incubating the test sample under culturing conditions. The pre-culturing step may involve any culturing methods known to a person skilled in the art and suitable for the bacteria that is to be detected. For example, the pre-culturing step may involve culturing the test sample in an appropriate growth medium at an appropriate temperature for an appropriate time. Examples of suitable growth media are well known to a person skilled in the art, and include Luria-Bertani medium, Brilliant green lactose bile (BGLB) broth, Lauryl tryptose (LST) broth, Lactose Broth, EC broth, Levine's eosin-methylene blue (L-EMB) agar, Tryptone (tryptophan) broth, MR-VP broth, Koser's citrate broth, Plate count agar (PCA). In embodiments of the invention that may be mentioned herein, the pre-culturing step may involve culturing at a temperature of 35° C. to 40° C., such as about 37° C. In embodiments of the invention that may be

TABLE 2

List of sorbents to remove pigments

| Material | Interferences | Example: Fatty acid removal by PSA[8] |
|---|---|---|
| $MgSO_4$ | removes excess water | |
| PSA | removes sugars, fatty acids, organic acids, and anthocyanine pigments | $R^1\diagdown\underset{\underset{H}{\overset{++}{N}}}{}\diagup R^2$ |
| C-18 | removes nonpolar interferences | |
| GCB | removes pigments, sterols, and nonpolar interferences | PSA |
| Florisil | removes polar interferences and concentrating pesticides, alcohols, aldehydes, amines, herbicides, PCBs, ketones, nitro compounds, organic acids, and phenols | + |
| Alumina | aldehydes, ketones, quinones, esters, lactones, and glycosides | [fatty acid structure with COOH group] |
| Octadecylsilane | removes lipids and waxes | |
| Zirconium dioxide-based sorbents | removes phospholipids, carboxylic acids and proteins | |
| Diatomaceous earth | removes organic and fatty acids, removes water, solid interferences | |

$\downarrow$ -H2O

Fatty acid $R\diagup\underset{\underset{H}{\overset{\overset{O}{\|}}{N}}}{}\diagup R^1$ Product
Amidoamine A pre-concentration step refers to a step that increases the concentration of bacteria in a test sample (when present), for example by removing excess aqueous solution from the test sample while retaining the bacteria. The pre-concentration step may involve isolating (e.g. pelleting) the bacteria and mentioned herein, the pre-culturing step may involve culturing for a time of from about 1 hour to about 12 hours, for example about 2 hours to about 9 hours, such as about 3 hours to about 7 hours. The use of a pre-culturing step enables bacteria to be detected from a test sample that is only very weakly contaminated, such as contamination as low as 1 CFU/mL in as little as 6 hours.

The methods of the invention, which may be generally referred to herein as the membrane protease-based method, have two major components: a peptide substrate for one or more proteases found on the outer membrane or surface of the bacteria, and a conjugated reporter polymer. The terms "outer membrane protease" and "surface protease" are herein used interchangeably.

The peptide substrate for one or more proteases found on the outer membrane of the bacteria (which may be referred to herein as "the peptide" or "the peptide substrate") is a peptide that can be cleaved by said one or more proteases under appropriate conditions. The peptide substrate is also a peptide that, when in aqueous solution with the conjugated reporter polymer, interacts (forms a complex) with the conjugated reporter polymer to induce a change in the structure (conformation) of the conjugated reporter polymer, where said change in structure causes a change in the optical absorption and/or colour and/or photoluminescence (e.g. fluorescence) of the conjugated reporter polymer. This is explained in more detail below. Given that the peptide substrate induces a detectable change in the conformation of the conjugated reporter polymer, the detection method does not require that the peptide itself comprises a fluorescent label. Thus, in embodiments of the invention that may be mentioned herein, the peptide substrate for one or more proteases found on the outer membrane of the bacteria does not comprise a fluorescent label.

In embodiments of the invention, the peptide substrate comprises two adjacent basic amino acid residues, wherein each of the basic amino acid residues is independently selected from the group consisting of Lysine, Arginine or Histidine. In some embodiments of the invention, the peptide substrate for one or more proteases found on the outer membrane of the bacteria comprises a cleavage site which comprises two adjacent arginine residues, where the peptide substrate is cleaved between the two arginine residues by the at least one outer membrane protease. In some embodiments of the invention, the peptide substrate for one or more proteases found on the outer membrane of the bacteria comprises a cleavage site selected from the group comprising or consisting of FRRV (SEQ ID NO: 1), FRRY (SEQ ID NO: 2), FRRA (SEQ ID NO: 3), YRRA (SEQ ID NO: 4) and ARRA (SEQ ID NO: 5).

In some embodiments of the invention, the peptide substrate has the following structure:

residues at the cleavage site are changed are also useful in the invention, and include LL37$_{FRRY}$: C L L G D F F R R Y K E K I G (SEQ ID NO: 8), LL37$_{FRRA}$: C L L G D F F R R A K E K I G (SEQ ID NO: 9), LL37$_{YRRA}$: C L L G D F Y R R A K E K I G (SEQ ID NO: 10), LL37$_{ARRA}$ C L L G D F A R R A K E K I G (SEQ ID NO: 11), and LL37$_{ARKA}$ C L L G D F A R K A K E K I G (SEQ ID NO: 12). The aforementioned sequences all include a cysteine residue at the start of the sequence. The cysteine residue may facilitate anchoring of the peptide on to a solid support. Variants of these peptides in which the cysteine residue is omitted also have activity against membrane proteases and are useful in the present invention and comprise or consist of the peptide sequences set forth in sequences L L G D F F R R V K E K I G (SEQ ID NO: 13), L L G D F F R R Y K E K I G (SEQ ID NO: 14), L L G D F F R R A K E K I G (SEQ ID NO: 15), L L G D F Y R R A K E K I G (SEQ ID NO: 16) and L L G D F A R R A K E K I G (SEQ ID NO: 17).

In some embodiments, the peptide substrate is specific for omptin protease on bacteria. It will be understood that the amino acid sequence of the peptide may be altered with a conservative substitution and retain the ability to be an effective substrate for a target outer membrane protease and retain the ability to induce a change in the conformation of the conjugated reporter polymer while intact (i.e. in the un-cleaved state). A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta- and gamma-branched side chains (e.g., threonine, valine, isoleucine) and aromatic side chains (e.g., tyrosine, phenylalanine, tryptophan, histidine). Thus, a predicted nonessential amino acid residue in a peptide substrate is preferably replaced with another amino acid residue from the same side chain family. Therefore, in some embodiments, the peptide substrate has at least 30%, at least 40%, at least 50%, at least 60%, at least 70%, at least 80%, at least 90%, or 100% sequence similarity with a peptide selected from the group consisting of cathelicidin

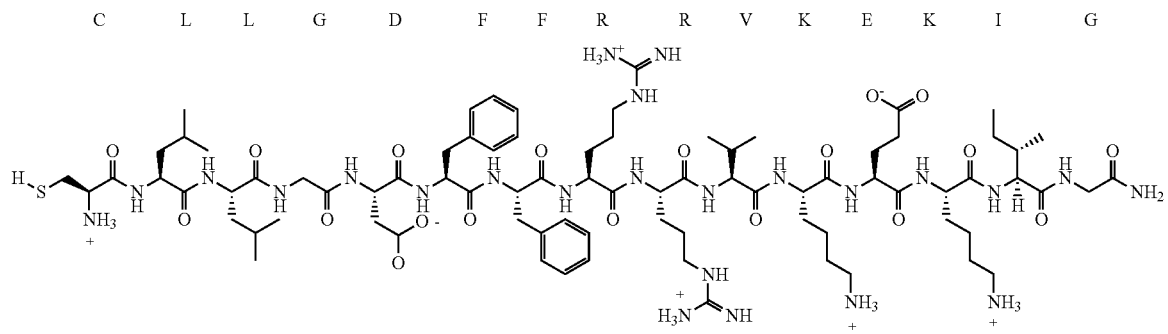

which corresponds to the amino acid sequence C L L G D F F R R V K E K I G (SEQ ID NO: 7) and is referred to herein as LL37$_{FRRY}$. Variants of LL37$_{FRRY}$ in which the LL37 (SEQ ID NO: 6), LL37$_{FRRV}$ C L L G D F F R R V K E K I G (SEQ ID NO: 7), LL37$_{FRRY}$ C L L G D F F R R Y K E K I G (SEQ ID NO: 8), LL37$_{FRRA}$ C L L G D F F R R A K E K I G (SEQ ID NO:9), LL37$_{YRRA}$ C L L G D F Y R R A K E K I G (SEQ ID NO: 10), LL37$_{ARRA}$ C L L G D F A R R A K E K I G (SEQ ID NO: 11), LL37$_{ARKA}$ C L L G D F A R K A K E K I G (SEQ ID NO: 12), L L G D F F R R V K E K I G (SEQ ID NO: 13), L L G D F F R R Y K E K I G (SEQ ID NO: 14), L L G D F F R R A K E K I G (SEQ ID NO: 15), L L G D F Y R R A K E K I G (SEQIDNO: 16) and L L G D F A R R A K E K I G (SEQ ID NO: 17), provided that the peptide substrate comprises a cleavage site which comprises two adjacent arginine residues and retains the ability to interact with and induce a change in the structure (conformation) of the conjugated reporter polymer.

As used herein the term "similarity" refers to a comparison to a reference sequence, whilst retaining a target protease cleavage site. The percent similarity between a reference sequence and a query sequence is determined by aligning the sequences so that the highest order match is obtained, and comparing the aligned amino acids. Using any sequence alignment tool, it is possible to calculate "similarity". One such example of a protein sequence alignment tool that performs 'pairwise global alignment' of any two protein/peptide sequences to calculate similarity, is EMBOSS-NEEDLE (EMBL-EBI).

In some embodiments the cleavage site is selected from the group consisting of FRRV (SEQ ID NO: 1), FRRY (SEQ ID NO: 2), FRRA (SEQ ID NO: 3), YRRA (SEQ ID NO: 4) and ARRA (SEQ ID NO: 5). In some embodiments the peptide substrate amino acid sequence is selected from the group consisting of SEQ ID NO: 6, SEQ ID NO: 7, SEQ ID NO: 8, SEQ ID NO: 9, SEQ ID NO: 10, SEQ ID NO: 11 and (SEQ ID NO: 12). Other peptides that are cleaved by outer membrane proteases, such as omptin proteases (e.g. OmpT) are listed in Table 3. Therefore, in some embodiments of the invention the peptide substrate may be selected from the peptides listed in Table 3, with amino acid sequences set forth in SEQ ID NO: 18 to SEQ ID NO: 46.

TABLE 3

List of antimicrobial peptides with omptin protease recognition sites

| NAME | SOURCE | SEQUENCE | SEQ ID NO. |
|---|---|---|---|
| Cecropin A | Hyalophora cecropia | KWKLFKKIEKVGQNIRDGIIKAG PAVAVVGQATQIAK | 18 |
| Cecropin P1 | Ascaris suum | SWLSKTAKKLENSAKKRISEGI AIAIQGGPR | 19 |
| CECD | Aedes aegypti | MNFTKLFAIV LLAALVLLGQ TEAGGLKKLG KKLEGAGKRV FKASEKALPV VVGIKAIGK | 20 |
| Papiliocin | Papilio xuthus | RWKIFKKIEKVGRNVRDGIIKA GPAVAVVGQAATVVK | 21 |
| Moricin | Bombyx mori | MNILKFFFVFIVAMSLVSCSTAA PAKIPIKAIKTVGKAVGKGLRAI NIASTANDVFNFLKPKKRKH | 22 |
| ceratotoxin A (CtxA) | Ceratitis capitata | SIGSALKKALPVAKKIGKIALPIA KAALPVAAGLVG | 23 |
| Melittin | Apis mellifera | GIGAVLKVLTTGLPALISWIKRK RQQ | 24 |
| Magainin 2, Cecropin A | Xenopus laevis | KWKLFKKIKFLHSAKKF IGKFLHSAKKFGKAFVGEIMNS | 25 |
| Dermaseptin | hyllomedusa sauvagei | ALWMTLLKKV LKAAAKALNA VLVGANA | 26 |
| Bombinin-H4 | Bombina variegata | IIGPVLGLVG SALGGLLKKI G | 27 |
| Brevinin-1 | Rana brevipoda porsa | FLPVLAG IAAKVVPALFCKITKKC | 28 |
| Abaecin | Apis mellifera | CAAFAYVPLP NVPQPGRRPF PTFPGQGPFN PKI | 29 |
| Indolicidin | Bos taurus | ILPWKWPWWPWRR | 30 |
| BACTENECIN 5 | Bovine neutrophils, Bos taurus | RFRPPIRRPPIRPPFYPPFRPPI RPPIFPPIRPPFRPPLGPFP | 31 |
| Heliocin | Heliothis virescens | QRFIHPTYRPPPQPRRPVIMRA | 32 |
| Chicken AvBD5 | Gallus gallus domestic | GLPQDCERRGGFCSHKSCPP GIGRIGLCSKEDFCCRSRWYS | 33 |
| Andersonin-C1 | Odorrana andersonii, China, Asia | TSRCIFYRRKKCS | 34 |

TABLE 3-continued

List of antimicrobial peptides with omptin protease recognition sites

| NAME | SOURCE | SEQUENCE | SEQ ID NO. |
|---|---|---|---|
| NRC-20 | Hippoglossus hippoglossus L | GFLGILFHGVHHGRKKALHMNSERRS | 35 |
| NCR247 | Medicago truncatula | RNGCIVDPRCPYQQCRRPLYCRRR | 36 |
| mBD-12 | Mus musculus | CRLGRGKCRRTCIESEKIAGWCKLNFFCCRERI | 37 |
| mBD-6 | Mus musculus | CMSYGGSCQRSCNGGFRLGGHCGHPKIRCCRRK | 38 |
| Hg-CATH | naked mole rat, Heterocephalus glaber | RRFRRTVGLSKFFRKARKKLGKGLQKIKNVLRKYLPRPQYAYA | 39 |
| Tur1B | Tursiopt truncatus | RRIPFWPPNWPGPWLPPWSPPDFRIPRILRKR | 40 |
| Tur1A | Tursiopt truncatus | RRIRFRPPYLPRPGRRPRFPPPFPIPRIPRIP | 41 |
| Tachyplesin I | hemocytes | KWCFRVCYRGICYRRCR | 42 |
| NEMURI | Drosophila melanogaster | DARARRIVRAGRRRGGRRGGRRGGRRSARKS | 43 |
| ModoCath6 | Monodelphis domestica | VRRSKRGIKVPSFVKKVLKDVVSESIS | 44 |
| Myticalin C6 | Mytilus galloprovincialis | RRRRRFRRVIRRIRLPKYLTINTE | 45 |
| mCRAMP | Mus musculus | GLLRKGGEKIGEKLKKIGQKIKNFFQKLVPQPEQ | 46 |

In some embodiments of the invention:
the bacteria is selected from the group comprising or consisting of *Escherichia coli, Salmonella enterica, Yersinia pestis* and *Shigella flexneri*;
the conjugated reporter polymer is polythiophene acetic acid (PTAA), Poly[3(potassium-6-hexanoate)thiophene-2,5-diyl] (PT6), Poly[3-(Potassium-4-butanoate)thiophene-2,5-diyl] (PT4), or any combination thereof; and
the peptide substrate has at least 30%, at least 40%, at least 50%, at least 60%, at least 70%, at least 80%, at least 90% or 100% sequence similarity with a peptide selected from the group comprising or consisting of cathelicidin LL37 (SEQ ID NO: 6), $LL37_{FRRV}$ C L L G D F F R R V K E K I G (SEQ ID NO: 7), $LL37_{FRRY}$ C L L G D F F R R Y K E K I G (SEQ ID NO: 8), $LL37_{FRRA}$ C L L G D F F R R A K E K I G (SEQ ID NO:9), $LL37_{YRRA}$ C L L G D F Y R R A K E K I G (SEQ ID NO:10), $LL37_{ARRA}$ C L L G D F A R R A K E K I G (SEQ ID NO: 11) and $LL37_{ARKA}$ C L L G D F A R K A K E K I G (SEQ ID NO: 12).

In a preferred embodiment of the invention:
the bacteria is *Escherichia coli*;
the conjugated reporter polymer is Poly[3(potassium-6-hexanoate)thiophene-2,5-diyl] (PT6); and
the peptide substrate has an amino acid sequence set forth in SEQ ID NO: 9 or SEQ ID NO: 10.

Another aspect of the invention provides an isolated peptide substrate as defined hereinabove. In some embodiments the isolated peptide substrate has at least 30%, at least 40%, at least 50%, at least 60%, at least 70%, at least 80%, at least 90% or 100% sequence similarity with a peptide selected from the group comprising or consisting of $LL37_{FRRV}$ (SEQ ID NO: 7), $LL37_{FRRY}$ (SEQ ID NO: 8), $LL37_{FRRA}$ (SEQ ID NO: 9), $LL37_{YRRA}$ (SEQ ID NO: 10), $LL37_{ARRA}$ (SEQ ID NO: 11) and $LL37_{ARKA}$ (SEQ ID NO: 12).

Another aspect of the invention provides use of a peptide substrate with a conjugated reporter polymer for the determination of the presence or absence of bacteria expressing at least one outer membrane protease in a test sample, wherein the peptide substrate is cleaved by said outer membrane protease and can no longer form a complex with and change the conformation of the conjugated reporter polymer.

The "conjugated reporter polymer" is a polymer which comprises a conjugated system that enables a change in optical absorption and/or colour and/or photoluminescence (e.g. fluorescence) when the conformation of the reporter polymer changes. As will be appreciated by a person skilled in the art, a change in conformation of a molecule comprising a conjugated system will influence the energy levels within the conjugated system as the degree of orbital overlap changes, thereby changing the optical absorption and photoluminescence of the conjugated reporter polymer. These changes in conformation can therefore be detected by analysing the optical absorption and/or photoluminescence of the conjugated reporter. For example, small changes in optical absorption may be detected with a spectrophotometer, while large changes in optical absorption will result in a colour change that is visible to the naked eye. Changes in photoluminescence may be changes in fluorescence, e.g. changes in fluorescence under visible light or UV light.

Changes in fluorescence under visible light are not typically visible with the naked eye and may be determined by measuring fluorescence intensity, for example with a TECAN Infinite® 200 PRO (Switzerland) or a mobile phone camera. Fluorescence intensity may be measured by exciting the conjugated reporter polymer and detecting emission over any appropriate wavelength range, for example excitation at 420 nm and detection of emission over 450-750 nm. A suitable threshold for determining change in fluorescence intensity is a 20% change in fluorescence intensity.

Changes in fluorescence under UV light typically result in emission of light in the visible spectrum. For example, under UV-A light, a conjugated polythiophene reporter polymer is colourless, but when complexed with a peptide, it emits visible light having a bright orange colour (in the case of PTAA) and a bright crimson red (in the case of PT6). These changes may therefore be determined by the naked eye or by a device such as a mobile phone camera. The digital images obtained with a mobile phone camera can be evaluated to yield quantitative information by using a set of post-processing algorithms such as RGB or RGB-ΔE as in Example 8.

with carboxylic acid groups, ester groups, or cyanate groups, thiocyante groups, nitrile groups, nitro groups, phosphate groups, sulphate groups, sulfonate groups, thiol groups, acid halide groups or halogenated groups. Polythiophenes are a class of molecules comprising multiple thiophene units, where each thiophene unit may be substituted. Particular polythiophene derivatives that may be used in embodiments of the invention mentioned herein include polythiophene acetic acid (PTAA), poly[3-(potassium-6-hexanoate)thiophene-2,5-diyl] (PT6), poly[3-(potassium-4-butanoate)thiophene-2,5-diyl] (PT4) and combinations thereof.

The structure of a segment of polythiophene acetic acid is provided below. The structures of PT6 and PT4 are analogous to that of polythiophene acetic acid, but with different substituents on the thiophene rings. While the polythiophene shown below comprises carboxylic acid groups on every thiophene ring, a person skilled in the art will understand that polymers having fewer functional groups, for example a carboxylic acid group on every third thiophene ring, will also provide the desired properties for complexing with peptides.

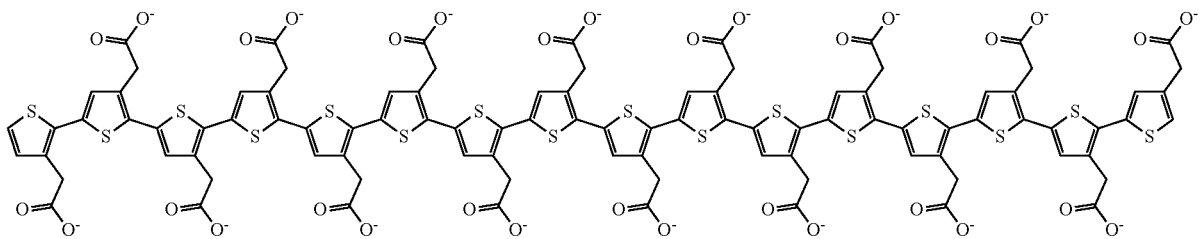 [SMILES: O=C([O-])Cc1csc(-c2sc(-c3sc(-c4sc(-c5sc(-c6sc(-c7sc(-c8sc(-c9sc(-c%10sc(-c%11sc(-c%12sc(-c%13sc(-c%14sc(-c%15sc(-c%16sccc%16CC(=O)[O-])cc%15CC(=O)[O-])cc%14CC(=O)[O-])cc%13CC(=O)[O-])cc%12CC(=O)[O-])cc%11CC(=O)[O-])cc%10CC(=O)[O-])cc9CC(=O)[O-])cc8CC(=O)[O-])cc7CC(=O)[O-])cc6CC(=O)[O-])cc5CC(=O)[O-])cc4CC(=O)[O-])cc3CC(=O)[O-])cc2CC(=O)[O-])c1]

As mentioned above, a change in the colour of the test sample may also be determined by the naked eye. For changes to be determined by the naked eye, the test sample could be viewed under normal visible light or under UV light, such that the colour or fluorescence emission change can be subjectively determined by the user's eyes and judgement.

Thus, in summary, the conjugated reporter polymer has the below properties.
a) It is able to physically interact with the peptide substrate.
b) The interaction with the peptide substrate results in a detectable change in conformation, such as a detectable optical change (absorption and/or photoluminescence).
c) The optical properties (or the change in optical properties) are different when interacting with the intact and cleaved peptide substrate i.e the conjugated reporter polymer is capable of distinguishing between the intact and cleaved peptide substrate.

In some embodiments of the invention the conjugated reporter polymer may be selected from the group consisting of a polythiophene; a poly(1,4-phenylene vinylene) (PPV); a poly(1,4-phenylene) (PPP); a polyfluorenes (PFO); a nitrogen-containing polymer such as polyquinoline, poly(2,5-pyridinevinylene), 1,3,4-oxadiazole, and poly(9-vinylcarbazole) (PVK); and a polypyrrole, In some embodiments of the invention, the conjugated reporter polymer may be a polythiophene, such as an anionic polythiophene, i.e. a polythiophene having substituents at one or both beta positions of the thiophene ring that can produce anionic groups in aqueous solution. Examples of anionic polythiophenes include polythiophenes substituted When the conjugated reporter polymer is a polythiophene, it may have a molecular weight of from about 5 to about 50 kDa, for example from about 10 to about 40 kDa, preferably from about 15 to about 35 kDa. Typically, the number of thiophene units in the polythiophene will be from about 80 to about 300, such as about 100 to about 250, for example about 150 to about 200.

In some embodiments of the invention, the conjugated reporter polymer is polythiophene acetic acid. In some embodiments of the invention, the conjugated reporter polymer is poly[3-(potassium-6-hexanoate)thiophene-2,5-diyl] (PT6).

Figure 2:
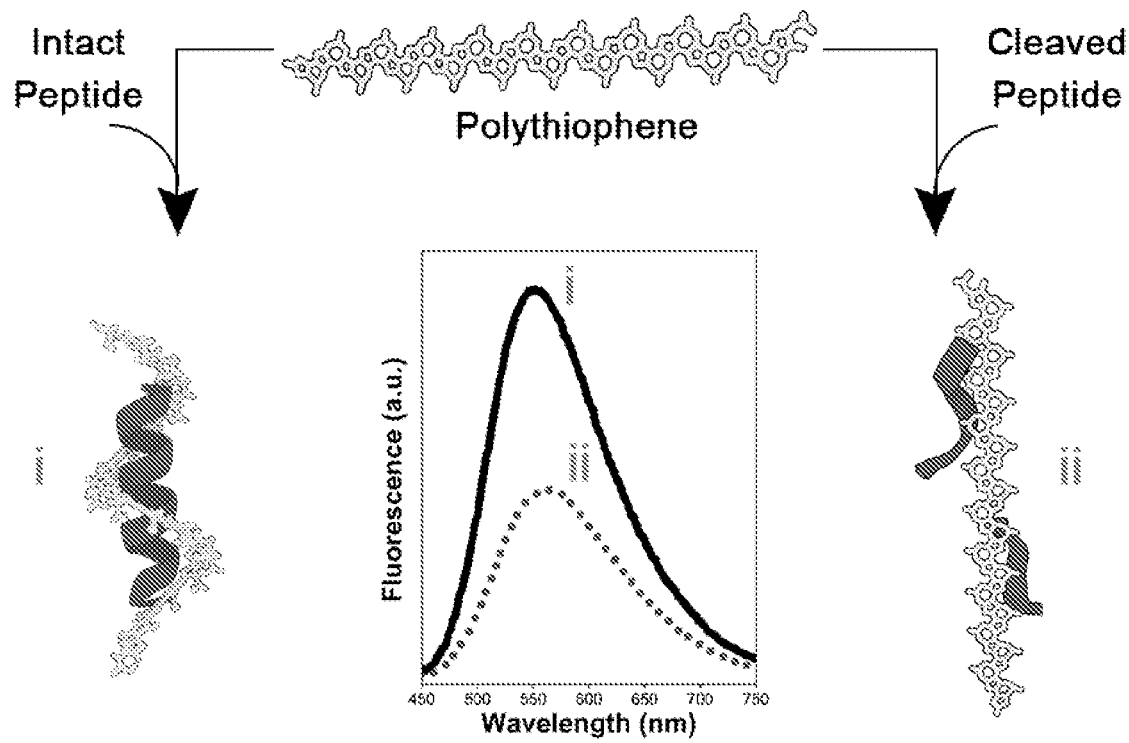
FIG. 2 provides a schematic illustration of the believed mechanism of the detection methods of the invention. Polythiophene usually adopts a linear conformation (top middle). (i) shows the result of mixing peptide (e.g.) $LL37_{FRRY}$ (SEQ ID NO: 7) and polythiophene (e.g. PTAA)—they interact electrostatically and both molecules adopt a helical conformation when mixed together. (ii) shows the result of peptide (e.g. $LL37_{FRRY}$ (SEQ ID NO: 7)) fragments (e.g. when cleaved by a bacterial surface protease such as OmpT) with polythiophene (e.g. PTAA)—they may interact but the fragments do not induce any significant structural changes in the polythiophene. The middle graph illustrates the fluorescence intensity changes in PTAA corresponding to the scenarios in (i) and (ii).

Anionic polythiophenes adopt a planar rod conformation in aqueous solution due to electrostatic repulsion forces between the anionic substituents (FIG. 2). Addition of a peptide having cationic groups to the solution results in electrostatic interactions between anionic groups in the polythiophene and the cationic groups in the peptide, causing a structural change in both of them (FIG. 2i). The peptide adopts a helical structure and causes the polythiophene backbone to adopt a nonplanar helix confirmation. As such, the peptide can be said to form a complex with the conjugated reporter polymer, where in this context "complex" means a molecular interaction which involves electrostatic and/or hydrogen bonding, where the conjugated reporter polymer adopts a conformation different to that adopted in aqueous solution in the absence of the peptide, such as a helical conformation. These conformational changes result in a change in optical absorption and/or colour and/or photoluminescence (e.g. fluorescence) of the conjugated reporter polymer (FIG. 2, solid line in graph).

However, if the peptide substrate is first cleaved by a membrane protease on the bacteria and then added to anionic polythiophene, there is negligible change in conformation. As such, there is a negligible change in optical absorption and/or colour and/or photoluminescence (e.g. fluorescence) (FIG. 2, dashed line in graph). This is because the cleaved fragments of the peptide do not cause the polythiophene backbone to adopt a nonplanar helix conformation (FIG. 2ii) and as such no substantial change in optical absorption and/or colour and/or photoluminescence (e.g. fluorescence) is observed. Thus, the change in colour of a polythiophene solution in the presence and absence of intact peptide can be used to determine the presence of a protease on the bacterial surface, and by extension, presence of the bacteria itself. Thus, in embodiments of the invention, the change or absence of a change in conformation of the conjugated reporter polymer may be determined by assessing the optical absorption and/or colour and/or photoluminescence (e.g. fluorescence) of the mixture containing the conjugated reporter polymer. However, a person skilled in the art will appreciate that other methods of detecting the conformation of the conjugated reporter polymer could also be used, for example Circular Dichroism, Infrared (IR) and Raman spectroscopy.

The methods of the invention may involve mixing the peptide with the conjugated reporter polymer before the peptide is exposed to the test sample, or after the peptide is exposed to the test sample. The sequence of these steps will influence whether a change in optical absorption and/or colour and/or photoluminescence (e.g. fluorescence) occurs.

When the peptide is exposed to the test sample before mixing with the conjugated reporter polymer, it will be cleaved into peptide fragments (assuming bacteria are present). This means that when the conjugated reporter polymer is added, there is no (or minimal) intact peptide present, and so the conformation of the conjugated reporter polymer does not change and it remains in the planar rod state. As such, if bacteria are present then this sequence of steps will not cause a change in optical absorption and/or colour and/or photoluminescence (e.g. fluorescence). If no bacteria are present then the mixing of conjugated reporter polymer with intact peptide will cause a change in optical absorption and/or colour and/or photoluminescence (e.g. fluorescence) as the conjugated reporter polymer undergoes a change in conformation.

It is necessary to ensure that the peptide and test sample are incubated for a sufficiently long time such that a substantial amount of the peptide is cleaved into fragments. Otherwise, upon mixing there will be a change in optical absorption and/or colour and/or photoluminescence (e.g. fluorescence) as the conjugated reporter polymer undergoes a change in conformation. This peptide-conjugated reporter polymer complex may not be able to act as a substrate for the target membrane protease, and as a result, the peptide might not be cleaved even in the presence of bacteria. This could result in a false negative, i.e. a conclusion that no bacteria are present, when in fact bacteria are present Thus, in embodiments of the invention in which the peptide and test sample are mixed before the conjugated reporter polymer is added, the peptide and test sample may be incubated or left for a predetermined period of time that is sufficient for substantially all of (e.g. at least 80%, at least 90%, or at least 95%) the peptide to be cleaved if bacteria are present above a minimum concentration (e.g. above $10^3$ CFU/mL, such as above $10^4$ CFU/mL, for example above $10^5$ CFU/mL). The predetermined period of time may depend on the peptide and conjugated reporter polymer used, and in general may be from about 1 minute to about 2 hours, for example from about 15 minutes to about 1.5 hours, such as from about 30 minutes to about 1 hour. As will be appreciated by a person skilled in the art, minimum concentration and predetermined period of time may depend on the bacteria to be detected.

The optical absorption and/or colour and/or photoluminescence (e.g. fluorescence) of a test sample after exposure to the peptide substrate and conjugated reporter polymer may be compared with a control. As used herein, a "control" is an optical absorption and/or colour and/or photoluminescence (e.g. fluorescence) value against which the optical absorption and/or colour and/or photoluminescence (e.g. fluorescence) of the test sample can be compared to confirm whether or not bacteria is present in the test sample and/or provide a level of quantitation of bacteria in the test sample. The control may be derived from the fluorescence intensity or colour of a sample that is known to be free of bacteria, where the steps of the method of the invention are performed on the control sample and the optical absorption and/or colour and/or photoluminescence (e.g. fluorescence) of the control sample is obtained. The control may alternatively be derived from the optical absorption and/or colour and/or photoluminescence (e.g. fluorescence) of a solution of the conjugated reporter polymer, or of a solution of the conjugated reporter polymer and peptide substrate. The control may also be a known optical absorption and/or colour and/or photoluminescence (e.g. fluorescence) obtained from a literature source or previously performed test. This type of control may be particularly appropriate for cheap portable testing kits where the choice of conjugated reporter polymer results in a significant colour change visible to the naked eye.

The nature of the control used will influence whether an optical absorption and/or colour or photoluminescence (e.g. fluorescence) value that is the same as/different to a control indicates the presence or absence of bacteria. Various combinations are set out in Table 4 below.

TABLE 4

Result of comparison with control

| | Result (e.g. fluorescence intensity/colour) | |
|---|---|---|
| Control type | Same as control | Different to control |
| Value derived from a solution known to be free of bacteria, to which the steps of the method are applied | Absence of bacteria | Presence of bacteria |
| Value derived from a solution of conjugated reporter polymer | Presence of bacteria | Absence of bacteria |
| Value derived from a solution of conjugated reporter polymer and peptide substrate | Absence of bacteria | Presence of bacteria |
| Known (e.g. literature or previous test result) fluorescence intensity or colour value for conjugated reporter polymer in absence of peptide substrate | Presence of bacteria | Absence of bacteria |

TABLE 4-continued

Result of comparison with control

| Control type | Result (e.g. fluorescence intensity/colour) | |
|---|---|---|
| | Same as control | Different to control |
| Known (e.g. literature or previous test result) fluorescence intensity or colour value for conjugated reporter polymer-peptide substrate complex | Absence of bacteria | Presence of bacteria |

The conjugated reporter polymer may be provided on a solid support. Thus, the invention also provides a biosensor to detect the presence or absence of bacteria in a test sample, said biosensor comprising a solid support and a conjugated reporter polymer (e.g. a conjugated polythiophene reporter polymer) that changes conformation in the presence of intact peptide substrate specific for an outer membrane protease expressed by said bacteria, said conjugated reporter polymer attached to said solid support. As will be appreciated by a person skilled in the art, the conjugated reporter polymer will be connected to the solid support by a linker moiety. The linker moiety will be sufficiently long and flexible, and sufficiently sterically unhindered, such that it does not prevent the change in conformation of the conjugated reporter polymer and the formation of a complex with the peptide substrate. The bacteria, membrane protease, conjugated reporter polymer and peptide substrate may be as defined herein in relation to any embodiment of the invention.

The detection methods of the invention can be developed into an easy-to-use, rapid, and inexpensive kit for detection of bacterial pathogens in food and water samples. Such kits would have wide application in developing and resource-limited nations to assess drinking water quality. As such, the invention provides a kit for screening a test sample for the presence of at least one outer membrane protease indicative of bacteria, comprising a peptide substrate and a conjugated reporter polymer (e.g. a conjugated polythiophene reporter polymer), wherein intact peptide substrate binds to and alters the conformation of a conjugated reporter polymer. The bacteria, membrane protease, conjugated reporter polymer and peptide substrate may be as defined herein in relation to any embodiment of the invention.

In addition to developing assay kits for detection and distinguishing bacterial pathogens in water and food, the detection methods of the invention may be used to detect the presence of bacteria in a clinical setting. In some embodiments of the invention, the test sample is a sample isolated from a patient. For example, the E. coli strain J96 is commonly implicated in urinary tract infections. Thus, in some embodiments of the invention, the test sample may be a urine sample. In a particular embodiment, the invention can be used in the detection of a urinary tract infection caused by E. coli, by performing the method on a urine sample. This approach has following advantages compared to existing urine testing methods:

i) It is faster, easy to use and more sensitive compared to other commercially available kits.

ii) The method does not involve PCR or cell culturing, meaning that it can be performed outside of the laboratory setting and without highly trained personnel, thereby reducing costs involved.

iii) A multiplexed sensing platform for detecting and distinguishing multiple bacterial pathogens can be developed by providing enzyme specific peptides.

By providing information on bacterial contamination in relatively short time, the membrane protease-based method for detection of bacterial pathogens can help control the spread of infections. There are many areas of application for such a product. When sold in the form of home-use kits, it can help in monitoring bacterial contamination in drinking water, or for testing pool water for contamination. Regulatory bodies could utilise the method for periodic water testing. Since water is distributed using central distribution system in urban areas and through common water source in rural area, water borne infections can spread very fast if not detected in time. Therefore, by using bacterial assay kits that are fast and simple to use, we can control the spread of waterborne infections, reducing the casualties and financial expenses incurred on the treatment procedures. The membrane protease-based method can be developed into easy to use bacterial assay kits, which provide results much faster than currently available kits. Therefore, the invention provides large improvements in time for detection, as well as being easy to use and cost effective.

The invention is illustrated by the below Examples, which are not to be construed as limitative.

EXAMPLES

Materials

Poly (thiophene-3-acetic acid)-PTAA, an anionic PT, was synthesised by oxidative polymerisation of its monomer as described in B. Kim, L. Chen, J. Gong, Y. Osada, *Macromolecules* 32, 3964-3969 (1999).

Monobasic sodium phosphate, dibasic sodium phosphate, N-Dodecyl-N,N-dimethyl-1-ammonio-3-propane sulphonate ($DodMe_2NPrSO_3$), and Bis-tris were purchased from Sigma Aldrich (Singapore).

Luria-Bertani (LB) media was purchased from Becton, Dickinson and Company (Singapore).

Peptides mentioned in Table 5 were purchased as a lyophilized powder and certified >95% purity from GL BIOCHEM (SHANGHAI) LTD, China. The peptides were amidated at the C terminal.

Transparent, flat bottom 96 well plates were purchased from Corning® (New York, USA). E. coli BL21 and Lemo21(DE3) were purchased from New England Biolabs Pte Ltd (Singapore). Lemo21(DE3) cells were transformed with pET-28a plasmid carrying OmpT gene under a T7 promoter whose expression was induced by the addition of IPTG.

E. coli K12 ATCC® 700926™ and E. coli J96 ATCC® 700336™ were purchased from ATCC (USA) and supplied by Bio-REV Pte Ltd (Singapore).

Ultrafree®—MC centrifuge device 0.2 µm PTFE membrane were purchased from Merck Millipore (Singapore).

Abbreviations

PT: polythiophene

PTAA: polythiophene acetic acid

PT6: poly[3(potassium-6-hexanoate)thiophene-2,5-diyl]

CD: circular dichroism

```
LL37: peptide sequence
                                            (SEQ ID NO: 6)
LLGDFFRKSK-EKIGKEFKRI-VQRIKDFLRN-LVPRTES LL37_FRRV: peptide sequence
                                            (SEQ ID NO: 7)
C L L G D F F R R V K E K I G frag1LL37_FRRV: peptide sequence
                                            (SEQ ID NO: 47)
C L L G D F F R frag2LL37_FRRV: peptide sequence
                                            (SEQ ID NO: 48)
R V K E K I G LL37_FRRY: peptide sequence
                                            (SEQ ID NO: 8)
C L L G D F F R R Y K E K I G LL37_FRRA: peptide sequence
                                            (SEQ ID NO: 9)
C L L G D F F R R A K E K I G LL37_YRRA: peptide sequence
                                            (SEQ ID NO: 10)
C L L G D F Y R R A K E K I G LL37_ARRA: peptide sequence
                                            (SEQ ID NO: 11)
C L L G D F A R R A K E K I G
```

Screening of Peptides

A proteomic approach and high throughput screening technique (Self-Assembled Monolayers for Matrix-Assisted Laser Desorption/Ionization MS) was used to identify suitable peptides that are cleaved by omptin proteases. A peptide array was designed based on the best known peptide by modifying the amino acids at cleavage site and in the vicinity with 19 amino acids. SAMDI-MS was used to screen the peptide array. Using this technique, a short peptide substrate ($LL37_{FRRV}$) composed of 15 amino acids specific for OmpT was identified which was 400 times better then original peptide. This sequence was derived from a naturally occurring cationic antimicrobial peptide of the cathelicidin family, LL37, produced by the human body.

Example 1

Circular Dichroism Measurements of PTAA, $LL37_{FRRV}$ and Fragments of $LL37_{FRRV}$ The following samples were prepared: (1) PTAA, (2) $LL37_{FRRV}$, (3) PTAA mixed with $LL37_{FRRV}$ (SEQ ID NO: 7), (4) OmpT treated $LL37_{FRRV}$, and (5) OmpT treated $LL37_{FRRV}$ mixed with PTAA.

Final concentrations of PTAA, $LL37_{FRRV}$ (SEQ ID NO: 7), and OmpT were 10 μg/mL, 50 μM, and 1.4 μg/mL respectively.

A high precision cell made of Quartz SUPRASIL from Hellma-Analytics with 10 mm pathlength was used to record the CD spectra. Samples were scanned from 500-190 nm using an AVIV 420 CD spectrophotometer (Lakewood, NJ, USA) with a step size of 0.5 nm. The obtained data was processed in Origin 9.0.

Polythiophenes are known to show split-type induced CD (ICD) in the π-π* transition region (320-500 nm) [Nilsson, K. P. R. Olsson, J. D. M. Konradsson, P. Inganäs, O. Macromolecules 37, 6316-6321 (2004); Yashima, E. Matsushima, T. Okamoto, Y. J. Am. Chem. Soc. 119, 6345-6353 (1997)]. CD spectra of PTAA in the pH 8 reaction buffer suggests PTAA is optically inactive as it does not exhibit any characteristic ICD pattern in the π-π* transition region (FIG. 10 solid black). Taken together, the absence of CD signals and an absorption maximum at 450 nm suggests that PTAA backbone adopts a planar achiral conformation in the pH 8 reaction buffer (FIG. 10 and FIG. 9A solid black). However, upon adding $LL37_{FRRY}$ (SEQ ID NO: 7), split-type ICDs in the π-π* transition region was observed (FIG. 10 dotted grey). The blue shift in absorption, increase in fluorescence intensity of PTAA with the addition of $LL37_{FRRY}$ (SEQ ID NO: 7) (FIGS. 9A, 10B), and ICD (FIG. 10A, dotted grey) for PTAA-$LL37_{FRRY}$ all indicate that it is a result of main-chain chirality such as a predominantly helical structure induced in PTAA backbone due to the interaction between PTAA and $LL37_{FRRY}$ (SEQ ID NO: 7). The shape and sign of the ICD pattern for PTAA is characteristic of a left-handed helical form of PTs [Goto, H. Yokochi, Y. Yashima, E. Chem. Commun. 48, 3291 (2012)].

In the absence of PTAA, the CD spectra of $LL37_{FRRY}$ (SEQ ID NO: 7) and the two shorter peptide fragments resulting from OmpT cleavage of $LL37_{FRRY}$ (SEQ ID NO: 7) exhibit no defined conformation (FIG. 10A dashed black and dash-dotted grey). However, in the presence of PTAA, $LL37_{FRRY}$ (SEQ ID NO: 7) adopts a helical conformation as interpreted from the CD signal in the 190-240 nm range (FIG. 10A dotted grey). This conformational change is also reminiscent of the full length LL37 (SEQ ID NO: 6) which is known to adopt helical structures when exposed to lipid membranes. While both PTAA and the intact $LL37_{FRRY}$ (SEQ ID NO: 7) adopt helical conformations when mixed together, there was no change in conformation observed for PTAA and an equimolar mixture of $_{frag1}LL37_{FRRV}$ (SEQ ID NO: 47) and $_{frag2}LL37_{FRRV}$ (SEQ ID NO: 48) which are identical to the two shorter fragments produced by OmpT when it cleaves $LL37_{FRRY}$ (SEQ ID NO: 7) (FIG. 10A dash-dotted black).

To summarise, the results show that:

PTAA adopts a linear planar conjugated structure in the absence of $LL37_{FRRY}$ (SEQ ID NO: 7).

$LL37_{FRRV}$ (SEQ ID NO: 7) does not adopt a defined conformation in the absence of PTAA.

When PTAA and $LL37_{FRRY}$ (SEQ ID NO: 7) are mixed, they both adopt a helical structure, disrupting the conjugation in PTAA and resulting in a change in optical absorption and/or colour optical and photoluminescence (e.g. fluorescence).

The two fragments of $LL37_{FRRY}$ (SEQ ID NO: 7) produced by OmpT cleavage do not cause PTAA to adopt a helical structure, leading to no change in optical absorption and/or colour and photoluminescence (e.g. fluorescence).

Example 2

PTAA-Peptide Fluorescence and Optical Absorption Measurements

Stock solutions of PTAA were prepared at a concentration of 0.1 mg/mL in a reaction buffer containing 20 mM sodium phosphate buffer whose pH was adjusted to 8 using HCl. $LL37_{FRRY}$ peptide stock solutions were prepared in the reaction buffer at a concentration of 500 μM. To study the effects of $LL37_{FRRY}$ on PTAA's optical absorption and fluorescence intensity, different concentrations of $LL37_{FRRY}$ (150-6.25 μM) were added to PTAA (10 μg/mL). All PTAA and $LL37_{FRRY}$ mixing were carried out in the reaction buffer. All optical absorption and fluorescence measurements were carried out on 100 μL samples in a flat bottom 96 well plate using a TECAN Infinite® 200 PRO(Switzerland). Optical absorption measurements were collected from 330-650 nm.

Fluorescence scans were collected by exciting the samples at 420 nm and their emission spectrum recorded from 450-750 nm. Since the fluorescence intensity increase for PTAA saturated at 50 µM of LL37$_{FRRV}$, this peptide concentration was chosen for all further experiments. Stock solutions of $_{frag1}$LL37$_{FRRV}$ (SEQ ID NO: 47) and $_{frag2}$LL37$_{FRRV}$ (SEQ ID NO: 48), the two synthetic peptide fragments of LL37$_{FRRY}$ that are identical to the two cleaved fragments obtained when OmpT cleaves LL37$_{FRRY}$, were prepared in the reaction buffer at a concentration of 1 mM (Table 5). To understand the effect of intact and cleaved fragments on the fluorescence intensity and optical absorption of PTAA, LL37$_{FRRV}$, $_{frag1}$LL37$_{FRRV}$ (SEQ ID NO: 47) and $_{frag2}$LL37$_{FRRV}$ (SEQ ID NO: 48) were added in different ratios (10:0, 8:2, 6:4, 4:6, 2:8, 0:10) while keeping the total peptide concentration at 50 µM. The fluorescence intensity and optical absorption spectra were measured as mentioned before.

TABLE 5

Peptide LL37$_{FRRV}$ and its fragments

| Peptide | Sequence | SEQ ID NO. |
|---|---|---|
| LL37$_{FRRV}$ | CLLGDFFRRVKEKIG | 7 |
| $_{frag1}$LL37$_{FRRV}$ | CLLGDFFR | 47 |
| $_{frag2}$LL37$_{FRRV}$ | RVKEKIG | 48 |

Besides mixing short synthetic peptide fragments of LL37$_{FRRY}$, 50 µM of the intact LL37$_{FRRY}$ was treated with varying concentrations (42, 8.4, 2.8, 1.68, 0.84 nM) of recombinant OmpT that was reconstituted in detergent micelles. This OmpT was obtained by overexpressing the protein in *E. coli* BL21 as inclusion bodies using a protocol reported earlier [Kramer, R. A. Zandwijken, D. Egmond, M. R. Dekker, N. *Eur. J. Biochem.* 267, 885-893 (2000)]. Briefly, the inclusion bodies were unfolded and solubilized using 8 M urea and subsequently refolded in the presence of DodMe$_2$NPrSO$_3$, a zwitterionic detergent. The refolded OmpT was purified and stored at 4° C. for further use. A 100 µL reaction containing 50 µM of the intact LL37$_{FRRY}$ was incubated at 37° C. for 2 hours with 500 RPM shaking. To this 100 µL reaction mixture, 10 µL of PTAA stock solution (0.1 mg/mL) was added. Fluorescence measurements and absorbance scans were collected as mentioned before. The raw fluorescence (F.) intensity scans are either plotted as is or reported as % fluorescence increase. The following formula was applied to convert fluorescence intensity (a.u.) to % fluorescence increase:

$$\% \text{ F. increase} = \left( \frac{F_{PTAA+Peptide} - F_{PTAA}}{F_{PTAA}} \right) \times 100\%$$

The % fluorescence was normalized and calculated based on the following formula:

$$\% F = \left( \frac{F_{Sample} - F_{PTAA}}{F_{PTAA+Peptide} - F_{PTAA}} \right) \times 100\%$$

Figure 9:
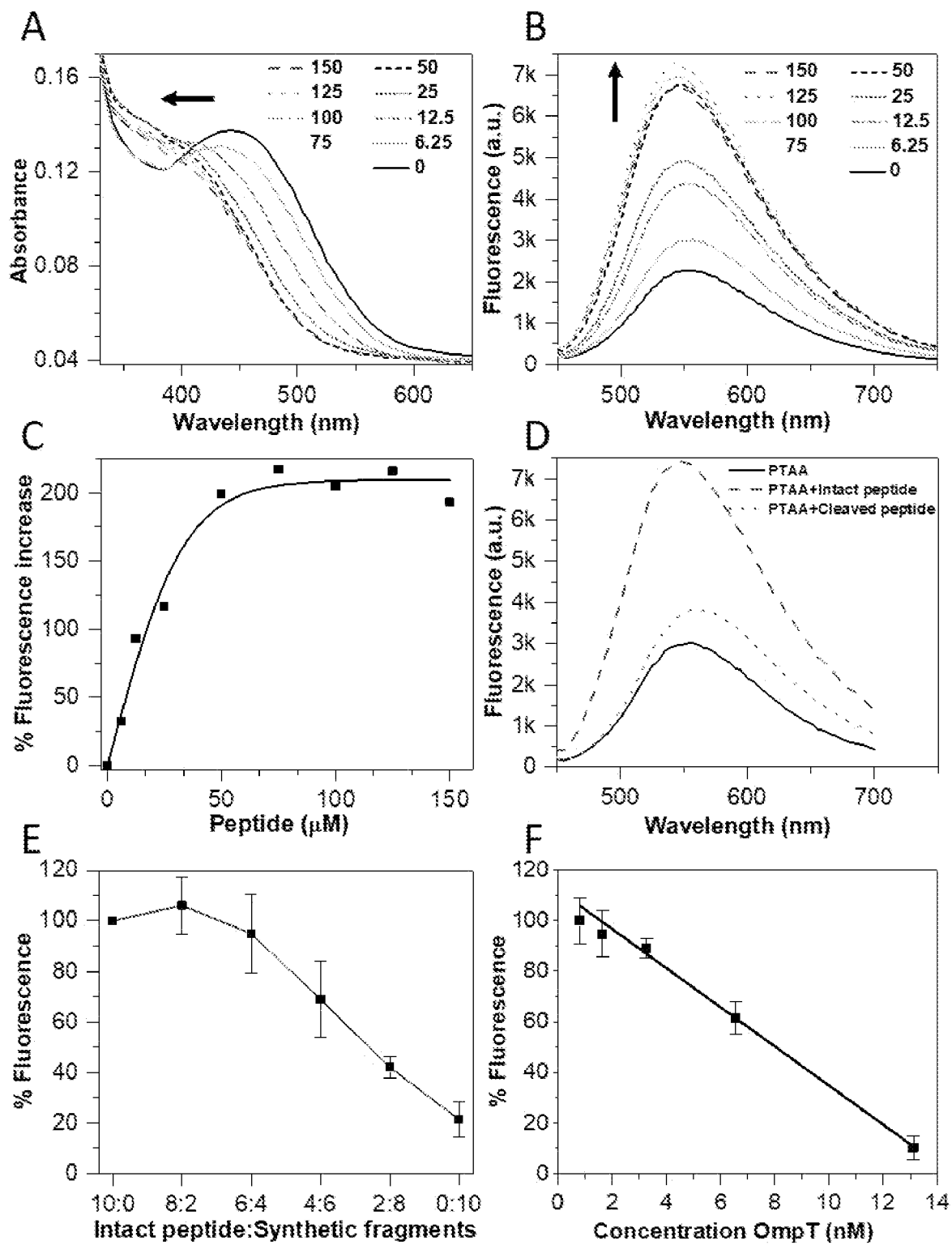
FIG. 9 depicts optical absorption and fluorescence spectra of PTAA and $LL37_{FRRY}$ (SEQ ID NO: 7). (A): Absorption spectra of PTAA at different concentrations of $LL37_{FRRY}$ (SEQ ID NO: 7) (µM) exhibiting a blue shift that corresponds to increasing $LL37_{FRRY}$ (SEQ ID NO: 7) concentrations. The arrow indicates direction of shift. (B): Fluorescence emission spectra of PTAA exhibiting an increase in fluorescence intensity that corresponds to increasing $LL37_{FRRY}$ (SEQ ID NO: 7) concentrations (µM). The arrow indicates direction of change. (C): Increase in fluorescence intensity of PTAA at 550 nm when mixed with increasing concentrations of intact $LL37_{FRRY}$ (SEQ ID NO: 7). (D): Comparison of fluorescence spectra of PTAA (solid), and when PTAA is mixed with either the intact $LL37_{FRRY}$ (SEQ ID NO: 7) (dashed) or the cleaved fragments of $LL37_{FRRY}$ (SEQ ID NO: 7) resulting from prior exposure to OmpT (dotted). (E): Fluorescence intensity of PTAA at 550 nm when mixed with different ratios of intact and cleaved $LL37_{FRRY}$ (SEQ ID NO: 7). (F): Change in fluorescence intensity of PTAA when mixed with 50 µM $LL37_{FRRY}$ (SEQ ID NO: 7) previously treated with varying concentrations of OmpT for 2 h. The data in C, E & F were normalised for the highest PTAA fluorescence intensity at 550 nm. Normalised data in C & E are plotted as % fluorescence increase. Error bars indicate standard error of the mean r n=2.
Figure 10:
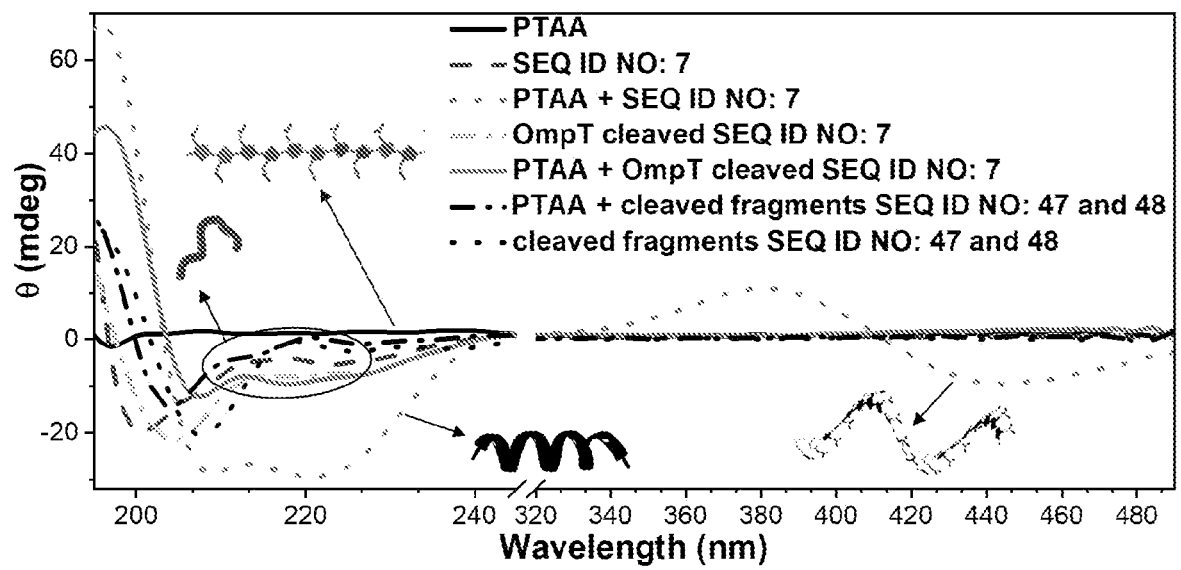
FIG. 10 depicts circular dichroism measurements of PTAA, $LL37_{FRRY}$ (SEQ ID NO: 7), PTAA-$LL37_{FRRY}$ complex, OmpT cleaved $LL37_{FRRY}$ (SEQ ID NO: 7), PTAA mixed with OmpT cleaved $LL37_{FRRY}$ (SEQ ID NO: 7) and PTAA mixed with synthetic cleaved $LL37_{FRRY}$ (SEQ ID NO: 7) fragments.

Results are shown in FIG. 9.

PTAA in an aqueous buffer has an absorption maximum at 450 nm and upon adding LL37$_{FRRY}$ exhibits a blue shift that corresponds to a colour change from orange to yellow (FIG. 9A). This blue shift increases linearly with increasing peptide concentration until it saturates at 50 µM of the added peptide (FIG. 9A). At sufficiently high PTAA and peptide concentrations, this colour change can be detected with the naked eye. When excited at 420 nm, PTAA exhibits a fluorescence emission maximum at 550 nm (FIG. 9B solid black).

Figure 12:
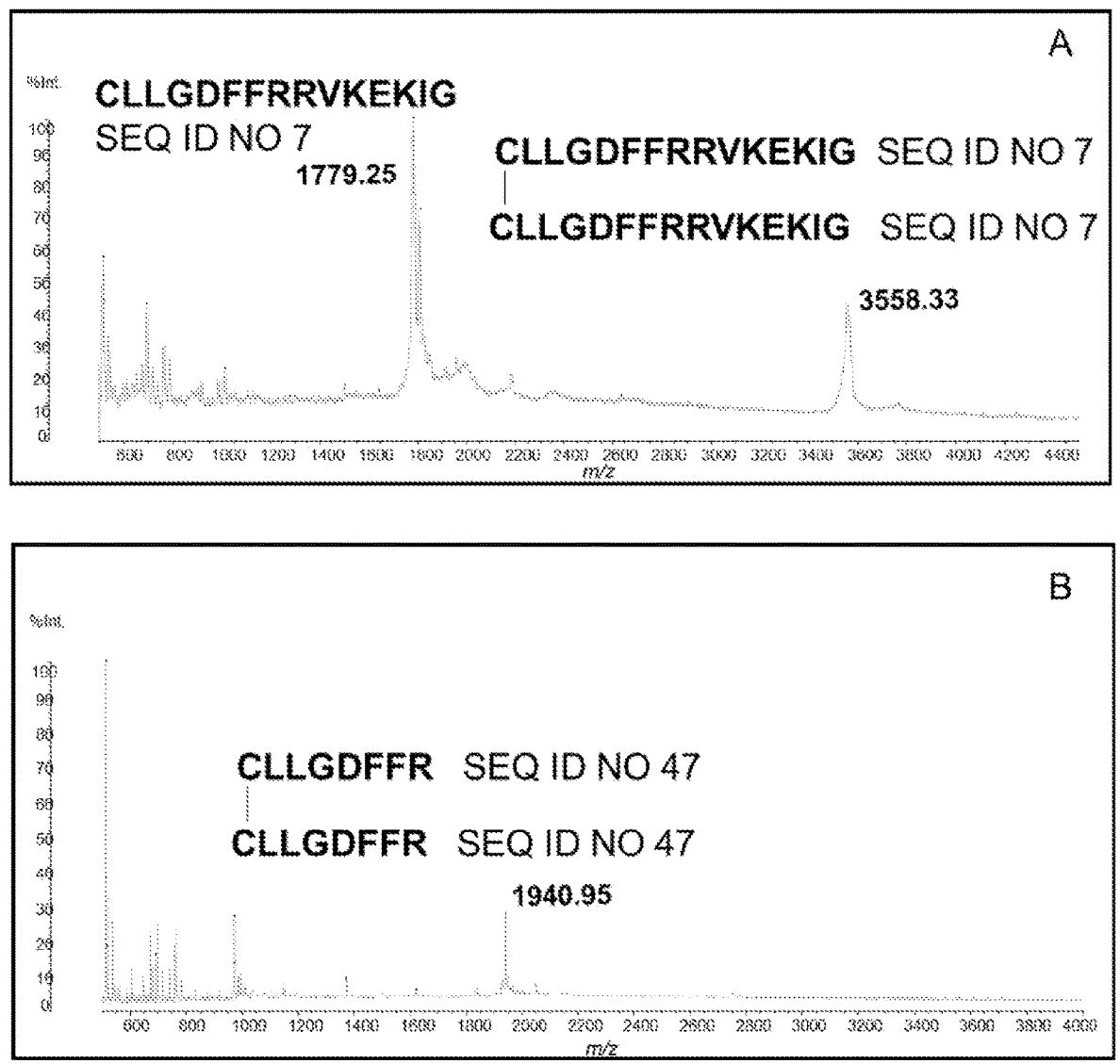
FIG. 12 shows MALDI-TOF spectra for intact LL37$_{FRRY}$ (SEQ ID NO: 7) and cleaved fragment frag1LL37$_{FRRY}$ (SEQ ID NO: 47): (A): Intact LL37$_{FRRY}$ peptide (MW of 1780.19 Da) (SEQ ID NO: 7) shows a m/z peaks at 1779.25 (monomer) and 3358.33 (dimer formed because of thiol bonds). (B): Cleaved fragment $_{frag1}$LL37$_{FRRV}$ (SEQ ID NO: 47) shows a peak at 1940.95 which corresponds to the dimer of this cleaved fragment.

Similar to the blue shift described above, upon adding LL37$_{FRRY}$, the fluorescence intensity at 550 nm increases linearly with increasing peptide concentration until it saturates at 50 µM of the added peptide (FIGS. 9B & C). At the peptide's highest concentration, the overall increase in PTAA's fluorescence intensity is close to 200% (FIG. 9C). Separately, when LL37$_{FRRV}$ was treated with OmpT reconstituted into detergent micelles, it was cleaved at the dibasic site (—R$_8$-R$_9$—) to yield two short fragments of eight and seven residues (Table 5) and was confirmed by MALDI-TOF analysis with peak at 1779.5 for the intact peptide (FIG. 12A) and a peak at 1940.95 m/z which corresponds to the dimer of one of the cleaved fragment (FIG. 12B). When these peptide fragments were mixed with PTAA, it did not result in a significant increase in fluorescence intensity, and the increase was no more than 20% at best (FIG. 9D dotted grey). As an additional control, two short peptides were synthesized ($_{frag1}$LL37$_{FRRV}$ (SEQ ID NO: 47) and $_{frag2}$37$_{FRRV}$ (SEQ ID NO: 48)) that were identical to the two cleaved fragments obtained when OmpT cleaves LL37$_{FRRY}$ (Table 5). The two short synthetic fragments were combined with intact LL37$_{FRRY}$ in different ratios and subsequently mixed with PTAA. The results indicate that the shorter peptides do not contribute much to the fluorescence intensity, but when mixed with increasing proportions of the longer intact peptide, showed an enhancement in the overall fluorescence intensity (FIG. 9E). This clearly demonstrates that only the intact LL37$_{FRRY}$ contributes to the enhancement in fluorescence intensity while the shorter peptide fragments resulting from OmpT's enzymatic activity do not.

The rate at which LL37$_{FRRY}$ is cleaved into shorter fragments is a function of OmpT concentration and time. Hence, with increasing OmpT concentrations a larger proportion of LL37$_{FRRY}$ is cleaved into shorter fragments. This process was monitored by measuring end-point fluorescence intensity of PTAA that was mixed with 50 µM of LL37$_{FRRY}$ exposed for 2 hours to varying concentrations of OmpT (0.84-42 nM). There was an overall decrease in PTAA's fluorescence intensity that correlated with increasing OmpT concentration (FIG. 9F). At the highest OmpT concentration (42 nM), PTAA's fluorescence intensity was ~175% less than its fluorescence intensity with LL37$_{FRRY}$ in the absence of OmpT, suggesting that almost all of the LL37$_{FRRY}$ was cleaved into shorter fragments (FIG. 9F).

PTAA's initial absorbance maximum at 450 nm represents planarization of the polymer backbone [Nilsson, K. P. R. Andersson, M. R. Inganas, O. *J. Phys. Condens. Matter* 14, 10011-10020 (2002); Nilsson, K. P. R. Rydberg, J. Baltzer, L. Inganas, O. *Proc. Natl. Acad. Sci. U.S.A.* 101, 11197-11202 (2004); Nilsson, K. P. R. Rydberg, J. Baltzer, L. Inganas, O. *Proc. Natl. Acad. Sci.* 100, 10170-10174 (2003)]. The deprotonation of the carboxylic group on PTAA's side chain when solubilized in the pH 8 reaction buffer induces planarization and stretching of the polymer backbone in order to reduce the electrostatic repulsion between the side groups. The PTAA planar chains could also be grouped together showing non-radiative de-excitation because of the contact between the polymer chains which further contributes to lower fluorescence. The negatively charged carboxylic acid groups of PTAA side chain are expected to interact electrostatically with the positively charged amine groups on the side chains of arginine (R) and lysine (K) [Selegård, R. Rouhbakhsh, Z. Shirani, H. Johansson, L. B. G. Norman, P. Linares, M. Aili, D. Nilsson, K. P. R. *Macromolecules* 50, 7102-7110 (2017)].

Since LL37$_{FRRY}$ carries two arginines and two lysines in its sequence, these electrostatic interactions will force the polymer backbone to adopt a non-planar conformation, thereby decreasing the effective conjugation length of the polymer backbone. This conformational change in the PTAA backbone chain also alters the optical properties-absorption and emission spectra of PTAA, which was observed when LL37$_{FRRY}$ was mixed with PTAA (FIGS. 9A & B). The PTAA and LL37$_{FRRY}$ complex results in the separation of the PTAA polymer chains and induces a chirality in the PTAA backbone that was also confirmed by the circular dichroism (CD) measurements in Example 1.

Example 3

*E. coli* Detection in Water

A membrane protease-based (OmpT-PTAA) method of the invention was investigated using water samples comprising *E. coli*. All wild type *E. coli* strains express the omptin protease OmpT. Polythiophene acetic acid (PTAA) was used as a reporter polymer and LL37$_{FRRY}$ was used as a peptide that targets OmpT.

Four different strains of *E. coli* (Table 6) and different concentrations ($10^8$-$10^6$ CFU/mL) of each strain were used for water sample testing. *E. coli* BL21 cells act as negative control since they do not have OmpT on their outer surface. *E. coli* LEMO cells have overexpressed OmpT on the surface while K12 and J96 are natural strains of *E. coli* with OmpT expressed on the outer membrane surface.

TABLE 6

Strains of *E. coli* used for sensing

| | *E. coli* Strain | Presence of OmpT on surface |
|---|---|---|
| Negative Control | BL21 | Negative |
| Positive Control-2 | LEMO | Overexpressed |
| Tested for indicating possible faecal contamination | K12 | Positive |
| Urinary tract infection | J96 | Positive |

Figure 3:
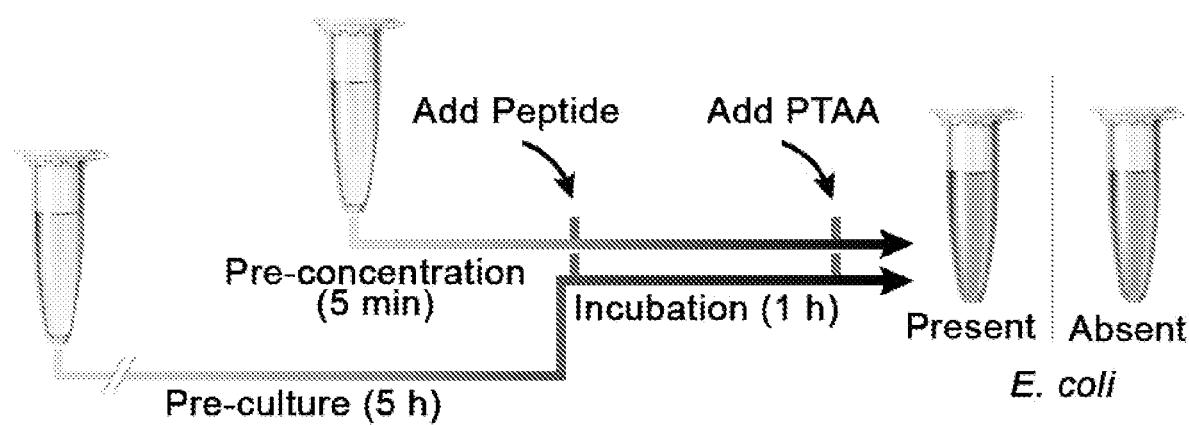
FIG. 3 shows the pre-concentration and pre-culturing steps that may be included in the methods of the invention in order to increase the sensitivity/limit of detection.

In order to improve the detection of *E. coli*, the CFU concentration of the samples was increased by either: A) Pre-concentrating the sample, or B) Pre-culturing of the sample. An outline of the steps involved in each of these approaches is shown in FIG. 3.

Pre-Concentration Based Approach:

Four different strains for *E. coli*, as mentioned in Table 6, were used to test the membrane protease method for sensing *E. coli* in water samples. The four different strains were grown overnight in LB media at 37° C. while shaking at 220 RPM. This primary culture was used for inoculating a secondary culture, which was further allowed to grow for 6-8 hours. The Lemo21(DE3) cells with OmpT plasmid were induced with 1 µM IPTG at OD$_{600}$=~0.8. For OmpT overexpression in *E. coli* Lemo21(DE3), the *E. coli* Lemo21 (DE3) cells were allowed to grow for 4 hours after induction with 1 µM IPTG. All four strains of *E. coli* were pelleted and then resuspended in the reaction buffer before serially diluting them to attain concentrations of $10^8$-$10^3$ CFU/mL, considering OD$_{600}$=1 equivalent to $8\times10^8$ CFU/mL. 200 µL, 2 mL and 20 mL of *E. coli* cells with $10^8$, $10^7$ and $10^6$-$10^3$ CFU/mL, respectively, were filtered through a 0.2 µm PTFE centrifuge device. After filtering the sample, 100 µL of reaction buffer was added to the centrifuge device and was gently vortexed to resuspend the *E. coli* cells. 90 µL of the reaction mixture was retrieved from the centrifuge device to which 10 µL of 500 µM LL37$_{FRRY}$ stock solution was added and mixed. This 100 µL reaction mixture was incubated at 37° C. and shaking at 500 RPM for 1 hour. After which, 10 µL of PTAA stock solution (0.1 mg/mL) was added to the reaction mixture and the sample's fluorescence intensity and absorbance recorded.

Figure 11:
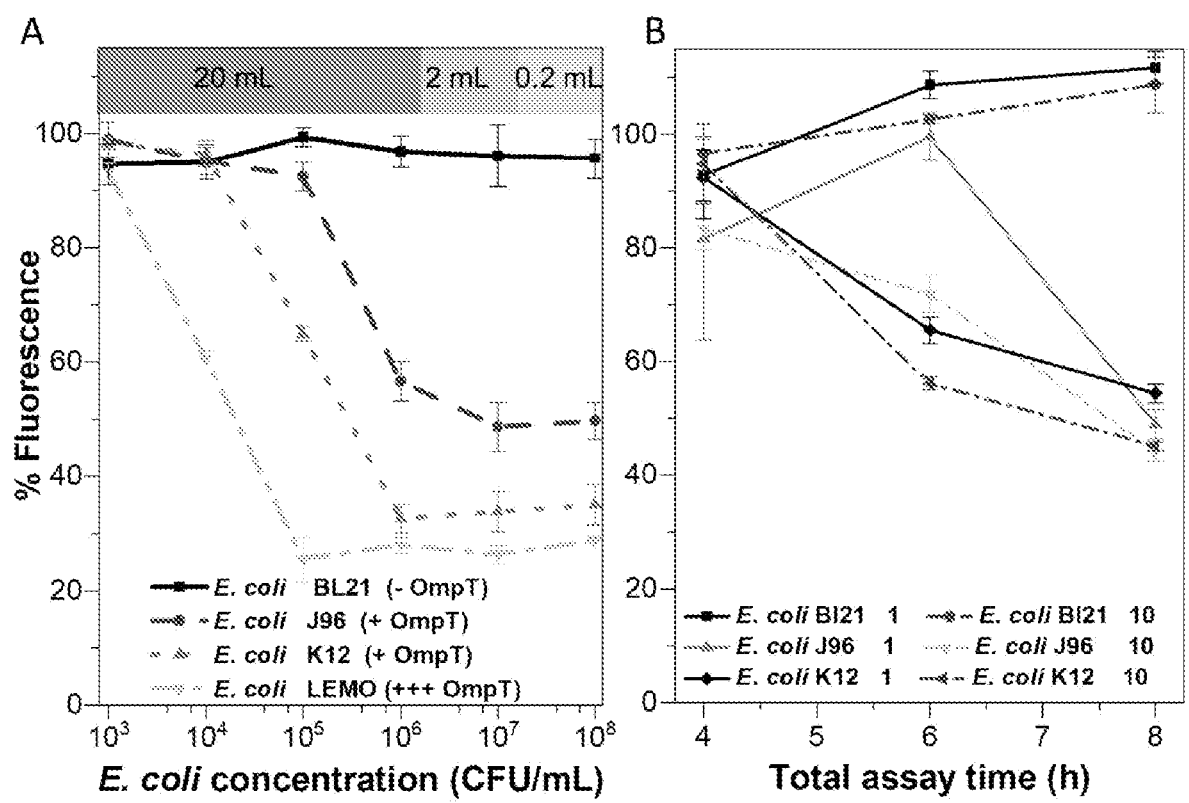
FIG. 11 depicts detection of different strains of *E. coli* and their limit of detection. (A): Fluorescence intensity of PTAA when mixed with $LL37_{FRRY}$ (SEQ ID NO: 7) treated with different *E. coli* strains while using the pre-concentration method. 200 μL (light grey), 2 mL (grey) and 20 mL (dark grey) of sample volumes were used for detecting $10^8$, $10^7$, $10^6$-$10^3$ CFU/mL of E. coli respectively. (B): Fluorescence intensity of PTAA when mixed with LL37$_{FRRY}$ (SEQ ID NO: 7) treated with E. coli K12 or J96 wildtype strains using pre-culture method for detecting 1 and 10 CFU/mL of E. coli. The data were normalised for the highest PTAA fluorescence intensity at 550 nm and plotted as % fluorescence. Error bars indicate standard error of the mean for data points averaged from duplicates for n=3.

The presence or absence of *E. coli* causes the fluorescence to decrease or remain the same, respectively. The results indicate a significant reduction in PTAA's fluorescence intensity for samples containing K12, J96, and Lemo21 (DE3) strains, suggesting that these *E. coli* strains were able to cleave LL37$_{FRRY}$ (FIG. 11A, dotted grey line with triangles, dashed black line with circles, dash-dotted grey line with inverted triangles). Control samples containing the *E. coli* BL21 strain did not show any reduction in PTAA's fluorescence intensity (FIG. 11 left, solid black line with squares). Moreover, the reduction in PTAA's fluorescence is consistent with the different levels of OmpT expressed on the surface of different *E. coli* strains. For the two wild-type strains, K12 and J96, the limit of detection (LOD) which was defined as a 20% change in fluorescence intensity, was $10^5$ and $10^6$ CFU/mL, respectively (FIG. 11A, dotted grey line with triangles, dashed black line with circles).

In summary, using this method it was possible to detect $10^4$, $10^5$, and $10^6$ CFU/mL of *E. coli* LEMO, K12 and J96, respectively, as the samples showed about ~60% residual fluorescence after peptide cleavage by OmpT. On the contrary, *E. coli* BL21 did not show a decrease in fluorescence for all the concentration of *E. coli* BL21, as no OmpT is present on their surface. *E. coli* J96 was detectable in the range of $10^8$-$10^6$ CFU/ml with pre-concentration of the sample.

Pre-Culture Culturing-Based Approach:

In order to establish the minimum pre-culturing time required for the membrane protease-based method to detect 1 and 10 CFU of *E. coli* cells, three different *E. coli* strains were employed. *E. coli* J96, K12, and BL21 strains at an initial concentration of 1 and 10 CFU/mL were cultured for 3, 5, and 7 hours respectively at 37° C. while shaking at 220 RPM. 200 µL of each of the cultured *E. coli* cells were filtered through a 0.2 µm PTFE centrifuge device after 3, 5 and 7 hours. To these filtered *E. coli* cells, 100 µL reaction buffer was added and vortexed gently to resuspend the *E. coli* cells. 90 µL of the reaction mixture was retrieved from the centrifuge device to which 10 µL of 500 µM LL37$_{FRRY}$ stock was added and mixed. This 100 µL reaction mixture was then incubated at 37° C. and 500 RPM for 1 hour. After which, 10 µL of PTAA stock solution (0.1 mg/mL) was added to the reaction mixture and the sample's fluorescence intensity and absorbance recorded.

Results indicate that PTAA's fluorescence intensity at 550 nm reduced by almost 35% and 44% for 1 and 10 CFUs/mL of K12 strain, respectively, when pre-cultured for only 5 hours (FIG. 11B, solid black line with diamonds and dash-dotted black line with triangles). Similarly, a reduction in PTAA's fluorescence intensity of 28% was observed for 10 CFUs/mL of J96 strain when pre-cultured for 5 hours (FIG. 11B, dash-dotted grey line with inverted triangles). It took 8 hours of pre-culturing to detect 1 CFU/mL of the J96 strain which showed a reduction of PTAA's fluorescence intensity of almost 51% (FIG. 11B, solid grey line with triangles). In other words, by using the pre-culture method of detection, as low as 1 CFU/mL of K12 E. coli can be detected within 6 h. And for J96, the E. coli strain commonly seen in urine samples of patients suffering from UTI, 1 CFU/mL can be detected within 8 h. This is significant because most commercially available kits require almost twice or three times as much time to detect 1 CFU/mL of E. coli.

In summary, the pre-culture method was able to detect 1 CFU/mL in 6 hours, which included 5 hours for pre-culture and 1 hour of assay time.

Example 4

Detection of Bacterial Contamination on Leafy Vegetables

Figure 4:
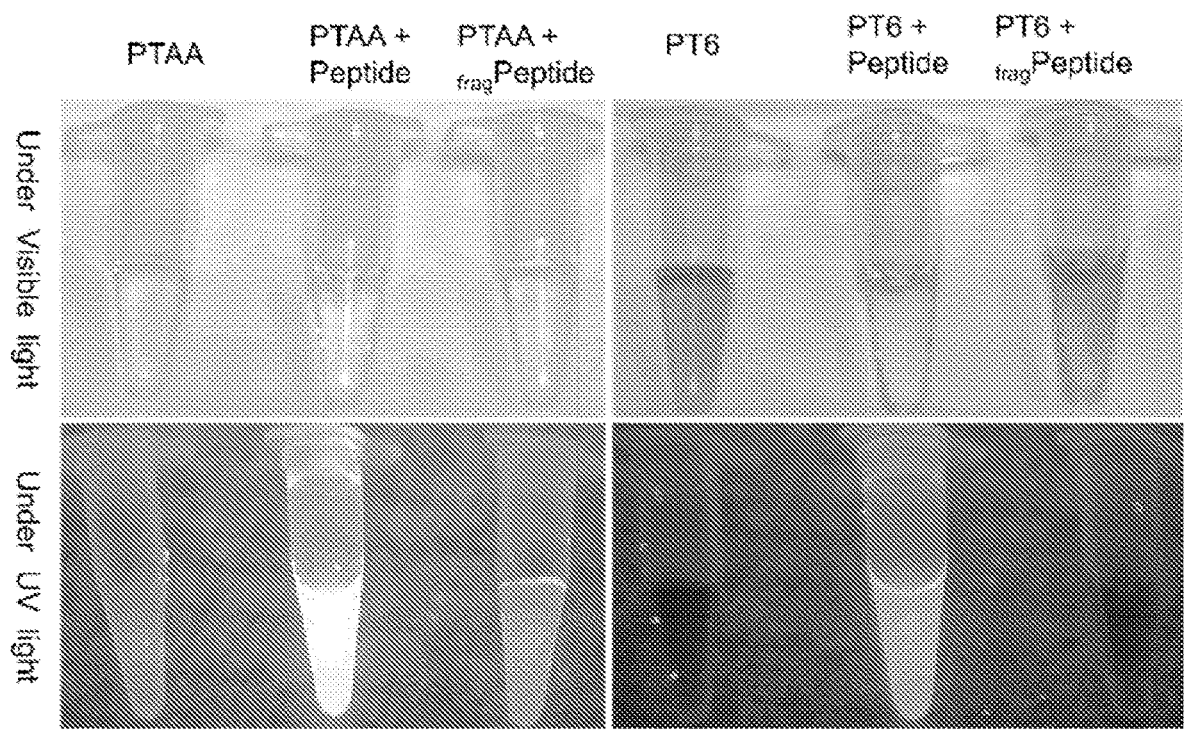
FIG. 4 shows the colour change under visible light and UV light for a membrane protease-based detection method of the invention using polythiophenes PTAA and PT6. A colour change was visible when the polythiophene was mixed with peptide $LL37_{FRRV}$ (SEQ ID NO: 7), while no colour change was visible using the polythiophene alone or in combination with cleaved peptide fragments. *E. coli* cleaves the peptide to produce fragments, thus causing a colour change when a mixture of polythiophene and $LL37_{FRRV}$ (SEQ ID NO: 7) is contacted with a solution containing *E. coli*.

The membrane protease-based method described was used to detect bacteria present on the surface of food samples that are prone to E. coli contamination. Store-bought lettuce, cabbage, and spinach were exposed to water contaminated with E. coli and then analysed. The results below confirm that bacterial contamination can be detected on these vegetables when they are exposed to contaminated water with E. coli levels as low as 10 CFU/mL By using the polythiophene derivative PT6 (poly[3(potassium-6-hexanoate)thiophene-2,5-diyl]), which has a slightly longer carbon tail and is more sensitive than PTAA, it was possible to slightly improve the LOD for the pre-concentration method. Most significantly, when PT6 is used as the reporter polymer, the need for a spectrophotometer to read the assay results is completely eliminated. The results of the assay can be easily detected with the naked eye when the samples are viewed under visible or UV light (FIG. 4). This represents a significant advantage, especially for home testing or testing without access to laboratory equipment.

Considering the sources of E. coli contamination on farm produce (Table 7) a majority of E. coli contamination is restricted to the vegetable's outer surface.

TABLE 7

Source of E. coli contamination in farm

| FARM | Via direct contact with animal faeces Contaminated irrigation water, bird faeces, and manure |
| PRODUCTION PLANT | Contaminated water used to wash produce Via equipment used to cut up leafy veggies |
| STORE | Cross contamination from raw foods Not bagged |

Hence, it is possible to detect bacterial contamination on fresh fruits and vegetables by first releasing the bacteria from the vegetable's surface and capturing it into a liquid medium. This liquid medium can then be assayed for detecting or quantifying bacterial contamination. Contamination of fresh vegetables was replicated by exposing green leafy vegetables to water deliberately contaminated with E. coli. At this point, the amount of E. coli that could be isolated from the vegetable's surface is too low to assay directly. Thus, after the brief exposure to contaminated water, the vegetables were transferred into a growth medium. The growth medium was incubated at 37° C. for 5 hours to facilitate E. coli growth and multiplication. After 5 hours, the growth medium was assayed using the OmpT-PTAA method to detect E. coli. Three approaches were tested as described below.

4.1: Soaking Food Samples in Contaminated Water

Store-bought, bagged leafy vegetables (lettuce, cabbage, and spinach) were cut into 22×22 mm squares and soaked in water contaminated with $10^6$ CFU/mL cells of E. coli. After soaking for 5 min, the samples were transferred into a small plastic tube containing growth media. After 15 min in the growth media, the samples were removed and the growth media incubated at 37° C. for 5 hours to facilitate bacterial growth and multiplication. After 5 hours, the growth media's turbidity was measured as absorbance at 600 nm and this absorbance value was used to approximate the number of E. coli cells. Since turbidity can be caused by more than just bacterial growth, the samples were also assayed with the OmpT-PTAA method which is specific for E. coli. Glass coverslips coated with poly L-lysine were used as positive controls since the negatively charged E. coli's surface is expected to adhere to the positively charged poly L-lysine. In order to determine whether more than one wash is necessary to remove all or most of the adhering bacteria from the vegetable's surface, an additional step was included after the first soaking step: Here, instead of discarding the samples after the first 5 min soak, they were transferred into a second tube containing growth media and allowed to soak for 15 min before finally discarding the samples and incubating the growth media at 37° C. for 5 h. For negative control, vegetable samples were soaked in clean, uncontaminated, deionised (DI) water that was filtered through a 0.2 μm filter.

Figure 5:
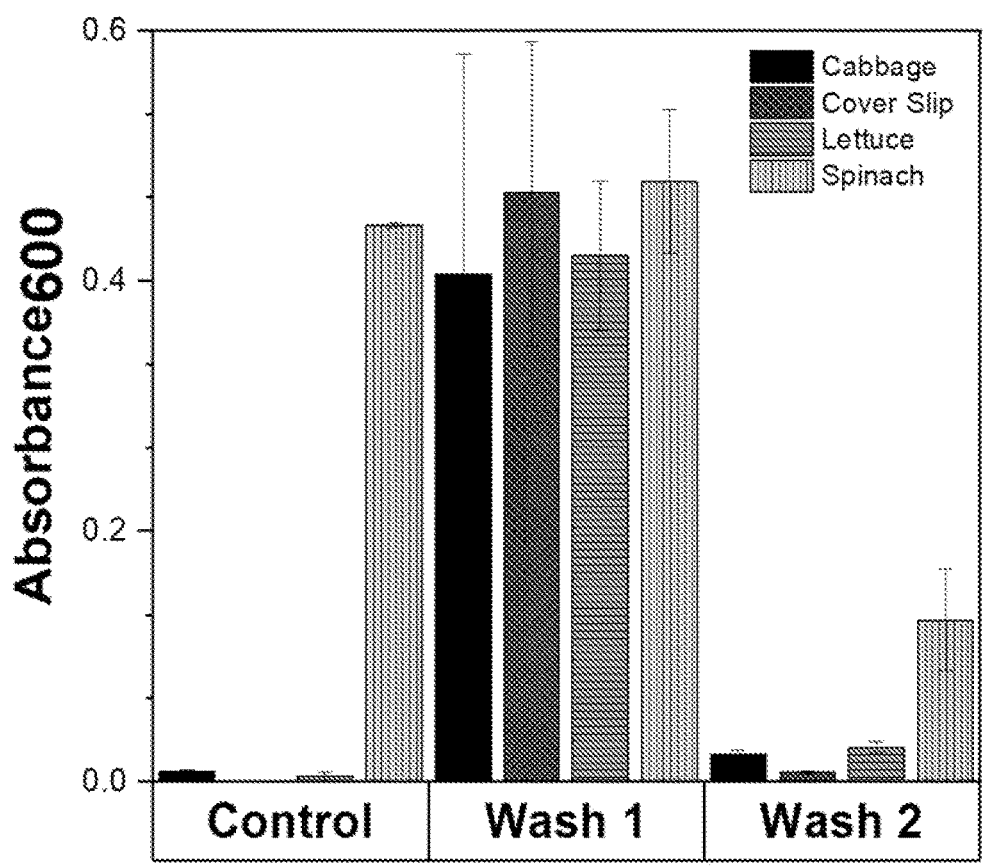
FIG. 5 shows optical absorption at 600 nm for the vegetables cabbage, lettuce and spinach tested for *E. coli* surface contamination as described in Example 4.1.

Results for the above experiment are presented in FIG. 5, which shows a plot of the absorbance values of the growth media at 600 nm for the different samples and controls. As expected, control samples of lettuce and cabbage exhibit very low absorbance values indicating no bacterial growth. However, the spinach control shows a high absorbance value indicating E. coli contamination. It appears that the spinach used in this experiment was already contaminated before its packaging was opened.

After the first soak of 5 min, all vegetable samples and the positive control show high absorbance values indicating bacterial growth. When compared to the second wash where very little bacterial growth is observed, it is clear that most of the E. coli is released into the growth media during the first 15 min. The results show that E. coli on the surface of vegetables can be captured and detected using the above methodology.

4.2: Depositing Contaminated Water Directly on the Surface of Food Samples

The surface morphology of vegetables vary greatly, and E. coli can be expected to display a preference to adhere more strongly to one surface than to another. In order to determine if E. coli displayed such a variability in its adherence/release properties for the vegetables selected for this study, a known quantity of E. coli was deposited on each of the different vegetable's surface and the samples assayed. A similar experimental protocol, as described in Approach 4.1, was followed but with slight modification. Instead of soaking the samples in contaminated water, 10 μL of E. coli at a concentration of $10^6$ CFU/mL was deposited directly onto the vegetable's surface. These samples were allowed to sit at 4° C. overnight to allow the bacteria to adhere properly to the surface. The following day, the samples were transferred into plastic tubes containing growth media. The reminder of the steps were similar to those described in Approach 4.1.

Figure 6:
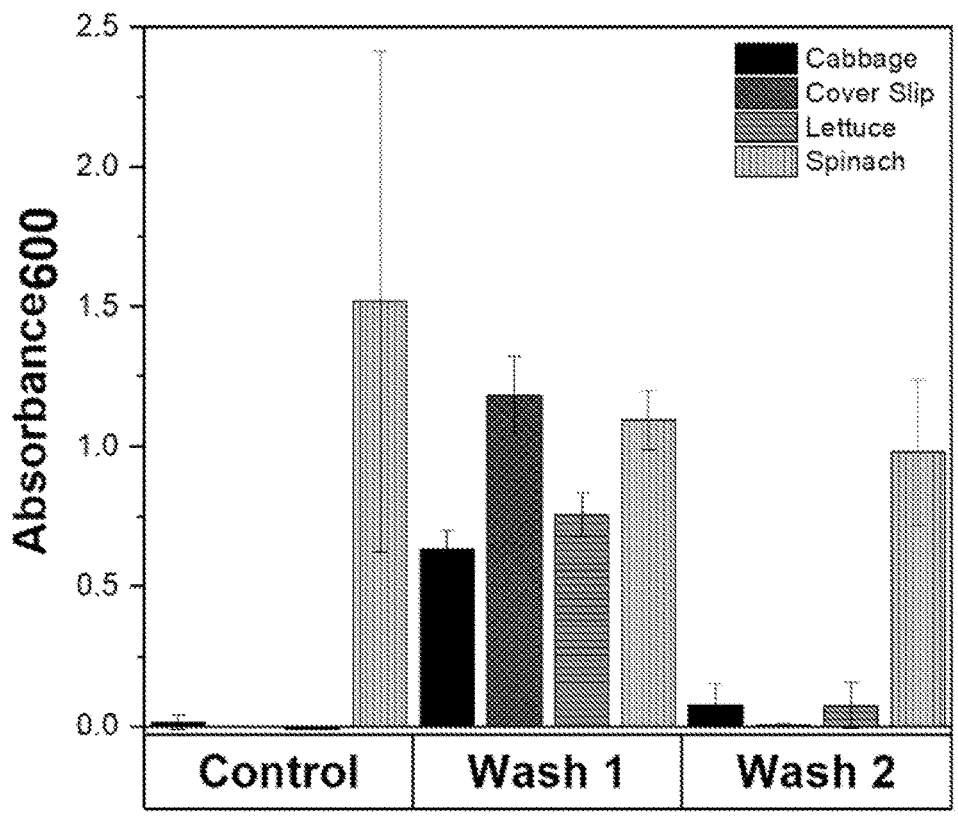
FIG. 6 shows optical absorption at 600 nm for the vegetables cabbage, lettuce and spinach tested for *E. coli* surface contamination as described in Example 4.2.

Results presented in FIG. 6 once again indicate that control samples that were not exposed to the contaminated E. coli water did not show any bacterial growth except for the spinach samples which are believed to have been contaminated at time of purchase. However, absorbance values of samples exposed to contaminated water, indicate that a significant amount of E. coli came-off the vegetable's surface. However, the differing amount of E. coli cells released from the vegetable surface indicates that the different surfaces adsorb or release E. coli to varying degrees. Nonetheless, despite the difference in levels of E. coli released from each vegetable's surface, sufficient E. coli was captured to enable a proper assay of the sample.

4.3: Increasing Sampling Area for Analysis of Food Samples Soaked in Contaminated Water The amount of E. coli retrievable from the surface of a leafy vegetable is dependent on the concentration of E. coli on the surface as well as the surface area available for sampling. When more of the vegetable's surface area is sampled, the easier it is to detect E. coli contamination. To investigate this effect and to get an idea of the average surface area needed for sampling, 1, 2, 5, 8 and 10 small squares of lettuce measuring 22×22 mm were soaked in water deliberately contaminated with 10 CFU/mL E. coli. With the remainder of the steps being similar to those in Approach 1, the growth medium after 5 hours was assayed using the OmpT-PTAA method.

Figure 7:
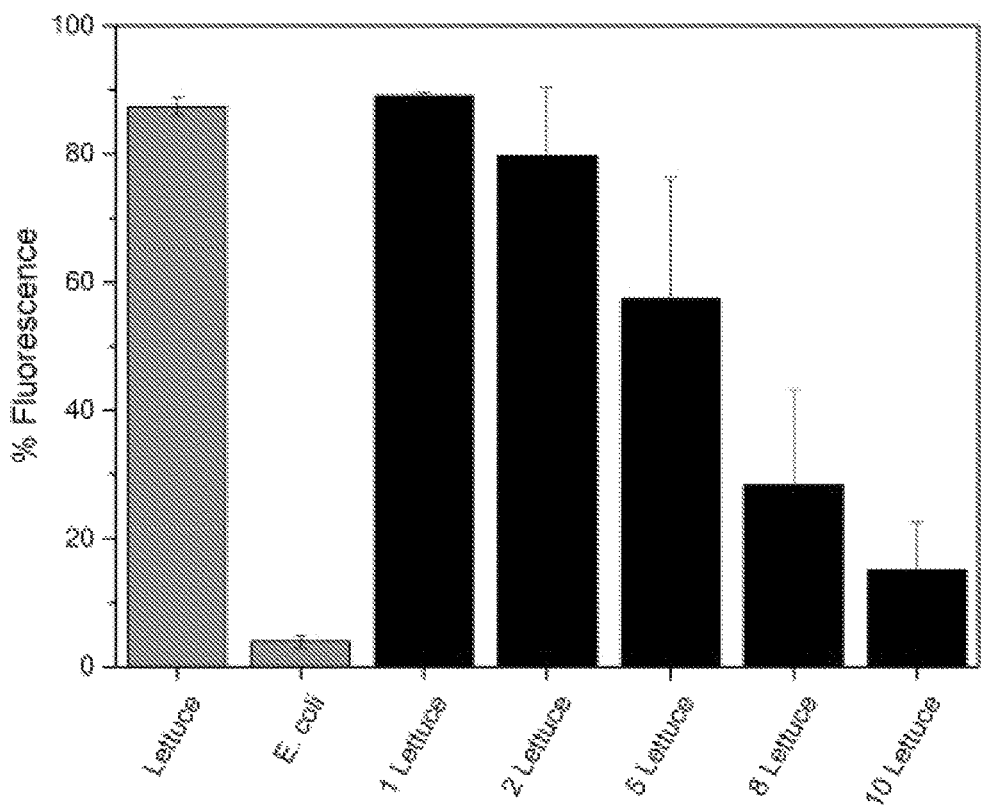
FIG. 7 shows fluorescence decreased with increased *E. coli* detection when more of a lettuce sample was analysed as described in Example 4.3.

As shown in FIG. 7, hardly any E. coli was detectable when only 1 or 2 lettuce squares were used. However, when 5 or more of the squares were used, there was a significant reduction in the fluorescence intensity indicating presence of E. coli. Control samples where 10 squares of lettuce were soaked in DI water instead of the E. coli contaminated water, indicated no E. coli as seen from the absence of any significant reduction in % fluorescence. As expected, more E. coli could be captured and detected from the vegetable's surface when the sampling area was increased.

Example 5

Testing an Alternative Conjugated Reporter Polymer (PT6)

When polythiophene acetic acid (PTAA) was used as a reporter polymer, the detection limit was approximately $10^5$ CFU/mL E. coli cells within a total assay time of 1 hour using the pre-concentration method. The % increase in PTAA's fluorescence upon peptide addition was almost 200%.

Figure 8:
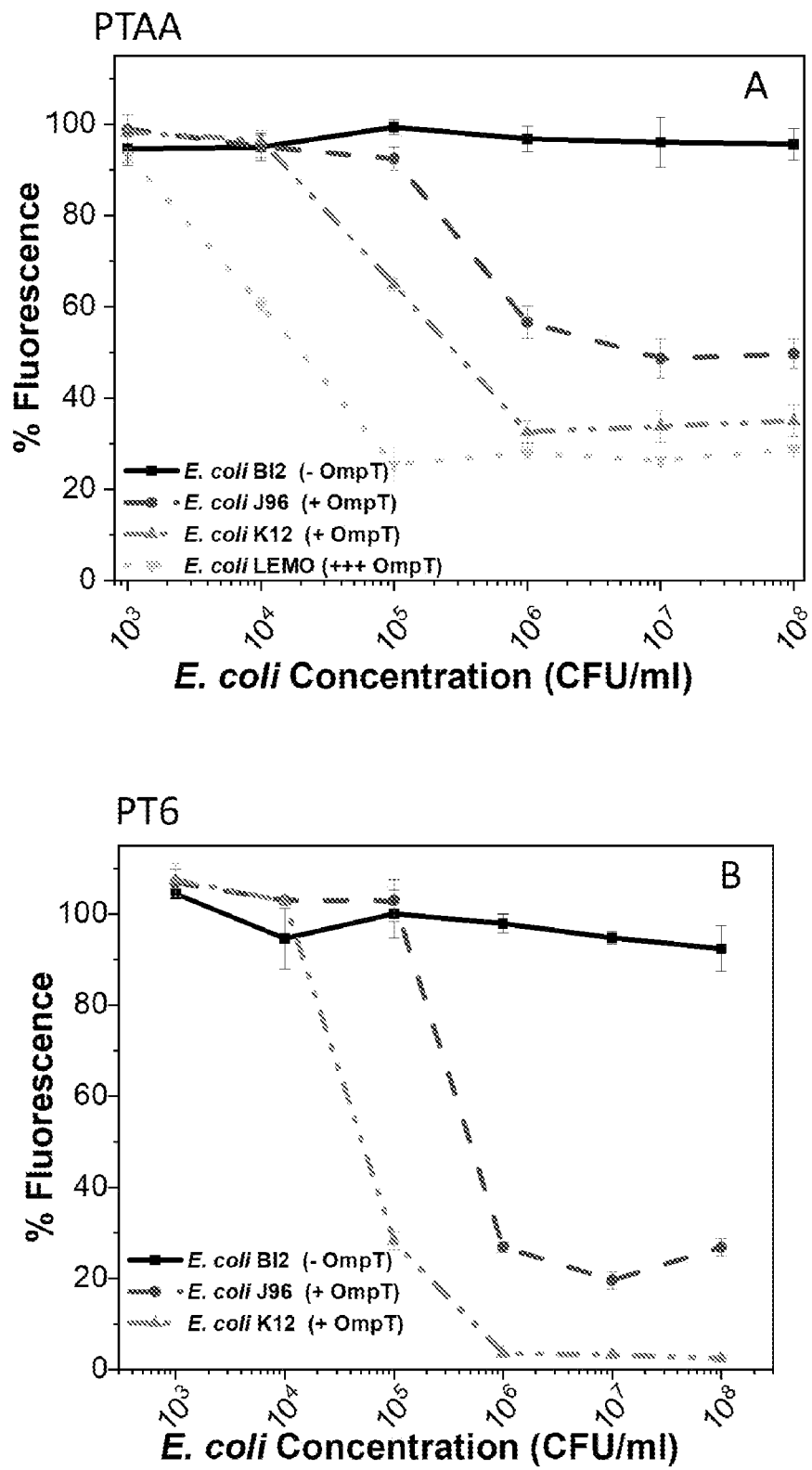
FIG. 8 compares *E. coli* detection with (A) PTAA and (B) Poly[3-(potassium-6-hexanoate)thiophene-2,5-diyl] (PT6), using $LL37_{FRRY}$ (SEQ ID NO: 7). The window of measurement corresponding to % fluorescence intensity change between no *E. coli* and $10^4$ CFU/mL *E. coli* is 80% for PTAA and ~95% for PT6.

Using an alternative reporter polymer, poly[3(potassium-6-hexanoate)thiophene-2,5-diyl] (PT6), the % increase in fluorescence is approximately 2000%. This substantial increase in fluorescence provides a slight improvement in limit of detection from $10^5$ CFU/mL for PTAA to somewhere between $10^5$ and $10^4$ CFU/mL of E. coli (FIG. 8). More significantly, even with low concentrations of PT6, it is possible to read the assay results with the naked eye. A solution of PT6 is purple in colour and changes to orange when mixed with the intact peptide (FIG. 4). However, when the intact peptide is exposed to E. coli before mixing with PT6, there is no colour change and the solution remains purple. These changes are easily detectable with the naked eye and become even more pronounced when viewed under UVA light. Other non-limiting examples of reporter polymers that may be used in the invention are listed in Table 8.

TABLE 8

| Conjugated polymers as substituents for reporter polymer in the assay | | | |
|---|---|---|---|
| Polymer Class | Specific Example | Structure | Ref |
| Poly(1,4-phenylene vinylene) (PPV) | poly[2-methoxy-5-(3'-propyloxysulfonate)-1,4-phenylenevinylene | $OC_5H_{10}COOH$ ... $HOOCC_5H_{10}O$ ... R = H / OMe / $OCH_2CH_2OMe$ / $OCH_2CH_2OCH_2CH_2OMe$ / $OCH_2CH_2OCH_2CH_2OCH_2CH_2OMe$ — PMDH, PDDMe, PDMonoG, PDDIG, PDTYIG | [1] |
| Poly(1,4-phenylene) (PPP) | N.A | | N.A |
| Polyfluorenes (PFO) | polyfluorene-poly(9,9-bis(4'-sulfonatobutyl)fluorene-co-alt-1,4-phenylene) sodium salt (PFS) | PFS ($NaO_3S$, $SO_3Na$) | [2] |

TABLE 8-continued

Conjugated polymers as substituents for reporter polymer in the assay

| Polymer Class | Specific Example | Structure | Ref |
|---|---|---|---|
| Poly(2,5-pyridinevinylene) (PPyV) | N.A | 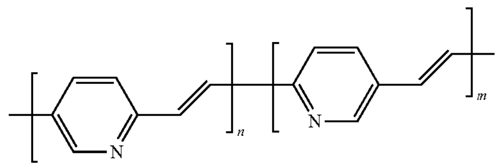 | [3] |
| Poly(9-vinylcarbazole) (PVK) | N.A | 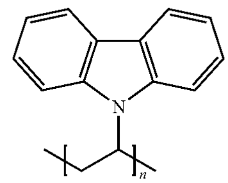 | N.A |
| Polypyrroles | polypyrrole(Ppy) doped with SO4$^{-2}$ ions | 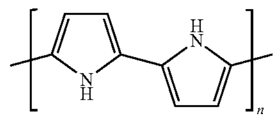 | [4] |

[1. Dwight, S.J.; et al., *J. Am. Chem. Soc.* 2004, 126, 16850-16859]
[2. Huang, F.; et al., Polymer (Guildf). 2005, 46, 12010-12015]
[3. Gillissen, S.; et al., *Macromolecules* 2001, 34, 7294-7299]
[4. De J. Licona-Sánchez, T.; et al., *In Proceedings of the ECS Transactions*; ECS, 2009; Vol. 20, pp. 385-392]

Example 6

Testing Alternative Peptides Cleaved by OmpT

Three new peptide substrates were identified to be cleaved by the protease (OmpT) much more rapidly than the LL37$_{FRRY}$ peptide substrate used in Examples 1-5. The sequences of the peptides are shown in Table 9 below.

TABLE 9

Identities of peptide sequences with higher affinity for OmpT

| Peptide ID | Sequence | SEQ ID NO. |
|---|---|---|
| LL37$_{FRRV}$ (used in Examples 1-5) | C L L G D F F R R V K E K I G | 7 |
| LL37$_{FRRY}$ | C L L G D F F R R Y K E K I G | 8 |
| LL37$_{FRRA}$ | C L L G D F F R R A K E K I G | 9 |
| LL37$_{YRRA}$ | C L L G D F Y R R A K E K I G | 10 |

Analysis of Performance of the LL37 Peptides

Figure 13:
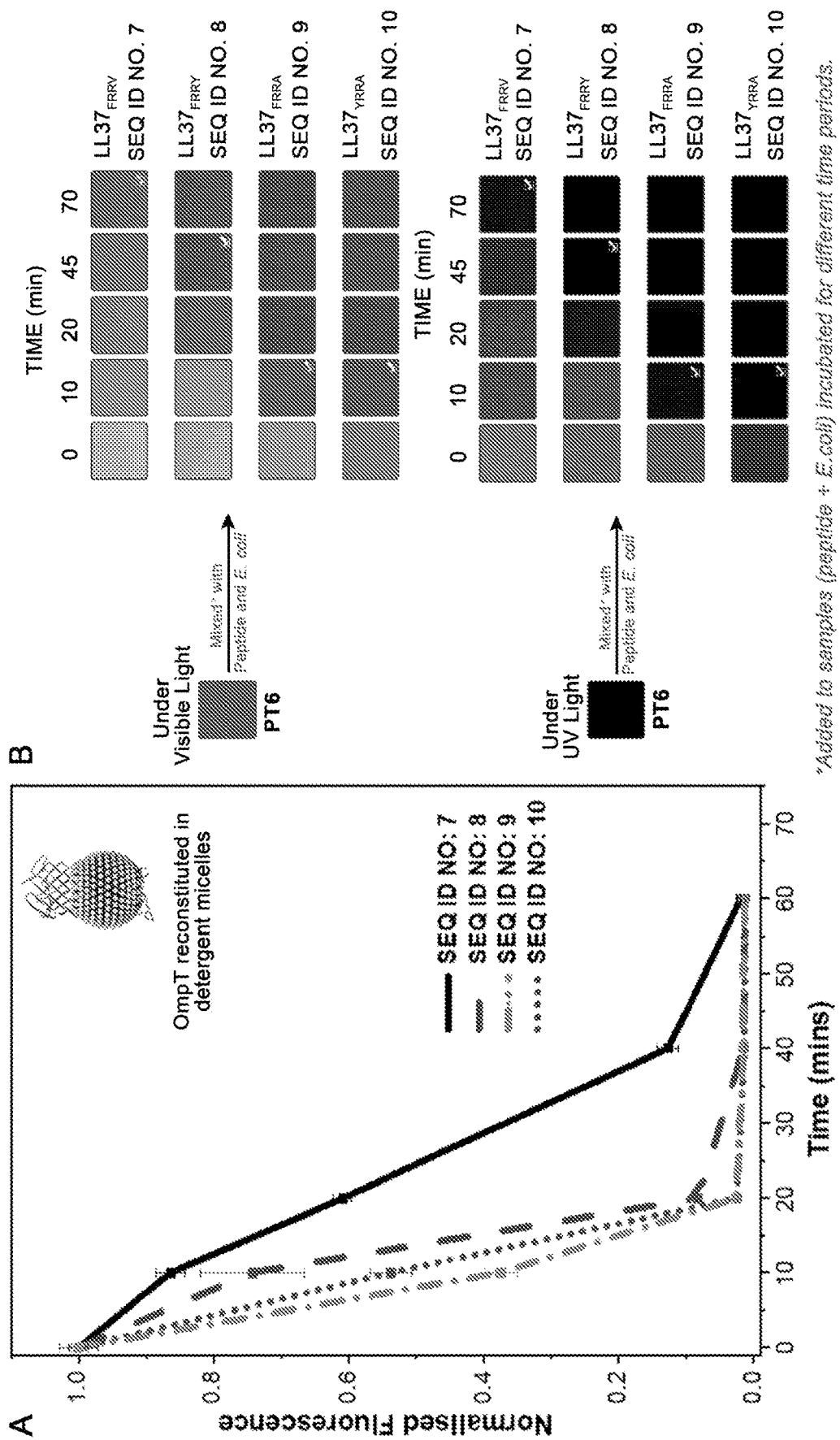
FIG. 13 shows fluorescence and colorimetric data of PT6 when mixed with various peptide substrates exposed to OmpT in detergent micelles. (A) Comparison of changes in PT6 fluorescence when mixed with different peptide substrates incubated with OmpT for increasing time periods. (B) Samples in A when imaged under normal visible light (top) and under UV-A light (bottom), showing the gradual colour change.

FIG. 13A summarises the fluorescence data for PT6 when mixed with the different peptide substrates and exposed for various time periods to OmpT reconstituted in detergent micelles. The fluorescence data shows that all four peptide substrates exhibit a concomitant reduction in fluorescence, and this reduction occurs at a faster rate (as interpreted from the slope) for LL37$_{FRRY}$, LL37$_{FRRA}$, and LL37$_{YRRA}$. While LL37$_{FRRY}$ required >40 min incubation with OmpT to achieve an almost complete reduction in PT6 fluorescence, LL37$_{FRRY}$, LL37$_{FRRA}$, and LL37$_{YRRA}$ were able to achieve the same results in less than 20 min.

When the samples were analysed for colorimetric changes with the naked eye under normal visible light and under UV-A light, they exhibited similar trends to those seen with the fluorescence data in FIG. 13A (FIG. 13B, top and bottom panels, respectively). A solution of PT6 is purple coloured when viewed under normal visible light and this colour changes to bronze when mixed with the intact peptide substrate (FIG. 14B top panel, dark grey represents purple colour and light grey represents bronze colour). However, addition of the cleaved peptide substrate does not result in any colour change and the PT6 solution remains purple coloured. FIG. 13B shows the colour of PT6 when mixed with LL37$_{FRR}$y that had been incubated with OmpT for 0, 10, 20, 45, and 70 min. The top panel of FIG. 13B shows a gradual colour change from light grey to dark grey (when moving from left to right) representing the actual colour change from bronze for the 0 min sample to purple for the 70 min sample, confirming that the peptide substrate was cleaved by OmpT. However, with LL37$_{FRRA}$ and LL37$_{YRRA}$, this colour change occurred much sooner with the 10 min sample, confirming that the peptide substrate cleavage was much more rapid.

Similar trends were observed when the samples were analysed under UV-A light (FIG. 13B, bottom panel). A dilute solution of PT6 does not emit any light (and is thus black) when imaged under UV-A light, but emits a bright crimson red colour (represented as light grey in FIG. 13B bottom panel and can be seen for 0 minute samples) when mixed with the intact peptide substrates. However, mixing the cleaved peptide substrate with PT6 results in no light emission and the sample remains black. The UV-A light results are consistent with the visible light results: LL37$_{FRRY}$, LL37$_{FRRA}$, and LL37$_{YRRA}$ are cleaved faster than LL37$_{FRRY}$, resulting in colour changes within 10 mins of incubation with OmpT. LL37$_{YRRA}$ and LL37$_{FRRA}$ were fully cleaved by OmpT in less than 20 min.

Detection of *E. coli* Using the LL37 Peptides

Figure 14A:
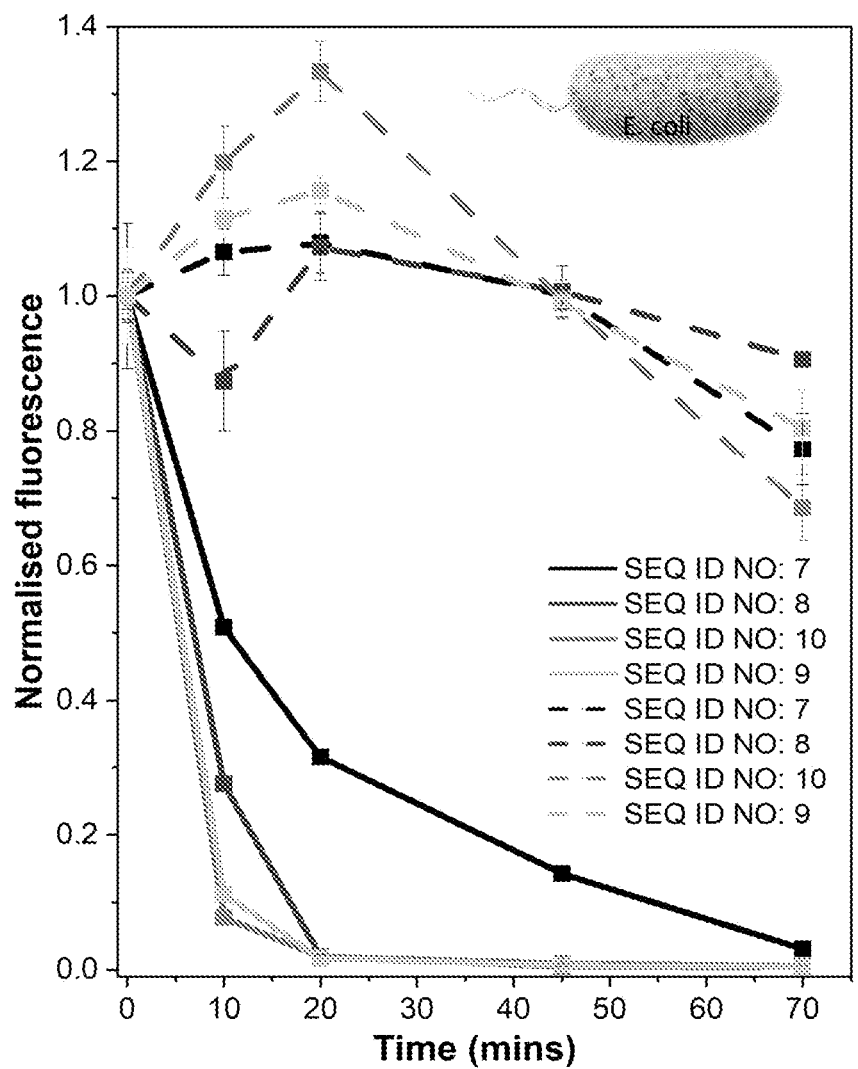
FIGS. 14A-14B shows fluorescence data of PT6 when mixed with various peptide substrates exposed to E. coli.

When the four peptide substrates were incubated with water samples artificially contaminated with 10$^8$ CFU/mL of wild type *E. coli* K12 strain, before mixing with PT6, they exhibited a time-dependent reduction in PT6 fluorescence (FIG. 14A, solid lines). While all four peptide substrates exhibited a reduction in fluorescence, this reduction occurs at a faster rate (as interpreted from the slope) for LL37$_{FRRY}$, LL37$_{FRRA}$, and LL37$_{YRRA}$ (FIG. 14A, solid lines).

As a control, PT6 mixed with peptide substrates were incubated with water samples contaminated with BL21 *E. coli* cells. These controls did not exhibit a significant reduction in fluorescence since the BL21 strain of *E. coli* lacks surface OmpT and is thus unable to cleave the peptide substrates (FIG. 14A, dashed lines).

Figure 14B:
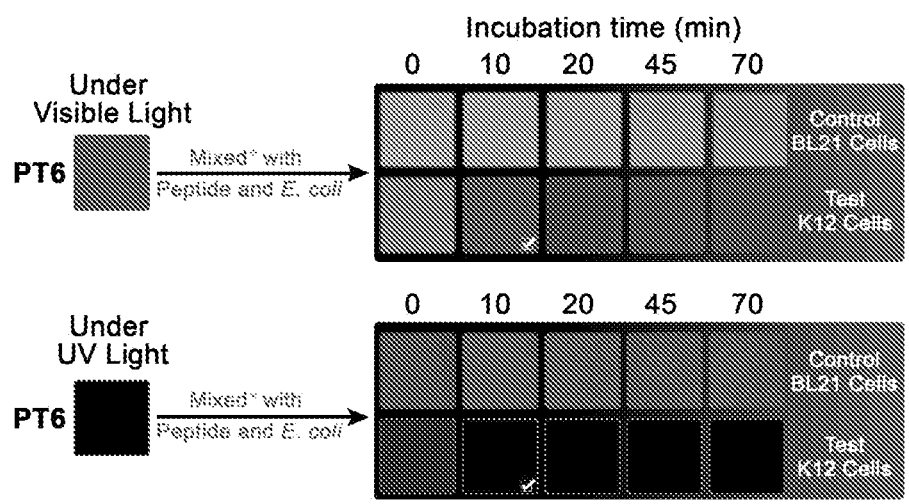

When the above samples were analysed for colorimetric changes with the naked eye under normal visible light and under UV-A light, they exhibited similar trends to those seen with the fluorescence data. FIG. 14B shows that PT6 when mixed with LL37$_{YRRA}$ incubated with highly contaminated water samples of *E. coli* K12 strain for 0, 10, 20, 45, and 70 min, rapidly changed colour from bronze for the 0 min sample to purple for the 10 min sample (FIG. 14B, top). As expected, there was no change in colour for highly contaminated control water samples of BL21 *E. coli* cells even when the peptides were incubated for 70 min.

Similar trends were observed when the samples were analysed under UV-A light (FIG. 14B, bottom panel). The data indicates that by using PT6 and LL37$_{YRRA}$, *E. coli* detection in highly contaminated samples can easily be achieved using a visible light colour change in as little as 15 min.

The data shows that the total assay time for detecting *E. coli* in highly contaminated water samples using the methods of the invention can be as short as 15 minutes. Thus, in contrast to commercially available *E. coli* detection kits that take up to 24 hours to report their results (Table 10), the OmpT-PTAA methods of the invention provide a detection time that up to 99% faster.

Example 7

Detection and Differentiation Between Pathogenic and Non-Pathogenic Bacteria

Figure 15:
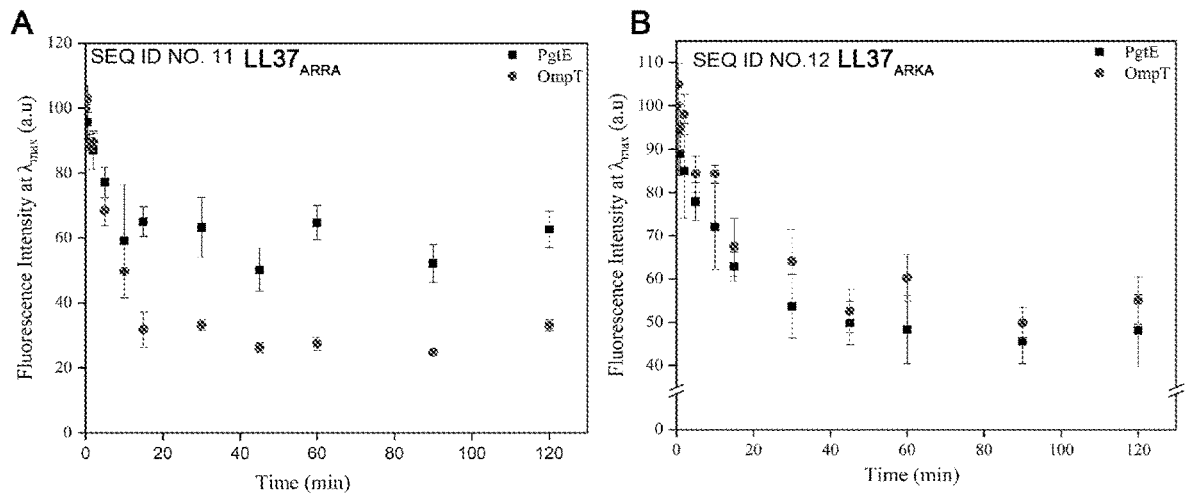
FIG. 15 shows peptide substrate preference between OmpT and PgtE. A comparison of the protease activity of OmpT and PgtE, measured as the change in PT6 fluorescence with time, for the two peptides (A) LL37$_{ARRA}$ C L L G D F A R R A K I G (SEQ ID NO: 11) and (B) LL37$_{ARKA}$ C L L G D F A R K A K E K I G (SEQ ID NO: 12).

One approach involves taking advantage of the documented difference in inherent peptide substrate specificities of the omptin proteases present on pathogenic or non-pathogenic bacteria. By introducing minor (<25%) modifications to the peptide substrate sequence with an intention to target specific omptin protease(s), the assay can be tuned to differentiate between a pathogenic and non-pathogenic bacteria. As an example, two peptide substrates: LL37$_{ARRA}$ C L L G D F A R R A K E K I G (SEQ ID NO: 11) and LL37$_{ARKA}$ C L L G D F A R K A K E K I G (SEQ ID NO: 12) whose sequence differed in only one residue were employed in the assay to detect OmpT (present on non-pathogenic *E. coli* K-12) or PgtE (present on pathogenic *Salmonella typhi*) in an aqueous sample. A comparison of the proteolytic activity, measured as the change in PT6 fluorescence with time, of the two peptides indicates that OmpT exhibits a higher preference for LL37$_{ARRA}$ (SEQ ID NO: 11) than does PgtE (FIG. 15). Such subtle differences in substrate preferences can be exploited to target specific omptin proteases that reside on pathogenic and non-pathogenic bacterial strains.

Figure 16:
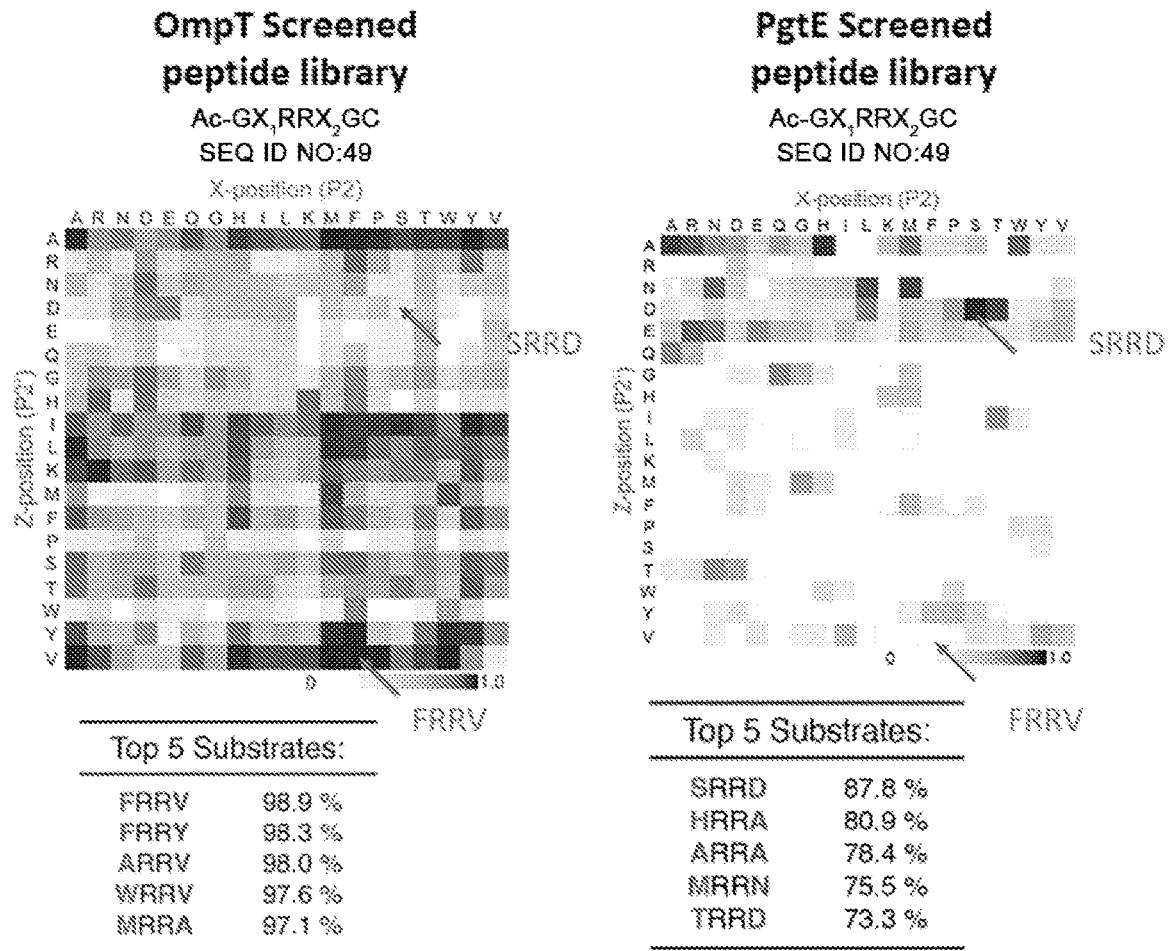
FIG. 16 shows SAMDI-MS screening of peptide array to identify substrate specificities of OmpT and PgtE. OmpT (left) and PgtE (right) activity screening of a combinatorial peptide library with substrate sequence AcGX$_1$RRX$_2$GC (SEQ ID NO: 49) displayed as heatmap. The top five peptide substrates and corresponding OmpT and PgtE activities are displayed in the table below each heatmap.

As for the peptide substrate LL37$_{ARRA}$ (SEQ ID NO: 11), both OmpT and PgtE seem to exhibit similar preferences. Similarly, OmpT and PgtE activity screening of a combinatorial peptide library with substrate sequence of the type AcGX$_1$RRX$_2$GC (SEQ ID NO: 49) where X$_1$ and X$_2$ are independently any of 19 different amino acids except cysteine, revealed that OmpT and PgtE have different substrate preferences (FIG. 16). As an example, peptide carrying the tetrapeptide sequence FRRV (SEQ ID NO: 1) at the cleavage site were efficiently cleaved by OmpT but not PgtE. On the other hand, peptide substrates with the tetrapeptide sequence SRRD at the cleavage site were preferentially cleaved by PgtE but not OmpT.

Just as it is possible to exploit the subtle differences in substrate specificities to distinguish between omptins from different bacterial species, it is also possible to differentiate between omptins of different bacterial strains within the same bacterial species. The expression of omptin proteins on the bacterial outer membrane is known to be upregulated in some pathogenic strains [Desloges, I. et al., *Microbiologyopen*, 8, 1-36 (2019)] along with a concomitant increase in proteolytic activity. Such an increase in the number of proteases and their proteolytic activity means that pathogenic strains could digest a known quantity of the peptide substrate much more efficiently and rapidly than a non-pathogenic strain of bacteria. By designing the assay in a way that controls for the number of bacterial cells being assayed, the faster digestion, i.e results achieved in a shorter time span, can be used as a determinant to differentiate between a pathogenic and non-pathogenic bacterial strain.

Example 8

RGB—Delta-E Analysis

Digital images of the vials are captured using a digital camera positioned at a fixed distance from the vials. The digital images are then transferred to the computer as jpeg files for image processing. RGB analysis of various regions of interest (~25×25 pixels) are then carried out using ImageJ image processing software in order to obtain colorimetric responses [Rajwar, D.; et al., *ACS Appl. Mater. Interfaces* 8, 8349-8357 (2016)]. Furthermore, ΔE values, a metric for human eye perception of color differences, are calculated using the International Commission of Illumination (CIE) algorithm [Hill, B.; et al., *ACM Trans. Graph.* 16, 109-154 (1997)]. ΔE values typically ranges from 0 to 100 with the experimentally established human vision perceptibility threshold value of 2.

Image processing could also be carried out using smartphone that captures the images of the vials followed by analysis using an in-build app. A smart phone application has been demonstrated for digitizing the colorimetric responses, followed by an analysis using an inbuilt algorithm to yield quantitative readouts of the concentration of analytes at the user interface [Aydin, B. A. et al., *Talanta* 209 120581 (2020)].

TABLE 10

Selected examples of commercially available microbial detection kits

| S. No | Product | Company | Target Organism | Assay Type | Test Sample | Pre-treatment/ Separation/ Concentration | Limit of Detection | Total Assay Time | Storage Condition |
|---|---|---|---|---|---|---|---|---|---|
| 1 | AquaVial E. coli and Coliform Water Test Kit | Aquabsafe | E. coli O157:H7 | Colorimetric assay | Water | None | 1 CFU/mL | within 24 h at 37° C. | N.A |
| 2 | MicroSnap ™ E. coli Test Kit | Hygiena | E. coli | Bioluminogenic substrate and Hygiena's EnSURE luminometer | Water | Pre culturing | <10 CFU | 8 h | N.A |
| 3 | Drinking Water Test Kit (E.coli/ Coliform Test) | Rakiro | E. coli and Coliform bacteria | Colorimetric assay (Enzyme not mentioned) | Water | Pre culturing | 1 CFU/ 100 mL | 18-24 h | Room temp |
| 4 | Compartment Bag Test (CBT) | Aquagenx | E. coli and Coliform bacteria | Colorimetric assay | Water | Pre culturing | N.A | 24-48 h | Room temp |
| 5 | Colilert | IDEXX | E. coli and Coliform bacteria | Enzyme | Water | Pre culturing | N.A | Within 24 h | Room temp |
| 6 | Solus E. coli O157 ELISA | Solus Scientific | E. coli O157:H7 | ELISA | Raw beef, milk and dairy products, vegetables and environmental samples | Enrichment | $10^4$-$10^5$ CFU/mL | 18-22 h | COLD (2-8° C.) |
| 7 | Lateral Flow System for E.coli O157 | Hygiena | E. coli O157:H7 | LFI and anti-E. coli O157 antibodies conjugated to colloidal gold | Ground and boneless beef | 8 h for 25 g samples | 1-4 CFU/ 25 g sample | 8-8.25 h | 15-30° C. |

Example 9

Effect of Peptide Net Charge on PTAA Fluorescence

Stock solutions of PTAA were prepared at a concentration of 0.1 mg/mL in a reaction buffer containing 20 mM sodium phosphate buffer whose pH was adjusted to 8 using HCl. Peptide stock solutions were prepared in the reaction buffer at a concentration of 2 mM. The six different peptides in table 11 were pipetted into individual wells of a 384 well plate to a final concentration of 20 µM and to which, 30 µg of recombinant OmpT was added such that the total sample volume was 50 µL. The sample mixture was incubated at 37° C. for 6 hours in a heating block. 5 µL of dialysis buffer (in which recombinant OmpT was dissolved) was added to control wells containing only 20 µM peptide, but no enzyme. At the end of incubation, 50 µL of PTAA (10 µg/mL) was added to each well and their fluorescence intensity measured using a TECAN Infinite® 200 PRO (Switzerland). Fluorescence scans were collected by exciting the samples at 420 nm and their emission spectrum recorded from 450-750 nm.

TABLE 11

LL37$_{FRRV}$ peptides with different net charge

| Peptide Sequence | Net Charge | SEQ ID NO. |
|---|---|---|
| Ac-CLLGDFFRRVKEKIG | +2 | 50 |
| Ac-CLLGDFFRRVKEAIG | +2 | 51 |
| Ac-CLLGDFFRRVAEAIG | 0 | 52 |
| CLLGDFFRRVKEKIG | +3 | 7 |
| CLLGDFFRRVKEAIG | +2 | 53 |
| CLLGDFFRRVAEAIG | +1 | 54 |

Figure 17:
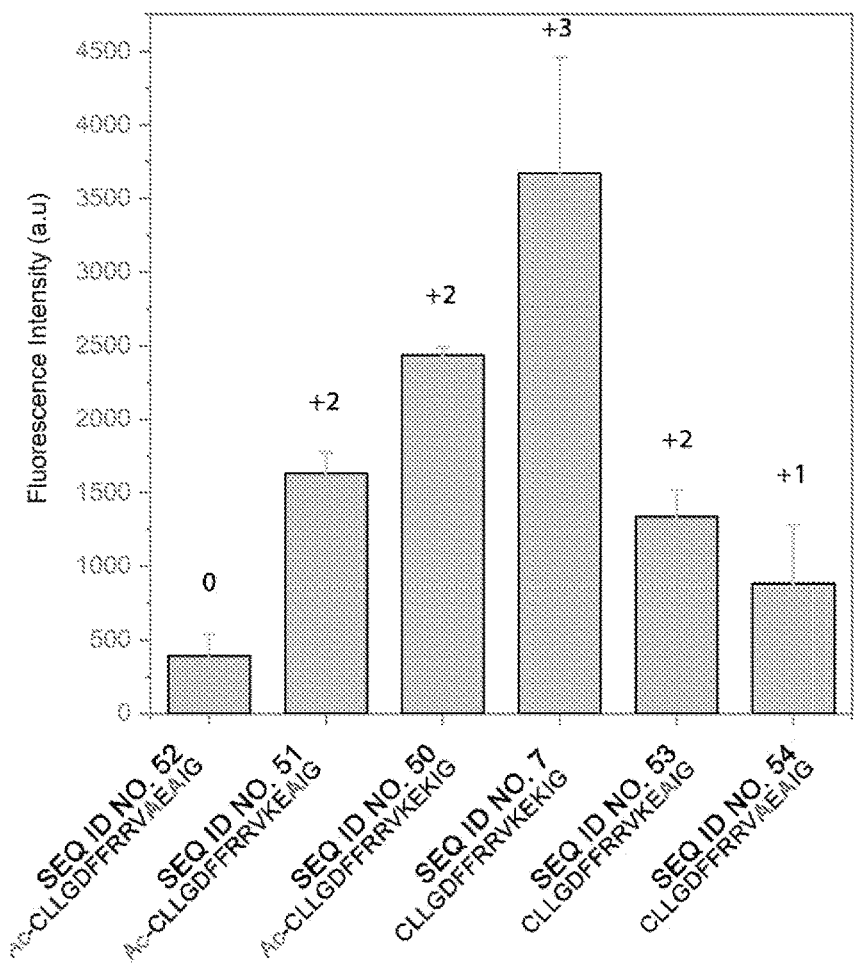
FIG. 17 shows the effect of net charge on PTAA fluorescence. N-terminal acetylated and N-terminal free LL37$_{FRRY}$ peptides with one or both positive charges outside the dibasic site substituted with alanine were assayed. The histograms represent the difference in PTAA fluorescence intensity between an intact and cleaved peptide. The number above each vertical bar refers to peptide net charge. Error bars show standard error of the mean (n=3).
Figure 18:
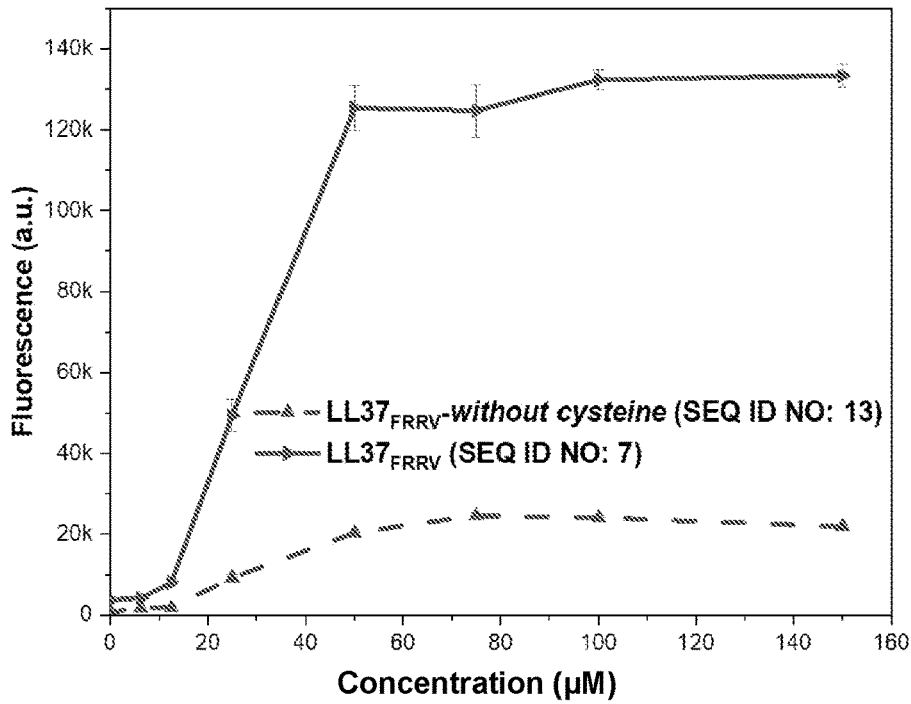
FIG. 18 shows the PT6 fluorescence intensity when mixed with increasing concentrations of LL37$_{FRRY}$ (SEQ ID NO: 7) (solid) and LL37$_{FRRY}$-without cysteine (SEQ ID NO: 13) (dashed).

Results show that PTAA fluorescence intensity increases when bound to an intact LL37$_{FRRV}$ peptide, however, the fluorescence intensity is significantly less when it interacts with short or cleaved peptides resulting from OmpT digestion (FIG. 17). This difference in fluorescence intensity between an intact and cleaved peptide will differ from peptide to peptide. A list of factors that can affect this difference include: peptide length, sequence, reaction conditions, peptide's net charge, total number of positive charges, and the distribution of charges along the peptide sequence. To understand the effect of peptide net charge and how it affects the difference in PTAA fluorescence between intact and cleaved peptides, six LL37$_{FRRY}$ peptide were modified such that their N-terminal was either free or acetyl capped and one or both positive charges outside the dibasic site substituted with alanine. This resulted in six peptides whose net charge ranged from 0 to +3. The six peptides were treated with OmpT for 6 hours to allow complete digestion of the peptides. Addition of PTAA to the above OmpT-treated samples resulted in a decrease in PTAA fluorescence when compared to PTAA fluorescence when mixed with intact peptides. The magnitude of this difference was different for the six peptides and it correlated with the change in peptide's net charge. The peptide with zero net charge showed almost no difference in PTAA fluorescence intensity between the intact peptide and one that was digested with OmpT for 6 hours (FIG. 17). However, as the peptide's net charge increased from +1 to +3, there was a corresponding increase in the magnitude of difference in PTAA fluorescence. $LL37_{FRRY}$, with the highest net positive charge of +3 shows the largest difference in fluorescence upon OmpT digestion. These results clearly indicate that the positive charges on the peptide can critically affect the assay in terms of the total decrease in PTAA fluorescence intensity between intact and cleaved peptides.

Example 10

Effect of Cysteine on PT6 Fluorescence

Stock solutions of PT6 was prepared in a reaction buffer such that the absorbance at λmax was ~1.4. All absorbance and fluorescence measurements were carried out on 100 μL samples in a flat bottom 96 well plate using a TECAN Infinite® 200 PRO (Switzerland). Fluorescence scans were collected by exciting the samples at 495 nm, further recording their emission spectrum from 525-750 nm. Stock solutions of the two peptides (Table 1) (500 μM) were prepared in a reaction buffer (20 mM sodium phosphate buffer whose pH was adjusted to 8) and stored at −20° C. until further use. In order to study the effect of cysteine on PT6 fluorescence, different concentrations (150-6.25 μM) of the two peptides (Table 12) were prepared from the stock and mixed with PT6 such that the final concentration of the PT is a 10 time dilution of the stock. The fluorescence intensities were measured as described above.

TABLE 12

Peptide $LL37_{FRRY}$ and $LL37_{FRRY}$-without cysteine

| Peptide | Sequence | SEQ ID NO. |
|---|---|---|
| $LL37_{FRRY}$ | CLLGDFFRRVKEKIG | 7 |
| $LL37_{FRRY}$-without cysteine | LLGDFFRRVKEKIG | 13 |

Results show that the PT6 fluorescence intensity when mixed with $LL37_{FRRY}$ increases with increasing peptide concentration until around 50 μM when the fluorescence intensity reaches saturation and there is no more increase even with higher peptide concentration. A similar trend of increasing fluorescence intensity was observed for $LL37_{FRRY}$ without cysteine (SEQ ID NO: 13). However, what is important to note is the absolute difference in fluorescence intensity between the two peptides. PT6 when mixed with $LL37_{FRRY}$, that has a terminal cysteine, clearly shows a much higher fluorescence intensity when compared to $LL37_{FRRY}$ that lacks a terminal cysteine. This is clear evidence that introducing a cysteine residue at the N-terminal significantly enhances PT6 and PTAA (data not shown for PTAA) fluorescence and helps improve the detection method.

It is clear from the above Examples that the detection methods of the invention provide the following advantages when compared to existing detection methods.

(i) Significant reduction in assay time: Unlike nucleotide and antibody-based methods currently employed in bacterial detection, the methods of the invention significantly reduce or altogether eliminate the need for overnight bacterial culturing of samples prior to analysis. Most non-PCR/ELISA based commercial bacterial detections kits and techniques require over 24 hours to report the results, while the invention can reduce this reporting time by up to 99%: A reporting time of 15 minutes is achievable for highly contaminated samples. A reduction of ~75% (e.g. a reporting time of 6 hours) can be achieved for samples with very low bacterial contamination (1 CFU/ml).

(ii) Highly sensitive: The methods can detect degrees of bacterial contamination as low as 1 CFU/mL.

(iii) Highly specific and customisable: The methods can be tailored to detect only specific bacteria or even specific strains by varying the sequence of the peptide employed. This is in contrast to commercially available water testing kits which are typically not bacteria-specific. However, if a more general kit is required then peptides that are non-specifically cleaved by different bacteria or multiple peptides, each selective for different bacteria, could be used.

(iv) Storage at room temperature: Unlike detection methods that rely on antibodies, the methods of the invention utilise short synthetic peptides and polythiophenes which can be lyophilized and easily stored at room temperature. This not only increases product shelf-life, but also significantly reduces transportation and storage costs.

(v) Easy-to-use: Since the method involves simple mixing of the various components, it can be easily performed by an untrained user.

These advantages are further illustrated in FIG. 1, which provides a comparison of the cost, speed of use, detection sensitivity (limit of detection), and ease of use for various existing detection methods as well as the methods of the invention. Part A) shows commercially available pathogen testing kits; and part B) laboratory-based approaches for detecting bacterial pathogens.

REFERENCES

Aydin, B. A.; Cheema, J. A.; Ammanath, G.; Toklucu, C.; Yucel, M.; Özenler, S.; Palaniappan, A I.; Liedberg. B.; Yildiz, U. H. Pixelated colorimetric nucleic acid assay. *Talanta* 209 120581 (2020).

De J. Licona-Sánchez, T.; Álvarez-Romero, G. A.; Mendoza-Huizar, L. H.; Palomar, M. E.; Galán-Vidal, C. A. Kinetics of Polypyrrole Films Doped with Sulphate Ions Electrodeposited Over Graphite—Epoxy Resin Electrode. In *Proceedings of the ECS Transactions; ECS,* 2009; Vol. 20, pp. 385-392.

Dekker, N. Cox, R. C. Kramer, R. A. Egmond M. R., Substrate specificity of the integral membrane protease ompT determined by spatially addressed peptide libraries. *Biochemistry* 40, 1694-1701 (2001).

Dekker, N. Omptin. in *Handbook of Proteolytic Enzymes* 1, 284-289 (Elsevier, 2013).

Desloges, I.; Taylor, J. A.; Mathieu, J.; John, L.; Portt, A.; Spencer, J. D.; Dewar, K.; Marczynski, G. T.; Gruenheid, S.; Thomassin, J. L.; et al. Identification and characterization of OmpT-like proteases in uropathogenic *Escherichia coli* clinical isolates. *Microbiologyopen* 2019, 8, 1-36.

Dwight, S. J.; Gaylord, B. S.; Hong, J. W.; Bazan, G. C. Perturbation of fluorescence by nonspecific interactions between anionic poly(phenylenevinylene)s and proteins: Implications for biosensors. *J. Am. Chem. Soc.* 2004, 126, 16850-16859.

Gillissen, S.; Jonforsen, M.; Kesters, E.; Johansson, T.; Theander, M.; Andersson, M. R.; Inganas, O.; Lutsen, L.; Vanderzande, D. Synthesis and characterization of poly (pyridine vinylene) via the sulfinyl precursor route. *Macromolecules* 2001, 34, 7294-7299.

Goto, H. Yokochi, Y. Yashima, E. Chirality induction in metal-induced achiral polythiophene aggregates assisted by optically active amines and polythiophene. *Chem. Commun.* 48, 3291 (2012).

Hill, B.; Roger, T.; Vorhagen, F. W. Comparative Analysis of the Quantization of Color Spaces on the Basis of the CIELAB Color-Difference Formula. *ACM Trans. Graph.* 16, 109-154 (1997).

Huang, F.; Wang, X.; Wang, D.; Yang, W.; Cao, Y. Synthesis and properties of a novel water-soluble anionic polyfluorenes for highly sensitive biosensors. *Polymer (Guildf).* 2005, 46, 12010-12015.

Kim, B. Chen, L. Gong, J. Osada, Y., Titration behavior and spectral transitions of water-soluble polythiophene carboxylic acids. *Macromolecules* 32, 3964-3969 (1999).

Kramer, R. A. Zandwijken, D. Egmond, M. R. Dekker, N. In vitro folding, purification and characterization of *Escherichia coli* outer membrane protease OmpT. *Eur. J. Biochem.* 267, 885-893 (2000).

Law, J. W.-F. et al., Rapid methods for the detection of foodborne bacterial pathogens: principles, applications, advantages and limitations. *Front. Microbiol.* 5, 770 (2014).

Lazcka, O., Campo, F. J. Del & Muñoz, F. X. Pathogen detection: A perspective of traditional methods and biosensors. *Biosens. Bioelectron.* 22, 1205-1217 (2007).

Mangel, B. W. F., Toledo, D. L. & Brown, T. Omptin: An *Escherichia coli* Outer Membrane Proteinase that Activates Plasminogen. *Methods Enzymol.* 244, 384-399 (1994).

Nilsson, K. P. R. Andersson, M. R. Inganäs, O. Conformational transitions of a free amino-acid-functionalized polythiophene induced by different buffer systems. *J. Phys. Condens. Matter* 14, 10011-10020 (2002).

Nilsson, K. P. R. Rydberg, J. Baltzer, L. Inganas, O. Self-assembly of synthetic peptides control conformation and optical properties of a zwitterionic polythiophene derivative. *Proc. Natl. Acad. Sci.* 100, 10170-10174 (2003).

Nilsson, K. P. R. Olsson, J. D. M. Konradsson, P. Inganäs, O. Enantiomeric substituents determine the chirality of luminescent conjugated polythiophenes. *Macromolecules* 37, 6316-6321 (2004).

Nilsson, K. P. R. Rydberg, J. Baltzer, L. Inganäs, O. Twisting macromolecular chains: Self-assembly of a chiral supermolecule from nonchiral polythiophene polyanions and random-coil synthetic peptides. *Proc. Natl. Acad. Sci. U.S.A.* 101, 11197-11202 (2004).

Rajwar, D.; Ammanath, G.; Cheema, J. A.; Palaniappan, A I.; Yildiz, U. H.; Liedberg, B. Tailoring Conformation-Induced Chromism of Polythiophene Copolymers for Nucleic Acid Assay at Resource Limited Settings. *ACS Appl. Mater. Interfaces* 8, 8349-8357 (2016).

Selegård, R. Rouhbakhsh, Z. Shirani, H. Johansson, L. B. G. Norman, P. Linares, M. Aili, D. Nilsson, K. P. R. Distinct Electrostatic Interactions Govern the Chiro-Optical Properties and Architectural Arrangement of Peptide-Oligothiophene Hybrid Materials. *Macromolecules* 50, 7102-7110 (2017).

Wang, Y. & Salazar, J. K. Culture-Independent Rapid Detection Methods for Bacterial Pathogens and Toxins in Food Matrices. *Compr. Rev. Food Sci. Food Saf.* 15, 183-205 (2016).

Yashima, E. Matsushima, T. Okamoto, Y. *J. Am. Chem. Soc.* 119, 6345-6359 (1997).

The invention claimed is:

1. A method for detecting in a test sample the presence or absence of bacteria expressing at least one outer membrane protease, the method comprising the steps:
    i) contacting the test sample with a peptide substrate comprising two adjacent basic amino acid residues and wherein the peptide substrate is cleaved by said protease;
    ii) simultaneously or sequentially contacting the test sample with a conjugated reporter polymer for a predetermined period of time, wherein intact peptide substrate forms a complex with the conjugated reporter polymer and induces a change in conformation of the conjugated reporter polymer, whereas the cleaved peptide fragments are unable to induce a change in conformation of the conjugated reporter polymer; and
    iii) comparing an optical absorption and/or colour and/or photoluminescence (e.g. fluorescence) of the test sample with a control.

2. The method of claim 1, wherein the method comprises the steps:
    i) contacting the test sample with the peptide substrate comprising two adjacent basic amino acid residues for a predetermined period of time;
    ii) contacting the test sample from step (i) with a conjugated reporter polymer for a predetermined period of time, wherein intact peptide substrate forms a complex with the conjugated reporter polymer and induces a change in conformation of the conjugated reporter polymer, whereas the cleaved peptide fragments are unable to induce a change in conformation of the conjugated reporter polymer; and
    iii) comparing the optical absorption and/or colour and/or photoluminescence (e.g. fluorescence) of the test sample with a control.

3. The method of claim 1, wherein the bacteria are
    i) pathogenic bacteria; and/or
    ii) gram-negative bacteria; and/or
    iii) selected from the group consisting of *Escherichia coli, Salmonella enterica, Yersinia pestis* and *Shigella flexneri.*

4. The method of claim 1, wherein the conjugated reporter polymer is:
    i) selected from the group consisting of a polythiophene; a poly(1,4-phenylene vinylene) (PPV); a poly(1,4-phenylene) (PPP); a polyfluorenes (PFO); a nitrogen-containing polymer such as polyquinoline, poly(2,5-pyridinevinylene), 1,3,4-oxadiazole, and poly(9-vinylcarbazole) (PVK); and a polypyrrole; or
    ii) a conjugated polythiophene; or
    iii) a conjugated polythiophene selected from the group consisting of polythiophene acetic acid (PTAA), Poly [3 (potassium-6-hexanoate)thiophene-2,5-diyl] (PT6) and Poly [3-(Potassium-4-butanoate)thiophene-2,5-diyl] (PT4), or any combination thereof.

5. The method of claim 1, wherein the at least one outer membrane protease is an omptin protease.

6. The method of claim 5, wherein the omptin protease is:
    i) selected from the group consisting of OmpT, OmpP, PgtE, PgtE2, Pla, PlaA SopA, SopA2, SopA3, IscP, Q8ZGQ6, Staphylococcal peptidase I, and Protease 7; or
    ii) OmpT and the bacteria is *Escherichia coli.*

7. The method of claim 1, wherein each of the basic amino acid residues is independently selected from the group consisting of Lysine, Arginine and Histidine.

8. The method of claim 7, wherein the peptide substrate comprises a cleavage site comprising an amino acid sequence set forth in the group comprising or consisting of FRRV (SEQ ID NO: 1), FRRY (SEQ ID NO: 2), FRRA (SEQ ID NO: 3), YRRA (SEQ ID NO: 4) and ARRA (SEQ ID NO: 5).

9. The method of claim 8, wherein the peptide substrate has at least 40% sequence similarity with a peptide comprising an amino acid sequence set forth in the group comprising or consisting of SEQ ID NO: 6 to SEQ ID NO: 54, or a functional fragment thereof.

10. The method of claim 9, wherein the peptide substrate is a peptide;
   i) comprising an amino acid sequence set forth in the group consisting of SEQ ID NO: 1 to 17 and SEQ ID NO: 49 to 54; or
   ii) represented by the formula X1-A-X2, wherein X1 and X2 are, independently, a sequence of 0-10 amino acid residues and A is a peptide that has at least 40% sequence similarity with a peptide set forth in any one of SEQ ID NO: 1 to 17 and SEQ ID NO: 49 to 54.

11. The method of claim 1, wherein:
the bacteria is selected from the group comprising or consisting of *Escherichia coli, Salmonella enterica, Yersinia pestis* and *Shigella flexneri;*
the conjugated reporter polymer is polythiophene acetic acid (PTAA), Poly[3(potassium-6-hexanoate)thiophene-2,5-diyl] (PT6), Poly[3-(Potassium-4-butanoate) thiophene-2,5-diyl] (PT4), or any combination thereof; and
the peptide substrate has at least 40% sequence similarity with a peptide comprising an amino acid sequence set forth in the group comprising or consisting of SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 49, SEQ ID NO: 50, SEQ ID NO: 51, SEQ ID NO: 52, SEQ ID NO: 53 and SEQ ID NO: 54, or a functional fragment thereof.

12. The method of claim 1, further comprising a pre-culturing step or pre-concentration step or a combination of both before performing step (i) of the method, wherein the pre-culturing step involves incubating the test sample under culturing conditions; and wherein the pre-concentration step involves removing excess aqueous solution from the test sample while retaining the bacteria, optionally wherein the pre-culturing step comprises culturing the test sample in a growth medium for not more than 12 hours; and/or
wherein the test sample is derived from a source selected from the group comprising or consisting of a water source, a food source, a clinical sample and a biological fluid; and/or
wherein the method comprises a test to detect contamination in water and/or food sources; and/or
wherein the method comprises a clinical and/or diagnostic test.

13. The method of claim 1, wherein said predetermined period of time for contacting the test sample with a conjugated reporter polymer is in a range of 1 minute to 2 hours.

* * * * *

SEQUENCE LISTING

```
<160> NUMBER OF SEQ ID NOS: 54

<210> SEQ ID NO 1
<211> LENGTH: 4
<212> TYPE: PRT
<213> ORGANISM: Artificial Sequence
<220> FEATURE:
<223> OTHER INFORMATION: Cleavage site FRRV

<400> SEQUENCE: 1

Phe Arg Arg Val
1

<210> SEQ ID NO 2
<211> LENGTH: 4
<212> TYPE: PRT
<213> ORGANISM: Artificial Sequence
<220> FEATURE:
<223> OTHER INFORMATION: Cleavage site FRRY

<400> SEQUENCE: 2

Phe Arg Arg Tyr
1

<210> SEQ ID NO 3
<211> LENGTH: 4
<212> TYPE: PRT
```

```
<213> ORGANISM: Artificial Sequence
<220> FEATURE:
<223> OTHER INFORMATION: Cleavage site FRRA

<400> SEQUENCE: 3

Phe Arg Arg Ala
1

<210> SEQ ID NO 4
<211> LENGTH: 4
<212> TYPE: PRT
<213> ORGANISM: Artificial Sequence
<220> FEATURE:
<223> OTHER INFORMATION: Cleavage site YRRA

<400> SEQUENCE: 4

Tyr Arg Arg Ala
1

<210> SEQ ID NO 5
<211> LENGTH: 4
<212> TYPE: PRT
<213> ORGANISM: Artificial Sequence
<220> FEATURE:
<223> OTHER INFORMATION: Cleavage site ARRA

<400> SEQUENCE: 5

Ala Arg Arg Ala
1

<210> SEQ ID NO 6
<211> LENGTH: 37
<212> TYPE: PRT
<213> ORGANISM: Artificial Sequence
<220> FEATURE:
<223> OTHER INFORMATION: Cathelicidin LL37

<400> SEQUENCE: 6

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
        35

<210> SEQ ID NO 7
<211> LENGTH: 15
<212> TYPE: PRT
<213> ORGANISM: Artificial Sequence
<220> FEATURE:
<223> OTHER INFORMATION: LL37FRRV

<400> SEQUENCE: 7

Cys Leu Leu Gly Asp Phe Phe Arg Arg Val Lys Glu Lys Ile Gly
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: LL37FRRY

<400> SEQUENCE: 8

Cys Leu Leu Gly Asp Phe Phe Arg Arg Tyr Lys Glu Lys Ile Gly
1               5                   10                  15
```

```
<210> SEQ ID NO 9
<211> LENGTH: 15
<212> TYPE: PRT
<213> ORGANISM: Artificial Sequence
<220> FEATURE:
<223> OTHER INFORMATION: LL37FRRA

<400> SEQUENCE: 9

Cys Leu Leu Gly Asp Phe Phe Arg Arg Ala Lys Glu Lys Ile Gly
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: LL37YRRA

<400> SEQUENCE: 10

Cys Leu Leu Gly Asp Phe Tyr Arg Arg Ala Lys Glu Lys Ile Gly
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: LL37ARRA

<400> SEQUENCE: 11

Cys Leu Leu Gly Asp Phe Ala Arg Arg Ala Lys Glu Lys Ile Gly
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: LL37ARKA

<400> SEQUENCE: 12

Cys Leu Leu Gly Asp Phe Ala Arg Lys Ala Lys Glu Lys Ile Gly
1               5                   10                  15

<210> SEQ ID NO 13
<211> LENGTH: 14
<212> TYPE: PRT
<213> ORGANISM: Artificial Sequence
<220> FEATURE:
<223> OTHER INFORMATION: LL37FRRV without Cysteine

<400> SEQUENCE: 13

Leu Leu Gly Asp Phe Phe Arg Arg Val Lys Glu Lys Ile Gly
1               5                   10

<210> SEQ ID NO 14
<211> LENGTH: 14
<212> TYPE: PRT
<213> ORGANISM: Artificial Sequence
<220> FEATURE:
<223> OTHER INFORMATION: L37FRRY without Cysteine

<400> SEQUENCE: 14

Leu Leu Gly Asp Phe Phe Arg Arg Tyr Lys Glu Lys Ile Gly
1               5                   10
```

```
<210> SEQ ID NO 15
<211> LENGTH: 14
<212> TYPE: PRT
<213> ORGANISM: Artificial Sequence
<220> FEATURE:
<223> OTHER INFORMATION: LL37FRRA without Cysteine

<400> SEQUENCE: 15

Leu Leu Gly Asp Phe Phe Arg Arg Ala Lys Glu Lys Ile Gly
1               5                   10

<210> SEQ ID NO 16
<211> LENGTH: 14
<212> TYPE: PRT
<213> ORGANISM: Artificial Sequence
<220> FEATURE:
<223> OTHER INFORMATION: LL37YRRA without Cysteine

<400> SEQUENCE: 16

Leu Leu Gly Asp Phe Tyr Arg Arg Ala Lys Glu Lys Ile Gly
1               5                   10

<210> SEQ ID NO 17
<211> LENGTH: 14
<212> TYPE: PRT
<213> ORGANISM: Artificial Sequence
<220> FEATURE:
<223> OTHER INFORMATION: LL37ARRA without Cysteine

<400> SEQUENCE: 17

Leu Leu Gly Asp Phe Ala Arg Arg Ala Lys Glu Lys Ile Gly
1               5                   10

<210> SEQ ID NO 18
<211> LENGTH: 37
<212> TYPE: PRT
<213> ORGANISM: Artificial Sequence
<220> FEATURE:
<223> OTHER INFORMATION: Cecropin A

<400> SEQUENCE: 18

Lys Trp Lys Leu Phe Lys Lys Ile Glu Lys Val Gly Gln Asn Ile Arg
1               5                   10                  15

Asp Gly Ile Ile Lys Ala Gly Pro Ala Val Ala Val Val Gly Gln Ala
            20                  25                  30

Thr Gln Ile Ala Lys
        35

<210> SEQ ID NO 19
<211> LENGTH: 31
<212> TYPE: PRT
<213> ORGANISM: Artificial Sequence
<220> FEATURE:
<223> OTHER INFORMATION: Cecropin P1

<400> SEQUENCE: 19

Ser Trp Leu Ser Lys Thr Ala Lys Lys Leu Glu Asn Ser Ala Lys Lys
1               5                   10                  15

Arg Ile Ser Glu Gly Ile Ala Ile Ala Ile Gln Gly Gly Pro Arg
            20                  25                  30

<210> SEQ ID NO 20
<211> LENGTH: 59
<212> TYPE: PRT
<213> ORGANISM: Artificial Sequence
```

```
<220> FEATURE:
<223> OTHER INFORMATION: CECD

<400> SEQUENCE: 20

Met Asn Phe Thr Lys Leu Phe Ala Ile Val Leu Leu Ala Ala Leu Val
1               5                   10                  15

Leu Leu Gly Gln Thr Glu Ala Gly Gly Leu Lys Lys Leu Gly Lys Lys
            20                  25                  30

Leu Glu Gly Ala Gly Lys Arg Val Phe Lys Ala Ser Glu Lys Ala Leu
        35                  40                  45

Pro Val Val Val Gly Ile Lys Ala Ile Gly Lys
    50                  55

<210> SEQ ID NO 21
<211> LENGTH: 37
<212> TYPE: PRT
<213> ORGANISM: Artificial Sequence
<220> FEATURE:
<223> OTHER INFORMATION: Papiliocin

<400> SEQUENCE: 21

Arg Trp Lys Ile Phe Lys Lys Ile Glu Lys Val Gly Arg Asn Val Arg
1               5                   10                  15

Asp Gly Ile Ile Lys Ala Gly Pro Ala Val Ala Val Val Gly Gln Ala
            20                  25                  30

Ala Thr Val Val Lys
        35

<210> SEQ ID NO 22
<211> LENGTH: 66
<212> TYPE: PRT
<213> ORGANISM: Artificial Sequence
<220> FEATURE:
<223> OTHER INFORMATION: Moricin

<400> SEQUENCE: 22

Met Asn Ile Leu Lys Phe Phe Phe Val Phe Ile Val Ala Met Ser Leu
1               5                   10                  15

Val Ser Cys Ser Thr Ala Ala Pro Ala Lys Ile Pro Ile Lys Ala Ile
            20                  25                  30

Lys Thr Val Gly Lys Ala Val Gly Lys Gly Leu Arg Ala Ile Asn Ile
        35                  40                  45

Ala Ser Thr Ala Asn Asp Val Phe Asn Phe Leu Lys Pro Lys Lys Arg
    50                  55                  60

Lys His
65

<210> SEQ ID NO 23
<211> LENGTH: 36
<212> TYPE: PRT
<213> ORGANISM: Artificial Sequence
<220> FEATURE:
<223> OTHER INFORMATION: Ceratotoxin A (CtxA)

<400> SEQUENCE: 23

Ser Ile Gly Ser Ala Leu Lys Lys Ala Leu Pro Val Ala Lys Lys Ile
1               5                   10                  15

Gly Lys Ile Ala Leu Pro Ile Ala Lys Ala Ala Leu Pro Val Ala Ala
            20                  25                  30

Gly Leu Val Gly
        35
```

```
<210> SEQ ID NO 24
<211> LENGTH: 26
<212> TYPE: PRT
<213> ORGANISM: Artificial Sequence
<220> FEATURE:
<223> OTHER INFORMATION: Melittin

<400> SEQUENCE: 24

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 25
<211> LENGTH: 39
<212> TYPE: PRT
<213> ORGANISM: Artificial Sequence
<220> FEATURE:
<223> OTHER INFORMATION: Magainin 2, Cecropin A

<400> SEQUENCE: 25

Lys Trp Lys Leu Phe Lys Lys Ile Lys Phe Leu His Ser Ala Lys Lys
1               5                   10                  15

Phe Ile Gly Lys Phe Leu His Ser Ala Lys Lys Phe Gly Lys Ala Phe
            20                  25                  30

Val Gly Glu Ile Met Asn Ser
        35

<210> SEQ ID NO 26
<211> LENGTH: 27
<212> TYPE: PRT
<213> ORGANISM: Artificial Sequence
<220> FEATURE:
<223> OTHER INFORMATION: Dermaseptin

<400> SEQUENCE: 26

Ala Leu Trp Met Thr Leu Leu Lys Lys Val Leu Lys Ala Ala Ala Lys
1               5                   10                  15

Ala Leu Asn Ala Val Leu Val Gly Ala Asn Ala
            20                  25

<210> SEQ ID NO 27
<211> LENGTH: 21
<212> TYPE: PRT
<213> ORGANISM: Artificial Sequence
<220> FEATURE:
<223> OTHER INFORMATION: Bombinin-H4

<400> SEQUENCE: 27

Ile Ile Gly Pro Val Leu Gly Leu Val Gly Ser Ala Leu Gly Gly Leu
1               5                   10                  15

Leu Lys Lys Ile Gly
            20

<210> SEQ ID NO 28
<211> LENGTH: 24
<212> TYPE: PRT
<213> ORGANISM: Artificial Sequence
<220> FEATURE:
<223> OTHER INFORMATION: Brevinin-1

<400> SEQUENCE: 28

Phe Leu Pro Val Leu Ala Gly Ile Ala Ala Lys Val Val Pro Ala Leu
```

Phe Cys Lys Ile Thr Lys Lys Cys
            20

<210> SEQ ID NO 29
<211> LENGTH: 33
<212> TYPE: PRT
<213> ORGANISM: Artificial Sequence
<220> FEATURE:
<223> OTHER INFORMATION: Abaecin

<400> SEQUENCE: 29

Cys Ala Ala Phe Ala Tyr Val Pro Leu Pro Asn Val Pro Gln Pro Gly
1               5                   10                  15

Arg Arg Pro Phe Pro Thr Phe Pro Gly Gln Gly Pro Phe Asn Pro Lys
            20                  25                  30

Ile

<210> SEQ ID NO 30
<211> LENGTH: 13
<212> TYPE: PRT
<213> ORGANISM: Artificial Sequence
<220> FEATURE:
<223> OTHER INFORMATION: Indolicidin

<400> SEQUENCE: 30

Ile Leu Pro Trp Lys Trp Pro Trp Trp Pro Trp Arg Arg
1               5                   10

<210> SEQ ID NO 31
<211> LENGTH: 43
<212> TYPE: PRT
<213> ORGANISM: Artificial Sequence
<220> FEATURE:
<223> OTHER INFORMATION: BACTENECIN 5

<400> SEQUENCE: 31

Arg Phe Arg Pro Pro Ile Arg Arg Pro Pro Ile Arg Pro Pro Phe Tyr
1               5                   10                  15

Pro Pro Phe Arg Pro Pro Ile Arg Pro Pro Ile Phe Pro Pro Ile Arg
            20                  25                  30

Pro Pro Phe Arg Pro Pro Leu Gly Pro Phe Pro
        35                  40

<210> SEQ ID NO 32
<211> LENGTH: 22
<212> TYPE: PRT
<213> ORGANISM: Artificial Sequence
<220> FEATURE:
<223> OTHER INFORMATION: Heliocin

<400> SEQUENCE: 32

Gln Arg Phe Ile His Pro Thr Tyr Arg Pro Pro Pro Gln Pro Arg Arg
1               5                   10                  15

Pro Val Ile Met Arg Ala
            20

<210> SEQ ID NO 33
<211> LENGTH: 41
<212> TYPE: PRT
<213> ORGANISM: Artificial Sequence
<220> FEATURE:
<223> OTHER INFORMATION: Chicken AvBD5

```
<400> SEQUENCE: 33

Gly Leu Pro Gln Asp Cys Glu Arg Arg Gly Gly Phe Cys Ser His Lys
1               5                   10                  15

Ser Cys Pro Pro Gly Ile Gly Arg Ile Gly Leu Cys Ser Lys Glu Asp
                20                  25                  30

Phe Cys Cys Arg Ser Arg Trp Tyr Ser
            35                  40

<210> SEQ ID NO 34
<211> LENGTH: 13
<212> TYPE: PRT
<213> ORGANISM: Artificial Sequence
<220> FEATURE:
<223> OTHER INFORMATION: Andersonin-C1

<400> SEQUENCE: 34

Thr Ser Arg Cys Ile Phe Tyr Arg Arg Lys Lys Cys Ser
1               5                   10

<210> SEQ ID NO 35
<211> LENGTH: 26
<212> TYPE: PRT
<213> ORGANISM: Artificial Sequence
<220> FEATURE:
<223> OTHER INFORMATION: NRC-20

<400> SEQUENCE: 35

Gly Phe Leu Gly Ile Leu Phe His Gly Val His His Gly Arg Lys Lys
1               5                   10                  15

Ala Leu His Met Asn Ser Glu Arg Ser
                20                  25

<210> SEQ ID NO 36
<211> LENGTH: 24
<212> TYPE: PRT
<213> ORGANISM: Artificial Sequence
<220> FEATURE:
<223> OTHER INFORMATION: NCR247

<400> SEQUENCE: 36

Arg Asn Gly Cys Ile Val Asp Pro Arg Cys Pro Tyr Gln Gln Cys Arg
1               5                   10                  15

Arg Pro Leu Tyr Cys Arg Arg Arg
                20

<210> SEQ ID NO 37
<211> LENGTH: 33
<212> TYPE: PRT
<213> ORGANISM: Artificial Sequence
<220> FEATURE:
<223> OTHER INFORMATION: mBD-12

<400> SEQUENCE: 37

Cys Arg Leu Gly Arg Gly Lys Cys Arg Arg Thr Cys Ile Glu Ser Glu
1               5                   10                  15

Lys Ile Ala Gly Trp Cys Lys Leu Asn Phe Phe Cys Cys Arg Glu Arg
                20                  25                  30

Ile

<210> SEQ ID NO 38
<211> LENGTH: 33
<212> TYPE: PRT
<213> ORGANISM: Artificial Sequence
```

```
<220> FEATURE:
<223> OTHER INFORMATION: mBD-6

<400> SEQUENCE: 38

Cys Met Ser Tyr Gly Gly Ser Cys Gln Arg Ser Cys Asn Gly Gly Phe
1               5                   10                  15

Arg Leu Gly Gly His Cys Gly His Pro Lys Ile Arg Cys Cys Arg Arg
                20                  25                  30

Lys

<210> SEQ ID NO 39
<211> LENGTH: 43
<212> TYPE: PRT
<213> ORGANISM: Artificial Sequence
<220> FEATURE:
<223> OTHER INFORMATION: Hg-CATH

<400> SEQUENCE: 39

Arg Arg Phe Arg Arg Thr Val Gly Leu Ser Lys Phe Phe Arg Lys Ala
1               5                   10                  15

Arg Lys Lys Leu Gly Lys Gly Leu Gln Lys Ile Lys Asn Val Leu Arg
                20                  25                  30

Lys Tyr Leu Pro Arg Pro Gln Tyr Ala Tyr Ala
                35                  40

<210> SEQ ID NO 40
<211> LENGTH: 32
<212> TYPE: PRT
<213> ORGANISM: Artificial Sequence
<220> FEATURE:
<223> OTHER INFORMATION: Tur1B

<400> SEQUENCE: 40

Arg Arg Ile Pro Phe Trp Pro Pro Asn Trp Pro Gly Pro Trp Leu Pro
1               5                   10                  15

Pro Trp Ser Pro Pro Asp Phe Arg Ile Pro Arg Ile Leu Arg Lys Arg
                20                  25                  30

<210> SEQ ID NO 41
<211> LENGTH: 32
<212> TYPE: PRT
<213> ORGANISM: Artificial Sequence
<220> FEATURE:
<223> OTHER INFORMATION: Tur1A

<400> SEQUENCE: 41

Arg Arg Ile Arg Phe Arg Pro Pro Tyr Leu Pro Arg Pro Gly Arg Arg
1               5                   10                  15

Pro Arg Phe Pro Pro Pro Phe Pro Ile Pro Arg Ile Pro Arg Ile Pro
                20                  25                  30

<210> SEQ ID NO 42
<211> LENGTH: 17
<212> TYPE: PRT
<213> ORGANISM: Artificial Sequence
<220> FEATURE:
<223> OTHER INFORMATION: Tachyplesin I

<400> SEQUENCE: 42

Lys Trp Cys Phe Arg Val Cys Tyr Arg Gly Ile Cys Tyr Arg Arg Cys
1               5                   10                  15

Arg
```

<210> SEQ ID NO 43
<211> LENGTH: 31
<212> TYPE: PRT
<213> ORGANISM: Artificial Sequence
<220> FEATURE:
<223> OTHER INFORMATION: NEMURI

<400> SEQUENCE: 43

Asp Ala Arg Ala Arg Arg Ile Val Arg Ala Gly Arg Arg Gly Gly
1               5                   10                  15

Arg Arg Gly Gly Arg Arg Gly Gly Arg Arg Ser Ala Arg Lys Ser
            20                  25                  30

<210> SEQ ID NO 44
<211> LENGTH: 27
<212> TYPE: PRT
<213> ORGANISM: Artificial Sequence
<220> FEATURE:
<223> OTHER INFORMATION: ModoCath6

<400> SEQUENCE: 44

Val Arg Arg Ser Lys Arg Gly Ile Lys Val Pro Ser Phe Val Lys
1               5                   10                  15

Val Leu Lys Asp Val Val Ser Glu Ser Ile Ser
            20                  25

<210> SEQ ID NO 45
<211> LENGTH: 24
<212> TYPE: PRT
<213> ORGANISM: Artificial Sequence
<220> FEATURE:
<223> OTHER INFORMATION: Myticalin C6

<400> SEQUENCE: 45

Arg Arg Arg Arg Arg Phe Arg Arg Val Ile Arg Arg Ile Arg Leu Pro
1               5                   10                  15

Lys Tyr Leu Thr Ile Asn Thr Glu
            20

<210> SEQ ID NO 46
<211> LENGTH: 34
<212> TYPE: PRT
<213> ORGANISM: Artificial Sequence
<220> FEATURE:
<223> OTHER INFORMATION: mCRAMP

<400> SEQUENCE: 46

Gly Leu Leu Arg Lys Gly Gly Glu Lys Ile Gly Glu Lys Leu Lys Lys
1               5                   10                  15

Ile Gly Gln Lys Ile Lys Asn Phe Phe Gln Lys Leu Val Pro Gln Pro
            20                  25                  30

Glu Gln

<210> SEQ ID NO 47
<211> LENGTH: 8
<212> TYPE: PRT
<213> ORGANISM: Artificial Sequence
<220> FEATURE:
<223> OTHER INFORMATION: Fragment 1 of LL37FRRV

<400> SEQUENCE: 47

Cys Leu Leu Gly Asp Phe Phe Arg
1               5

```
<210> SEQ ID NO 48
<211> LENGTH: 7
<212> TYPE: PRT
<213> ORGANISM: Artificial Sequence
<220> FEATURE:
<223> OTHER INFORMATION: Fragment 2 of LL37FRRV

<400> SEQUENCE: 48

Arg Val Lys Glu Lys Ile Gly
1               5

<210> SEQ ID NO 49
<211> LENGTH: 7
<212> TYPE: PRT
<213> ORGANISM: Artificial Sequence
<220> FEATURE:
<223> OTHER INFORMATION: GXRRXGC
<220> FEATURE:
<221> NAME/KEY: MOD_RES
<222> LOCATION: (1)..(1)
<223> OTHER INFORMATION: G is acetylated
<220> FEATURE:
<221> NAME/KEY: MISC_FEATURE
<222> LOCATION: (2)..(2)
<223> OTHER INFORMATION: Xaa is any amino acid except Cysteine.
<220> FEATURE:
<221> NAME/KEY: MISC_FEATURE
<222> LOCATION: (5)..(5)
<223> OTHER INFORMATION: Xaa is any amino acid except Cysteine.

<400> SEQUENCE: 49

Gly Xaa Arg Arg Xaa Gly Cys
1               5

<210> SEQ ID NO 50
<211> LENGTH: 15
<212> TYPE: PRT
<213> ORGANISM: Artificial Sequence
<220> FEATURE:
<223> OTHER INFORMATION: LL37FRRV with acetyl cap
<220> FEATURE:
<221> NAME/KEY: MOD_RES
<222> LOCATION: (1)..(1)
<223> OTHER INFORMATION: Acetyl cap

<400> SEQUENCE: 50

Cys Leu Leu Gly Asp Phe Phe Arg Arg Val Lys Glu Lys Ile Gly
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: LL37FRRV with 1 Ala substitution and acetyl cap
<220> FEATURE:
<221> NAME/KEY: MOD_RES
<222> LOCATION: (1)..(1)
<223> OTHER INFORMATION: Acetyl cap

<400> SEQUENCE: 51

Cys Leu Leu Gly Asp Phe Phe Arg Arg Val Lys Glu Ala Ile Gly
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: LL37FRRV with 2 Ala substitutions and acetyl
```

```
                                    cap
<220> FEATURE:
<221> NAME/KEY: MOD_RES
<222> LOCATION: (1)..(1)
<223> OTHER INFORMATION: Acetyl cap

<400> SEQUENCE: 52

Cys Leu Leu Gly Asp Phe Phe Arg Arg Val Ala Glu Ala Ile Gly
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: LL37FRRV with 1 Ala substitution

<400> SEQUENCE: 53

Cys Leu Leu Gly Asp Phe Phe Arg Arg Val Lys Glu Ala Ile Gly
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: LL37FRRV with 2 Ala substitutions

<400> SEQUENCE: 54

Cys Leu Leu Gly Asp Phe Phe Arg Arg Val Ala Glu Ala Ile Gly
1               5                   10                  15
```